(12) United States Patent
Moreau et al.

(10) Patent No.: US 8,766,054 B2
(45) Date of Patent: Jul. 1, 2014

(54) PHYTOPHTHORA RESISTANCE IN SWEET PEPPERS

(75) Inventors: Michael Moreau, Saint Remy de Provence (FR); Frederic Denet, Chateaurenard (FR); Ophelie Sicard, Brain sur l'Authion (FR); Cecile Marchal, St Remy de Provence (FR); Claude Basterreix, Eygalieres (FR)

(73) Assignee: HM.CLAUSE, Portes les Valence (FR)

( * ) Notice: Subject to any disclaimer, the term of this patent is extended or adjusted under 35 U.S.C. 154(b) by 450 days.

(21) Appl. No.: 12/963,200

(22) Filed: Dec. 8, 2010

(65) Prior Publication Data
US 2012/0151622 A1 Jun. 14, 2012

(51) Int. Cl.
A01H 5/00 (2006.01)
A01H 1/04 (2006.01)

(52) U.S. Cl.
USPC ........................................ 800/317.1; 800/267

(58) Field of Classification Search
None
See application file for complete search history.

(56) References Cited

U.S. PATENT DOCUMENTS

2010/0115655 A1  5/2010  Mccarthy

OTHER PUBLICATIONS

Walker et al (J Amer Soc Hort Sci 124(1): 14-18, 1999).*
Candole et al (HortScience 45(2): 254-259, 2010, cited in the IDS filed Oct. 8, 2012).*
Foster et al. "Managing *Phytophthora* Crown and Root Rot in Bell Pepper Using, Fungicides and Host Resistance", Plant Disease, 94(6):697-702, Jun. 1, 2010.
Candole et al. "Screening *Capsicum annuum* Accessions for Resistance to Six Isolates of *Phytophthora capsici*", Hortscience, 45(2):254-259, Feb. 2010.
Bonnet et al., "Are the polygenic architectures of resistance to *Phytophthora capsici* and *P. parasitica* independent in pepper?" Theoretical and Applied Genetics, 115(2):253-264, May 12, 2007.
Barchi et al., "QTL analysis of plant development and fruit traits in peper and performance of selective phenotyping", Theoretical and Applied Genetics; 118(6):1157-1171, Feb. 2009.
Kim et al., "BAC-derived markers converted from RFLP linked to *Phytophthora capsici* resistance in pepper (*Capsicum annuum* L.)", Theoretical and Applied Genetics; 118(1):15-27, Sep. 2008.
Thabuis et al., "Phenotypic and molecular evaluation of a recurrent selection program for a polygenic resistance to *Phytophthora capsici* in pepper", Theoretical and Applied Genetics; 109(2):342-351, Jul. 2004.
Thabuis et al., "Marker-assisted introgression of 4 *Phytophthora capsici* resistance QTI, alleles into a bell pepper line: validation of additive and epistatic effects", Molecular Breeding: New Strategies in Plant Improvement, 14(1):9-20, Aug. 2004.
Minamiyama et al., "An SSR-based linkage map of *Capsicum annuum*", Molecular Breeding, 18(2):157-169, Aug. 2006.
International Search Report based on International Application No. PCT.IB2011/003088, mailed Mar. 21, 2012.
Chaim et al., "QTL mapping of fruit-related traits in pepper (*Capsicum annuum*)", Theor Appl Genet (2001) 102:1016-1028.
Glosier et al., "A differential series of pepper (*Capsicum annuum*) lines delineates fourteen physiological races of *Phytophthora capsici*", Euphytica, DOI 10.1007/s10681-007-9532-1, 2007.
Minamiyama et al., "QTL Analysis for Resistance to *Phytophthora capsici* in Pepper Using a High Density SSR-based Map", Breeding Science 57:129-134 (2007).
Ogundiwin et al., Construction of 2 intraspecific linkage maps and identification of resistance QTLs for *Phytophthora capsici* root-rot and foliar-blight diseases of pepper (*Capsicum annum* L.), Genome 48:698-711 (2005).
Rao et al., "Mapping of yield-related QTLs in pepper in an interspecific cross of *Capsicum annum* and *C. frutescens*", Theor Appl Genet (2003) 106:1457-1466.
Sugita et al., "QTL Analysis for Resistance to *Phytophthora* Blight (*Phytophthora capsici* Leon.) Using an Intraspecific Doubled-Haploid Population of *Capsicum annuum*", Breeding Science 56:137-145 (2006).
Sy et al., "Inheritance of *Phytophthora* Stem Blight Resistance as Compared to *Phytophthora* Root Rot and *Phytophthora* Foliar Blight Resistance in *Capsicum annuum* L." J. Amer. Soc. Hort. Sci. 130(1):75-78, 2005.
Thabuis et al., "Comparative mapping of *Phytophthora* resistance loci in pepper germplasm: evidence for conserved resistance loci across Solanaceae and for a large genetic diversity", Theor Appl Genet (2003) 106:1473-1485.
University of California Davis, "A Pepper Primer—introducing the *Capsicums*", retrieved from http://sbc.ucdavis.edu/files/pepper_primer.ppt on Mar. 4, 2013, publication date unknown.
Online advertisement for "Early Jalapeño Pepper Conventional & Organic", retrieved from http://www.territorialseed.com/product/1046/Organic_Pepper_Seed on Mar. 4, 2013, publication date unknown.
Online advertisement for "Sweet Bell Pepper Seeds—Keystone Resistant Giant", retrieved from http://www.localharvest.org/sweet-bell-pepper-seeds-keystone-resistant-... 1 on Mar. 4, 2013, publication date unknown.
Online advertisements for Camelot sweet peppers, Cascabella peppers, Chicken Heart hot peppers, Ancho San Luis peppers, Chile de Chapa hot peppers, Pasilla Bajio peppers, Chilhuacle Amarillo peppers, Meco pepper, Szechuan hot peppers, and Red hot pepper, retrieved from various websites from Mar. 4-6, 2013, publication date unknown.

\* cited by examiner

*Primary Examiner* — Shubo (Joe) Zhou
*Assistant Examiner* — Keith Robinson
(74) *Attorney, Agent, or Firm* — Cooley LLP

(57) ABSTRACT

The present invention provides sweet bell pepper (*Capsicum annuum*) plants with high levels of resistance to *Phytophthora* combined with desirable agronomic traits. The present invention also provides methods of making such plants and methods of using such plants to produce additional *Phytophthora*-resistant sweet bell pepper plants.

28 Claims, 6 Drawing Sheets

Figure 1:
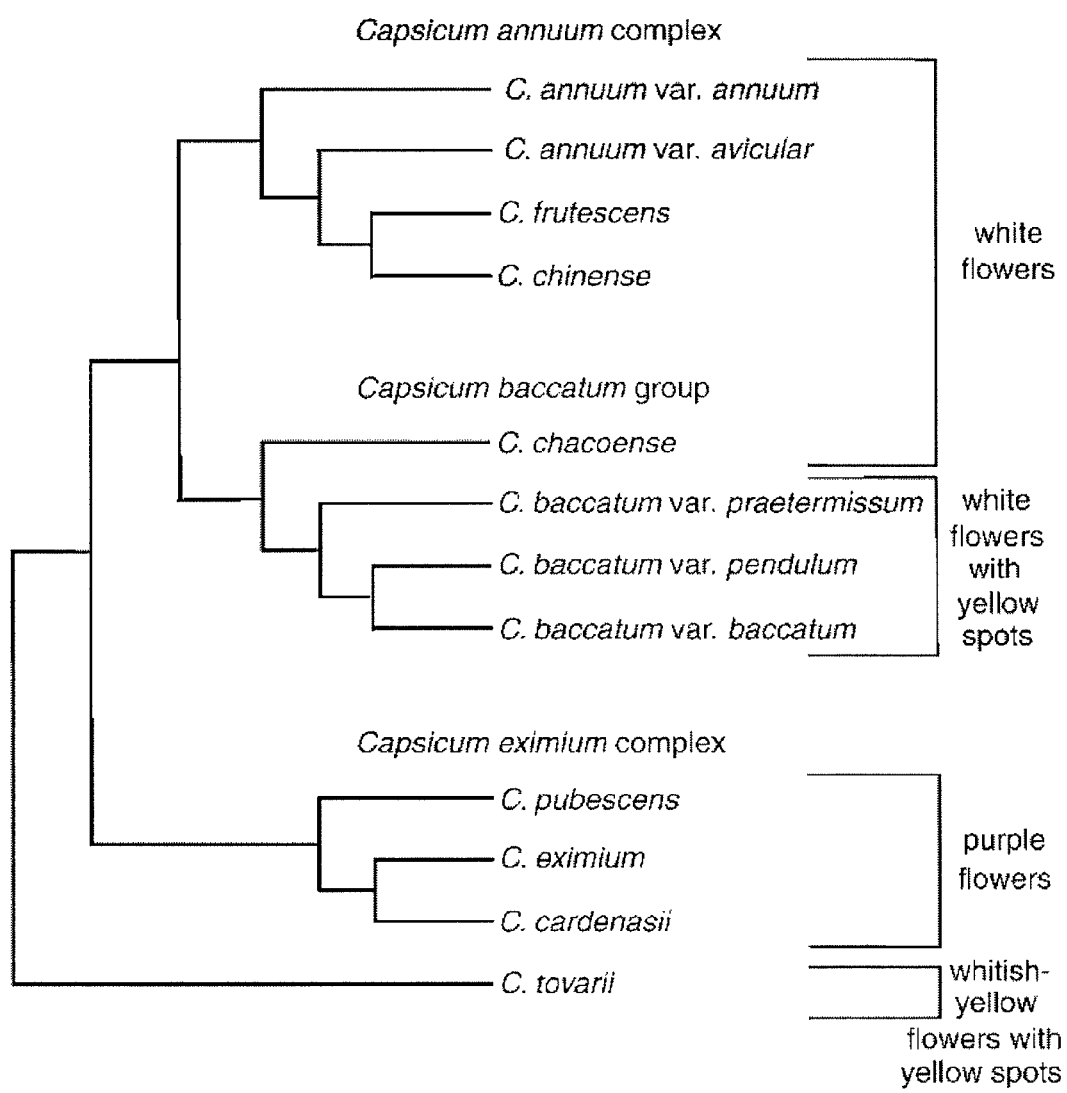

A - Heiser & Smith 1948
B - Pickersgill 1971
C - Smith & Heiser 1951
D - Heiser & Smith 1953
E - Eshbaugh 1976
F - Lippert et al. 1966
G - Smith & Heiser 1957
H - Eshbaugh 1970
I - Heiser & Smith 1958
J - Emboden 1961

━━━ highly fertile
――― viable hybrids and seeds
――- sterile F1 progeny
······ completely sterile A: 8-10 cm (width top), 8-10 cm (height), 8-10 cm (width bottom)

B: 9-10 cm (width top), 12-15 cm (height), 7-8 cm (width bottom), 1/2 long

C: 8-10 cm (width top), 15-18 cm (height), 6-8 cm (width bottom), 3/4 long

PHYTOPHTHORA RESISTANCE IN SWEET PEPPERS

TECHNICAL FIELD

The present invention relates to plant breeding, plant pathology and molecular biology. More specifically, the present invention relates to agronomically useful pepper plants that are resistant to *Phytophthora capsici* and methods of producing and using such plants.

BACKGROUND

The oomycete *Phytophthora capsici* Leonian is the causative agent of *Phytophthora* root rot, stem blight, and fruit rot in sweet bell pepper (*Capsicum annuum*). *Phytophthora*, sometimes also referred to as *Phytophtora*, is one of the most devastating diseases of peppers worldwide, potentially capable of causing large economic losses due to lower yields and/or damaged fruit. Breeding for *Phytophthora* resistant pepper plants is difficult due primarily to the existence of many different physiological races of the causative agent (Oelke et al., 2003, Glosier et al., 2007, Sy et al., 2008), the complex heritability of genetic resistance in the plant, and negative linkage drag of undesirable agronomic traits with the higher levels of genetic resistance available in unadapted germplasm.

Few good sources of resistance to *Phytophthora* are available in pepper. 'Criollo de Morelos 334' ('CM334'), a perennial pepper, and 'PI201234', a plant introduction, have been described as having resistance, but these lines are exotic landraces with undesirable agronomic traits, such as having small pungent fruits. 'CM334' has the highest level of resistance against all known isolates of *P. capsici*. From this source, the number of Quantitative Trait Loci (QTL) explaining the resistance or tolerance to one race is estimated to vary between 2 QTLs (Minamiyama et al., 2007) up to 5-6 QTLs (Thabuis et al., 2003, Ogundiwin et al., 2005). While Marker Assisted Breeding (MAB) and recurrent selection programs have been used by pepper breeders in attempts to introgress the chromosomic fragments containing the resistant QTLs into sweet peppers, the resultant pepper lines lack the full resistance of the donor parent and/or fail to maintain certain desirable agronomic traits of the recurrent parent, such as the elite sweet blocky fruit preferred by producers and direct consumers of peppers (Thabuis et al., 2001, 2004). Thus, negative linkage drag and the difficulty of retaining multiple resistance QTLs in segregating progeny over generations of selection have inhibited the ability of breeders to develop elite, agronomically-acceptable bell pepper plants with the high levels of *Phytophthora* resistance desirable for commercial production.

The current invention provides new classes of elite sweet pepper lines with high levels of resistance to *Phytophthora* combined with highly desirable agronomic traits.

SUMMARY

The present invention provides *Capsicum annuum* plants resistant to *Phytophthora* (a.k.a. *Phytophtora*). In some embodiments, the *Phytophthora* is *P. capsici*. In some embodiments, said plants comprise quantitative Trait Loci (QTLs) associated with resistance to *Phytophthora*. In some embodiments, said plants comprise one or more QTLs, for example, at least 4, 5, or 6 QTLs associated with resistance to *Phytophthora*. For example, the plants comprise at least four QTLs, at least five QTLs, and at least six QTLs which can, for example, be found in 'CM334'. In some embodiments, said plants have blocky type fruits or rectangular ¾ long type fruits (often referred as lamuyo types fruit) or half long type fruits.

In some embodiments, said QTLs map to the four linkage groups LG1/8, LG3, LG5, and LG10. In some further embodiments, said plants have a blocky type, a ¾ long type, or a half long type fruit shape. In some further embodiments, said *Capsicum annuum* plants further comprise one or more QTLs associated with resistance to *Phytophthora*, wherein the QTLs map to a linkage group of LG2 or LG6.

In some embodiments, the QTL associated with resistance to *Phytophthora* from LG1/8 is genetically linked to a molecular marker. In some embodiment, the molecular marker is CAMS117 or CP10061. In some embodiments, CAMS117 can be identified by amplification product of primers CAMS117-F and CAMS117-R, and CP10061 can be identified by amplification product of primers CP10061-F and CP 10061-R.

In some embodiments, the QTL associated with resistance to *Phytophthora* from LG3 is genetically linked to a molecular marker. In some embodiments, the molecular marker is CA517699. In some embodiments, CA517699 can be identified by amplification product of primers CA517699-F and CA517699-R.

In some embodiments, the QTL associated with resistance to *Phytophthora* from LG5 is genetically linked to a molecular marker. In some embodiments, the molecular marker is CAMS420, CAMS190, or Epms749. In some embodiments, CAMS420 can be identified by amplification product of primers CAMS420-F and CAMS420-R; CAMS190 can be identified by amplification product of primers CAMS190-F and CAMS190-R; and Epms749 can be identified by amplification product of primers Epms749-F and Epms749-R.

In some embodiments, the QTL associated with resistance to *Phytophthora* from LG10 is genetically linked to a molecular marker. In some embodiments, the molecular marker is CAMS460. In some embodiments, CAMS460 can be identified by amplification product of primers CAMS460-F and CAMS460-R.

In some embodiments, the QTL associated with resistance to *Phytophthora* from LG2 is genetically linked to a molecular marker. In some embodiments, the molecular marker is HpmsE090 or EPMS709. In some embodiments, HpmsE090 can be identified by amplification product of primers HpmsE090-F and HpmsE090-R; and EPMS709 can be identified by amplification product of primers EPMS709-F and EPMS709-R.

In some embodiments, the QTL associated with resistance to *Phytophthora* from LG6 is genetically linked to a molecular marker. In some embodiments, the molecular marker is AF208834. In some embodiments, AF208834 can be identified by amplification product of primers AF208834-F and AF208834-R.

In some further embodiments, amplification products from the *Capsicum annuum* plants resistant to *Phytophthora* using primer pairs CAMS117-F and CAMS117-R, CA517699-F and CA517699-R, CAMS420-F and CAMS420-R, and CAMS460-F and CAMS460-R, are distinctive by size from amplification products by using the same pair of primers from a check *Capsicum annuum* line, wherein the check *Capsicum annuum* line has a *Phytophthora* resistance score of 3 to 5 based on a stem decapitation test using a virulent *P. capsici* isolate. In some embodiments, the virulent isolate is '1Z2, N 101', 'Italie 07', 'Californie 1-07', 'New Jersey', 'Californie 2-07', 'Floride 07', 'France 07', 'Mexique '07', 'S197', 'Mexique 2-07', 'France 2-09', or 'Shandong 09'. In some embodiments, the check *Capsicum annuum* line is Alzon, Aristotle, Alliance, JD, Paladin, Revolution, Yolo jaune, Zenel, or 07SRTC1802.

In some embodiments, the *Capsicum annuum* plants of the present invention have a level of resistance to *P. capsici* isolate 'S197' which is at least higher to the level of resistance of a susceptible check line. In some embodiments, the susceptible check line is selected from the group consisting of Alliance, Aristotle, and Revolution. In some embodiments, the *Capsicum annuum* plants of the present invention comprise QTL genetically linked to the molecular marker AF208834, wherein the marker AF208834 can be identified by amplification product of primers AF208834-F and AF208834-R. In some embodiments, the amplification product comprises about 228 nucleic acid base pairs. In some further embodiments, the plant has a *Phytophthora* resistance score of 0 based on the stem decapitation test using *P. capsici* isolate 'S197' and a rating score of 0 to 5. In some other embodiments, the amplification product comprises about 224 nucleic acid base pairs.

In some further embodiments, the plant has a *Phytophthora* resistance score of 1 or 2 based on the stem decapitation test using *P. capsici* isolate 'S197' and a rating score of 0 to 5.

In some embodiments, the *Capsicum annuum* plants resistant to *Phytophthora* of the present invention comprises one or more QTLs associated with fruit shape and/or fruit weight, wherein the QTLs associated with fruit shape and/or fruit weight map to linkage groups LG2, LG3, LG1/8, and/or LG10.

In some embodiments, the QTL associated with fruit shape and/or fruit weight is located in LG2, and is genetically linked to molecular marker PAPR2. In some embodiments, PAPR2 can be identified by amplification product of primers PAPR2-F and PAPR2-R.

In some embodiments, the QTL associated with fruit shape and/or fruit weight is located in LG3, and is genetically linked to molecular marker EPMS648. In some embodiments, EPMS648 can be identified by amplification product of primers EPMS648-F and EPMS648-R. In some embodiments, the amplification product comprises about 188 nucleic acid base pairs and the plant has the ¾th long fruit shape. In some other embodiments, the amplification product comprises about 186 nucleic acid base pairs and the plant has blocky fruit shape or half long fruit shape.

In some embodiments, the QTL associated with fruit shape and/or fruit weight is located in LG1/8, and is genetically linked to molecular marker HpmsMADS. In some embodiments, HpmsMADS can be identified by amplification product of primers HpmsMADS-F and HpmsMADS-R, In some embodiments, the QTL associated with fruit shape and/or fruit weight is located in LG10, and is genetically linked to molecular marker GPMS159. In some embodiments, GPMS159 can be identified by amplification product of primers GPMS159-F and GPMS159-R.

In some embodiments, the *Phytophthora* resistant *Capsicum annuum* plant of the present invention is '09SRTF712-4', '09SRTF713-5', '09SRTF776-4', '09SRTF788-1' or '09SRTF737-4' or their progenies. For example, the *Phytophthora* resistant *Capsicum annuum* plant is '09SRTF713-5', '09SRTF776-4', or '09SRTF788-1', a representative sample of seed for each of the plants mentioned herein has been deposited with NCIMB under No 41791, 41792 and 41793, respectively.

The present invention also provides a plant part, a plant cell, a plant population, and/or a plant progeny obtained by growing the *Phytophthora* resistant *Capsicum annuum* plants of the present invention. In some embodiments, the plant part is a seed, a fruit, a scion, and/or a rootstock. In some embodiments, the plant part is an ovule and/or pollen.

The present invention also provides plants having all of the physiological and morphological characteristics of the *Phytophthora* resistant *Capsicum annuum* plants of the present invention. For example, plants having all of the physiological and morphological characteristics of '09SRTF712-4', '09SRTF713-5', '09SRTF776-4', '09SRTF788-1' or '09SRTF737-4' can be obtained.

The present invention also provides tissue cultures of regenerable cells produced from the *Phytophthora* resistant *Capsicum annuum* plants of the present invention.

The present invention also provides methods for producing *Capsicum annuum* seed. In some embodiments, the methods comprise crossing the *Phytophthora* resistant *Capsicum annuum* plant of the present invention with itself or another *Capsicum annuum* plant, and harvesting the resultant seed. In some embodiments, a plant grown from the said seed comprises QTLs associated with resistance to *Phytophthora*, wherein the QTLs are genetically linked to molecular markers CAMS117, CAMS420, CA517699 and CAMS460 respectively, and wherein said plant having a blocky type, a ¾ long type, or a half long type fruit shape. The present invention also provides the progenies of such seeds and plants, comprising QTLs associated with resistance to *Phytophthora*, wherein the QTLs are genetically linked to molecular markers CAMS117, CAMS420, CA517699 and CAMS460 respectively, and wherein said plant have a blocky type, a ¾ long type, or a half long type fruit shape.

The present invention also provides methods for selecting a *Phytophthora* resistant *Capsicum annuum* plant having a blocky type, a ¾ long type, or a half long type fruit shape. In some embodiments, said methods comprise the steps of:

(i) detecting the presence of one or more QTLs associated with resistance to *Phytophthora* as indicated by the presence of one or more molecular markers selected from CAMS117, CP10061, CA517699, CAMS420, CAMS190, Epms749, CAMS460, wherein the QTLs are genetically linked to one of more said molecular markers;

(ii) detecting the presence of one or more QTLs associated with fruit shape and/or fruit weight as indicated by the presence of one or more molecular markers selected from PAPR2, EPMS648, HpmsMADS, GPMS159, wherein the QTLs are genetically linked to one of more said molecular markers;

(iii) selecting the plant comprising QTLs associated with resistance to *Phytophthora* from linkage groups LG1/8, LG3, LG5, LG10, and QTLs associated with fruit shape and/or fruit weight from linkage groups LG2, LG3, LG1/8, and/or LG10.

(iv) optionally, confirming resistance to *Phytophthora* in the plant of step (iii) based on a stem decapitation test, wherein the plant has a *Phytophthora* resistance score of 0 to 2. In some embodiments, the *P. capsici* isolate used in the stem decapitation test is '1Z2, N 101', 'Italie 07', 'Californie 1-07', 'New Jersey', 'Californie 2-07', 'Floride 07', 'France 07', 'Mexique '07', 'S197', 'Mexique 2-07', 'France 2-09', or 'Shandong 09'.

In some embodiments, the methods further comprise steps of: (i) detecting the presence of one or more QTLs associated with resistance to *Phytophthora* as indicated by the presence of one or more molecular markers selected from HpmsE090, EPMS709, and AF208834, wherein the QTLs are genetically linked to one of more said molecular markers; (ii) selecting the plant comprising QTLs associated with resistance to *Phytophthora* from linkage groups LG2 and/or LG6.

In some embodiments, the molecular marker CAMS117 is defined by amplification product of primers CAMS117-F and CAMS117-R, the molecular marker CP 10061 is defined by amplification product of primers CP10061-F and CP 10061-R, the molecular marker CA517699 is defined by amplification product of primers CA517699-F and CA517699-R, the molecular marker CAMS420 is defined by amplification product of primers CAMS420-F and CAMS420-R, the molecular marker CAMS190 is defined by amplification product of primers CAMS190-F and CAMS190-R, the molecular marker Epms749 is defined by amplification product of primers Epms749-F and Epms749-R, the molecular marker CAMS460 is defined by amplification product of primers CAMS460-F and CAMS460-R, the molecular marker HpmsE090 is defined by amplification product of primers HpmsE090-F and HpmsE090-R, the molecular marker EPMS709 is defined by amplification product of primers EPMS709-F and EPMS709-R, and the molecular marker AF208834 is defined by amplification product of primers AF208834-F and AF208834-R. In some further embodiments, the amplification product by using primers CAMS117-F and CAMS117-R, primers CP10061-F and CP 10061-R, CA517699-F and CA517699-R, CAMS420-F and CAMS420-R, CAMS190-F and CAMS190-R, Epms749-F and Epms749-R, CAMS460-F and CAMS460-R, HpmsE090-F and HpmsE090-R, EPMS709-F and EPMS709-R, and/or AF208834-F and AF208834-R from the *Capsicum annuum* plant resistant to *Phytophthora* is distinctive by size from an amplification product by using the same pair of primers from a check *Capsicum annuum* line, wherein the check *Capsicum annuum* line has a *Phytophthora* resistance score of 3 to 5 based on a stem decapitation test. In some embodiments, the *P. capsici* isolate used in the test is 'S197'.

BRIEF DESCRIPTION OF THE DRAWINGS

FIG. 1 depicts *Capsicum* species classification constructed from standard genetic distance estimates based on isozyme data compared with a classification based on flower color (adopted from McLeod et al., 2001).

FIG. 2 depicts a summary of *Capsicum*-hybrid crossing studies (adopted from McLeod et al., 2001).

FIG. 3 depicts a non-limiting example of a breeding scheme for gene pyramiding.

FIG. 4 depicts a schematic map of QTLs linked to *P. capsici* resistance (in purple) and agronomical QTL (in green). Arrows indicate the size of the QTL interval; fs=fruit shape; fw=fruit weight; and names of markers are shown in black text.

FIG. 5 depicts pepper plants with *P. capsici* resistance QTLs derived from 'CM334' and QTLs of agronomic traits related to fruit shape and fruit weight derived from '07SRTC1802'. Lines '09SRTF712-4' and '09SRTF713-5' have rectangular ¼ long type fruit; while lines '09SRTF737-4', '09SRTF776-4' have blocky type fruit and line '09SRTF788-1' has half long type fruit.

FIG. 6 depicts non-limiting examples of blocky type pepper, half long type pepper, and ¾ long type pepper. For blocky type pepper (FIG. 6A), the length of the fruit is about the same as the width of the fruit; for half long type pepper (FIG. 6B), the length of the fruit is about 1.2 to 1.5 the width of the fruit; for ¾ long type pepper (FIG. 6C), also often referred as lamuyo type pepper, the length of the fruit is more than about 1.5 the width of the fruit.

SEQUENCES

Description of the Text File Submitted Electronically

The contents of the text file submitted electronically are incorporated herein by reference in their entirety: A computer readable format copy of the Sequence Listing (filename: VILM-003-00US_ST25.txt, date recorded: Feb. 25, 2011, file size 6 kilobyte).

DETAILED DESCRIPTION

All publications, patents and patent applications, including any drawings and appendices, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

DEFINITIONS

As used herein, the verb "comprise" as is used in this description and in the claims and its conjugations are used in its non-limiting sense to mean that items following the word are included, but items not specifically mentioned are not excluded.

As used herein, the term "plant" refers to any living organism belonging to the kingdom Plantae (i.e., any genus/species in the Plant Kingdom).

As used herein, the term "plant part" refers to any part of a plant including but not limited to the shoot, root, stem, seeds, fruits, stipules, leaves, petals, flowers, ovules, bracts, branches, petioles, internodes, bark, pubescence, tillers, rhizomes, fronds, blades, pollen, stamen, rootstock, scion and the like. The two main parts of plants grown in some sort of media, such as soil, are often referred to as the "above-ground" part, also often referred to as the "shoots", and the "below-ground" part, also often referred to as the "roots".

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T en G/C content) of primer. A pair of bi-directional primers consists of one forward and one reverse primer as commonly used in the art of DNA amplification such as in PCR amplification.

As used herein, the term "resistant", or "resistance", describes a plant, line or cultivar that shows fewer or reduced symptoms to a biotic pest or pathogen than a susceptible (or more susceptible) plant, line or variety to that biotic pest or pathogen. These terms are variously applied to describe plants that show no symptoms as well as plants showing some symptoms but that are still able to produce marketable product with an acceptable yield. Some lines that are referred to as resistant are only so in the sense that they may still produce a crop, even though the plants may appear visually stunted and the yield is reduced compared to uninfected plants. As defined by the International Seed Federation (ISF), a non-governmental, non-profit organization representing the seed industry (see "Definition of the Terms Describing the Reaction of Plants to Pests or Pathogens and to Abiotic Stresses for the Vegetable Seed Industry", May 2005), the recognition of whether a plant is affected by or subject to a pest or pathogen can depend on the analytical method employed. Resistance is defined by the ISF as the ability of a plant types to restrict the growth and development of a specified pest or pathogen and/or the damage they cause when compared to susceptible plant varieties under similar environmental conditions and pest or pathogen pressure. Resistant plant types may still exhibit some disease symptoms or damage. Two levels of resistance are defined. The term "high/standard resistance" is used for plant varieties that highly restrict the growth and development of the specified pest or pathogen under normal pest or pathogen pressure when compared to susceptible varieties. "Moderate/intermediate resistance" is applied to plant types that restrict the growth and development of the specified pest or pathogen, but exhibit a greater range of symptoms or damage compared to plant types with high resistance. Plant types with intermediate resistance will show less severe symptoms than susceptible plant varieties, when grown under similar field conditions and pathogen pressure. Methods of evaluating resistance are well known to one skilled in the art. Such evaluation may be performed by visual observation of a plant or a plant part (e.g., leaves, roots, flowers, fruits et. al) in determining the severity of symptoms. For example, when each plant is given a resistance score on a scale of 1 to 5 based on the severity of the reaction or symptoms, with 1 being the resistance score applied to the most resistant plants (e.g., no symptoms, or with the least symptoms), and 5 the score applied to the plants with the most severe symptoms, then a line is rated as being resistant when at least 75% of the plants have a resistance score at a 1, 2, or 3 level, while susceptible lines are those having more than 25% of the plants scoring at a 4 or 5 level. If a more detailed visual evaluation is possible, then one can use a scale from 1 to 10 so as to broaden out the range of scores and thereby hopefully provide a greater scoring spread among the plants being evaluated.

An alternative resistance score might be used, for example by focusing on certain leaf symptoms: such as where 0 stands for no leaves on a plant showing necrosis after infection, 1 stands for from 0-1 leaves showing necrosis after infection, 2 stands for 1-2 leaves showing necrosis after infection, 3 stands for 2-3 leaves showing necrosis after infection, and 4 stands for 3-4 leaves showing necrosis after infection. A line is rated as being resistant when at least 75% of the plants have a resistance score at level 0, 1, or 2; while susceptible lines are those having more than 25% of the plants scoring at level 3 or 4.

Another scoring system is a root inoculation test based on the development of the necrosis after inoculation and its position towards the cotyledon (such as one derived from Bosland et al., 1991), wherein 0 stands for no symptom after infection; 1 stands for a small necrosis at the hypocotyl after infection; 2 stands a necrosis under the cotyledons after infection; 3 stands for necrosis above the cotyledons after infection; 4 stands for a necrosis above the cotyledons together with a wilt of the plant after infection, while eventually, 5 stands for a dead plant.

In addition to such visual evaluations, disease evaluations can be performed by determining the pathogen bio-density in a plant or plant part using electron microscopy and/or through molecular biological methods, such as protein hybridization (e.g., ELISA, measuring pathogen protein density) and/or nucleic acid hybridization (e.g., RT-PCR, measuring pathogen RNA density). Depending on the particular pathogen/plant combination, a plant may be determined resistant to the pathogen, for example, if it has a pathogen RNA/DNA and/or protein density that is about 50%, or about 40%, or about 30%, or about 20%, or about 10%, or about 5%, or about 2%, or about 1%, or about 0.1%, or about 0.01%, or about 0.001%, or about 0.0001% of the RNA/DNA and/or protein density in a susceptible plant.

As used herein, the term "full resistance" is referred to as complete failure of the pathogen to develop after infection, and may either be the result of failure of the pathogen to enter the cell (no initial infection) or may be the result of failure of the pathogen to multiply in the cell and infect subsequent cells (no subliminal infection, no spread). The presence of full resistance may be determined by establishing the absence of pathogen protein or pathogen RNA in cells of the plant, as well as the absence of any disease symptoms in said plant, upon exposure of said plant to an infective dosage of pathogen (i.e. after 'infection'). Among breeders, this phenotype is often referred to as "immune". "Immunity" as used herein thus refers to a form of resistance characterized by absence of pathogen replication even when the pathogen is actively transferred into cells by e.g. electroporation.

As used herein, the term "partial resistance" is referred to as reduced multiplication of the pathogen in the cell, as reduced (systemic) movement of the pathogen, and/or as reduced symptom development after infection. The presence of partial resistance may be determined by establishing the systemic presence of low concentration of pathogen protein or pathogen RNA in the plant and the presence of decreased or delayed disease-symptoms in said plant upon exposure of said plant to an infective dosage of pathogen. Protein concentration may be determined by using a quantitative detection method (e.g. an ELISA method or a quantitative reverse transcriptase-polymerase chain reaction (RT-PCR)). Among breeders, this phenotype is often referred to as "intermediate resistant."

As used herein, the term "tolerant" is used herein to indicate a phenotype of a plant wherein disease-symptoms remain absent upon exposure of said plant to an infective dosage of pathogen, whereby the presence of a systemic or local pathogen infection, pathogen multiplication, at least the presence of pathogen genomic sequences in cells of said plant and/or genomic integration thereof can be established. Tolerant plants are therefore resistant for symptom expression but symptomless carriers of the pathogen. Sometimes, pathogen sequences may be present or even multiply in plants without causing disease symptoms. This phenomenon is also known as "latent infection". In latent infections, the pathogen may exist in a truly latent non-infectious occult form, possibly as an integrated genome or an episomal agent (so that pathogen protein cannot be found in the cytoplasm, while PCR protocols may indicate the present of pathogen nucleic acid sequences) or as an infectious and continuously replicating agent. A reactivated pathogen may spread and initiate an epidemic among susceptible contacts. The presence of a "latent infection" is indistinguishable from the presence of a "tolerant" phenotype in a plant.

As used herein, the term "susceptible" is used herein to refer to a plant having no or virtually no resistance to the pathogen resulting in entry of the pathogen into the plant and multiplication and systemic spread of the pathogen, resulting in disease symptoms. The term "susceptible" is therefore equivalent to "non-resistant".

As used herein the term "*Phytophthora*-resistant," is to be interpreted as referring to the resistance of a plant, plant tissue, or plant cell, in particular a *Capsicum*, to the establishment of an infection, or the establishment of *Phytophthora* sp., e.g., *Phytophthora capsici*.

As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the terms "dicotyledon" and "dicot" refer to a flowering plant having an embryo containing two seed halves or cotyledons. Examples include tobacco; tomato; the legumes, including peas, alfalfa, clover and soybeans; oaks; maples; roses; mints; squashes; daisies; walnuts; cacti; violets and buttercups.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the term "heterozygote" refers to a diploid or polyploid individual cell or plant having different alleles (forms of a given gene) present at least at one locus. As used herein, the term "heterozygous" refers to the presence of different alleles (forms of a given gene) at a particular gene locus.

As used herein, the terms "homolog" or "homologue" refer to a nucleic acid or peptide sequence which has a common origin and functions similarly to a nucleic acid or peptide sequence from another species.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "inbred" or "inbred line" refers to a relatively true-breeding strain.

The term "single allele converted plant" as used herein refers to those plants which are developed by a plant breeding technique called backcrossing wherein essentially all of the desired morphological and physiological characteristics of an inbred are recovered in addition to the single allele transferred into the inbred via the backcrossing technique.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the term "locus" (plural: "loci") refers to any site that has been defined genetically. A locus may be a gene, or part of a gene, or a DNA sequence that has some regulatory role, and may be occupied by different sequences.

As used herein, the terms "introgression", "introgressed" and "introgressing" refer to the process whereby genes of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

As used herein, the term "population" means a genetically homogeneous or heterogeneous collection of plants sharing a common genetic derivation.

As used herein, the term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present invention relates to QTLs, i.e. genomic regions that may comprise one or more genes or regulatory sequences, it is in some instances more accurate to refer to "haplotype" (i.e. an allele of a chromosomal segment) in stead of "allele", however, in those instances, the term "allele" should be understood to comprise the term "haplotype". Alleles are considered identical when they express a similar phenotype. Differences in sequence are possible but not important as long as they do not influence phenotype.

As used herein, the term "mass selection" refers to a form of selection in which individual plants are selected and the next generation propagated from the aggregate of their seeds. More details of mass selection are described herein in the specification.

As used herein, the term "monocotyledon" or "monocot" refer to any of a subclass (Monocotyledoneae) of flowering plants having an embryo containing only one seed leaf and usually having parallel-veined leaves, flower parts in multiples of three, and no secondary growth in stems and roots. Examples include lilies; orchids; rice; corn, grasses, such as tall fescue, goat grass, and Kentucky bluegrass; grains, such as wheat, oats and barley; irises; onions and palms.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein when discussing plants, the term "ovule" refers to the female gametophyte, whereas the term "pollen" means the male gametophyte.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "self-crossing", "self pollinated" or "self-pollination" means the pollen of one flower on one plant is applied (artificially or naturally) to the ovule (stigma) of the same or a different flower on the same plant.

As used herein, the term "shoulder" refers to the portion of the pepper fruit where the area around the stem begins to drop-off to the sides of the fruit. It is the area forming the angle between the top of the fruit and the sides of the fruit.

As used herein, the terms "Quantitative Trait Loci" and "QTL" are used herein in their art-recognized meaning. A QTL may for instance comprise one or more genes of which the products confer the genetic resistance. Alternatively, a QTL may for instance comprise regulatory genes or sequences of which the products influence the expression of genes on other loci in the genome of the plant thereby conferring the resistance. The QTLs of the present invention may be defined by indicating their genetic location in the genome of the respective pathogen-resistant accession using one or more molecular genomic markers. One or more markers, in turn, indicate a specific locus. Distances between loci are usually measured by frequency of crossing-over between loci on the same chromosome. The farther apart two loci are, the more likely that a crossover will occur between them. Conversely, if two loci are close together, a crossover is less likely to occur between them. As a rule, one centimorgan (cM) is equal to 1% recombination between loci (markers). When a QTL can be indicated by multiple markers the genetic distance between the end-point markers is indicative of the size of the QTL.

As used herein, the term "molecular marker" or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Mapping of molecular markers in the vicinity of an allele is a procedure which can be performed quite easily by the average person skilled molecular-biological techniques which techniques are for instance described in Lefebvre and Chevre, 1995; Lorez and Wenzel, 2007, Srivastava and Narula, 2004, Meksem and Kahl, 2005, Phillips and Vasil, 2001. General information concerning AFLP technology can be found in Vos et al. (1995, AFLP: a new technique for DNA fingerprinting, Nucleic Acids Res. 1995 Nov. 11; 23(21): 4407-4414).

Plant Diseases Resistance

Plant disease resistance derives both from pre-formed defenses and from infection-induced responses mediated by the plant immune system. Disease outcome is determined by the three-way interaction of the pathogen, the plant, and the environmental conditions (an interaction known as the disease triangle). Defense-activating compounds can move cellto-cell and systemically through the plant vascular system, but plants do not have circulating immune cells so most cell types in plants retain the capacity to express a broad suite of antimicrobial defenses. Although obvious qualitative differences in disease resistance can be observed when some plants are compared (allowing classification as "resistant" or "susceptible" after infection by the same pathogen strain at similar pathogen pressure in similar environments), a gradation of quantitative differences in disease resistance is more typically observed between plant lines or genotypes.

Preformed structures and compounds that contribute to resistance in plants include, but are not limited to, plant cuticle/surface, plant cell walls, antimicrobial chemicals (e.g., glucosides, saponins), antimicrobial proteins, enzyme inhibitors, detoxifying enzymes that break down pathogen-derived toxins, receptors that perceive pathogen presence and active inducible plant defenses. Inducible plant defenses that are generated upon or after infection include, but are not limited to, cell wall reinforcement (e.g., increased callose, lignin, suberin, cell wall proteins), antimicrobial chemicals (e.g., reactive oxygen species such as hydrogen peroxide, peroxynitrite, or complex phytoalexins such as genistein or camalexin), antimicrobial proteins (e.g., defensins, thionins, or pathogenesis-related (PR) proteins), antimicrobial enzymes (e.g., chitinases, beta-glucanases, peroxidases), hypersensitive response (e.g., rapid host cell death response associated with defense mediated by resistance genes), and post-translation gene silencing.

Plant immune systems show some mechanistic similarities and apparent common origin with the immune systems of insects and mammals, but also exhibit many plant-specific characteristics. As in most cellular responses to the environment, defenses are activated when receptor proteins directly or indirectly detect pathogen presence and trigger ion channel gating, oxidative burst, cellular redox changes, protein kinase cascades, and/or other responses that either directly activate cellular changes (such as cell wall reinforcement), or activate changes in gene expression that then elevate plant defense responses.

Plants, like animals, have a basal immune system that includes a small number of pattern recognition receptors that are specific for broadly conserved microbe-associated molecular patterns (MAMPs, also called pathogen-associated molecular patterns or PAMPs). Examples of these microbial compounds that elicit plant basal defense include bacterial flagellin or lipopolysaccharides, or fungal chitin. The defenses induced by MAMP perception are sufficient to repel most potentially pathogenic microorganisms. However, pathogens express effector proteins that are adapted to allow them to infect certain plant species; these effectors often enhance pathogen virulence by suppressing basal host defenses.

Importantly, plants have evolved R genes (resistance genes) whose products allow recognition of specific pathogen effectors, either through direct binding of the effector or by recognition of the alteration that the effector has caused to a host protein. R gene products control a broad set of disease resistance responses whose induction is often sufficiently rapid and strong to stop adapted pathogens from further growth or spread. Plant genomes each contain a few hundred apparent R genes, and the R genes studied to date usually confer specificity for particular strains of a pathogen species. As first noted by Harold Flor in the mid-20th century in his formulation of the gene-for-gene relationship, the plant R gene and the pathogen "avirulence gene" (effector gene) must have matched specificity for that R gene to confer resistance. The presence of an R gene can place significant selective pressure on the pathogen to alter or delete the corresponding avirulence/effector gene. Some R genes show evidence of high stability over millions of years while other R genes, especially those that occur in small clusters of similar genes, can evolve new pathogen specificities over much shorter time periods.

The use of receptors carrying leucine-rich repeat (LRR) pathogen recognition specificity domains is common to plant, insect, jawless vertebrate and mammal immune systems, as is the presence of Toll/Interleukin receptor (TIR) domains in many of these receptors, and the expression of defensins, thionins, oxidative burst and other defense responses (Jones and Dangl. 2006 The plant immune system. *Nature* 444:323-329. Ting et al. 2008. NLRs at the intersection of cell death and immunity. *Nat Rev Immunol.* 8:372-379. which are incorporated herein by reference in their entireties).

Some of the key endogenous chemical mediators of plant defense signal transduction include salicylic acid, jasmonic acid or jasmonate, ethylene, reactive oxygen species, and nitric oxide. Numerous genes and/or proteins have been identified that mediate plant defense signal transduction (Hammond-Kosack and Parker, 2003, Deciphering plant-pathogen communication: fresh perspectives for molecular resistance breeding. *Curr. Opin. Biotechnol.* 14:177-193). Cytoskeleton and vesicle trafficking dynamics help to target plant defense responses asymmetrically within plant cells, toward the point of pathogen attack.

Plant immune systems can also respond to an initial infection in one part of the plant by physiologically elevating the capacity for a successful defense response in other parts of the plant. These responses include systemic acquired resistance, largely mediated by salicylic acid-dependent pathways, and induced systemic resistance, largely mediated by jasmonic acid-dependent pathways. Against viruses, plants often induce pathogen-specific gene silencing mechanisms mediated by RNA interference. These are primitive forms of adaptive immunity.

In a small number of cases, plant genes have been identified that are broadly effective against an entire pathogen species (against a microbial species that is pathogenic on other genotypes of that host species). Examples include barley MLO against powdery mildew, wheat Lr34 against leaf rust, and wheat Yr36 against stripe rust. An array of mechanisms for this type of resistance may exist depending on the particular gene and plant-pathogen combination. Other reasons for effective plant immunity can include a relatively complete lack of co-adaptation (the pathogen and/or plant lack multiple mechanisms needed for colonization and growth within that host species), or a particularly effective suite of pre-formed defenses.

Resistance to disease varies among plants. It may be either total (a plant is immune to a specific pathogen) or partial (a plant is tolerant to a pathogen, suffering minimal injury). The two broad categories of resistance to plant diseases are vertical (specific) and horizontal (nonspecific). A plant variety that exhibits a high degree of resistance to a single race, or strain, of a pathogen is said to be vertically resistant; this ability usually is controlled by one or a few plant genes. Horizontal resistance, on the other hand, protects plant varieties against several strains of a pathogen, although the protection is not as complete. Horizontal resistance is more common and involves at least several or many genes. Resistance might occur at the sub-specific or varietal level (race or cultivar-specific resistance, likely mediated by single resistance (R) gene) or at the species or genus level (nonhost resistance). In addition, resistance might be a quantitative phenotype (partial resistance) with a partial reduction in disease severity.

Race or cultivar-specific resistance, likely mediated by single resistance (R) gene, is thought to be of limited value in the field, because of the rapid evolution of new virulent races of the pathogens. On the other hand, nonhost and partial resistance appear more durable. However, the extent to which durable nonhost or partial resistance involves genetic components that are distinct from R genes remains unclear.

Several means of obtaining disease-resistant plants are commonly employed alone or in combination. These include, but are not limited to, introduction from an outside source, selection, and induced variation. All three may be used at different stages in a continuous process; for example, varieties free from injurious insects or plant diseases may be introduced for comparison with local varieties. The more promising lines or strains are then selected for further propagation, and they are further improved by promoting as much variation as possible through hybridization or special treatment. Finally, selection of the plants showing greatest promise takes place.

Methods used in breeding plants for disease resistance are similar to those used in breeding for other characters. It is necessary to know as much as possible about the nature of inheritance of the resistant characters in the host plant and the existence of physiological races or strains of the pathogen.

Plant Resistance to Oomycetes

Oomycete plant pathogens, such as *Phytophthora*, downy mildews and Pythium, have devastating disease effects on numerous crop and ornamental plants. Various types of genetic resistance to oomycetes occur in plants, and can be determined at the sub-specific or varietal level (race or cultivar-specific resistance), or at the species or genus level (nonhost resistance). In addition, resistance might be a quantitative phenotype (partial resistance). Resistance reactions are often associated with the hypersensitive response—a programmed cell death pathway. Recent advances in the genetic, biochemical and cytological characterization of disease resistance suggests that the hypersensitive response is associated with all forms of resistance to *Phytophthora* and downy mildews. Identification of the resistance genes involved in nonhost and partial resistance to oomycetes remains an important challenge.

The infection of oomycete pathogens starts when zoospores (motile spores) encyst and germinate on root or leaf surface. In some species, sporangia (asexual spores) might germinate directly. Germ tubes penetrate an epidermal cell to form an infection vesicle. In susceptible plants, branching hyphae with feeding structures known as haustoria, expand from the site of penetration to neighboring cells through the intercellular space. In resistant plants, the major defense reaction is the HR. The timing and extent of the HR varies depending on the interacting pathogen and plant genotypes. In some cases, such as with many nonhost interactions, the HR remains limited to one or a few cells. In other cases, such as *P. infestans* infection of resistant potato cultivars carrying the *Solanum demissum* R genes, or potato cultivars with high resistance levels, a group of cells display the HR and the infection is stopped at a later stage. Interactions displaying partial resistance are sometimes also associated with HR lesions. In these cases, the HR appears ineffective in blocking the pathogen, resulting in numerous escaping hyphae and a typical phenotype of trailing HR, in which the pathogen hyphae remain ahead of the plant response.

A number of R genes against the downy mildews *Peronospora parasitica* and *Bremia lactucae* have been isolated (Parker, J. E. et al. (1997) Plant Cell 9, 879-894; Botella, M. A. et al. (1998) Plant Cell 10, 1847-1860; McDowell, J. M. et al. (1998) Plant Cell 10, 1861-1874; and Meyers, B. C. et al. (1998) Plant Cell 10, 1833-1846). All identified genes encode receptor-like proteins that contain a nucleotide binding site and several leucine-rich-repeats (LRR). This structure is typical of R genes active against other pathogens. At least three classes of R proteins targeted against oomycetes are known, and are distinguished by their N-terminal regions, which show homology to the TIR domain (RPP 1 and RPP5 clusters), leucine-zipper motifs (RPP8 cluster) or have no obvious homology to known domains (Dm3 cluster). Resistance mediated by R genes in Arabidopsis and lettuce is always associated with the HR, which is generally visible as a distinct necrosis and correlates with the accumulation of autofluorescent compounds and irreversible membrane damage. The extent, timing and severity of the HR may vary depending on the R gene examined and the pathogen strain.

Partial resistance in plants to several oomycetes has been observed and studied. For example, partial resistance to two races of *P. infestans* was found to segregate in a cross between non-inbred diploid potato lines. Quantitative trait loci (QTLs) contributing to resistance to late blight have been identified. Two of these loci correspond to regions of the genome that contain clusters of known R genes and R gene analogs, raising the possibility that these QTLs might represent genes homologous to typical R genes.

Oomycetes

Oomycetes is a class of Oomycota, which is a phylum of filamentous protists, containing over around 70 genera and more than 800 known species (J. W. Deacon *Modern mycology* Edition: 3, Published by Wiley-Blackwell, 1997 ISBN 0632030771, 9780632030774).

"Oomycota" means "egg fungi", referring to the oversize oogonia which house the female gametes (eggs). Despite the name and their superficial appearance, oomycetes are not fungi. They are unicellular heterokonts, physically resembling fungi. Oomycetes are commonly known as water molds (or water moulds) or downy mildew. They are microscopic, absorptive organisms that reproduce both sexually and asexually and are composed of mycelia, or a tube-like vegetative body (all of an organism's mycelia are called thallus).

Oomycete cells differ from those of true fungi in that they have walls of cellulose and the amino acid hydroxyproline. They are heterotophic, either saphropytic or parasitic. The principle cell wall of oomycetes is not composed of chitin, as in the fungi, but is made up of a mix of cellulosic compounds and glycan. The nuclei within the filaments are diploid, with two sets of genetic information, not haploid as in the fungi.

Oomycetes do not synthesize sterols. They have cillia (small hairlike structures) that help it eat and move around. Among the oomycetes, these are produced as asexual spores called zoospores, which are released from sporangium and capitalize on surface water (including precipitation on plant surfaces) for movement. Oomycetes may also germinate directly on the host plant by way of a germ tube. They also produce sexual spores, called oospores, that are translucent double-walled spherical structures used to survive adverse environmental conditions. This type of reproduction is known as "gametangical copulation".

A few produce aerial asexual spores that are distributed by wind.

The water molds are economically and scientifically important because they are aggressive plant pathogens. The majority can be broken down into three groups, although more exist.

The *Phytophthora* group is a genus that causes diseases such as dieback, late blight in potatoes, sudden oak death, rhododendron root rot, and ink disease in the American Chestnut.

The *Pythium* group is even more prevalent than *Phytophthora* and individual species have larger host ranges, usually causing less damage. *Pythium* damping off is a very common problem in greenhouses where the organism kills newly emerged seedlings. Mycoparasitic members of this group (e.g. *P. oligandrum*) parasitize other oomycetes and fungi, and have been employed as biocontrol agents. One *Pythium* species, *Pythium insidiosum* is also known to infect mammals.

The third group of oomycetes is the downy mildews, which are easily identifiable by the appearance of white "mildew" on leaf surfaces.

Oomycete-caused plant diseases include, but are not limited to, grape downy mildew (caused by *Plasmopara viticola*) and potato late blight (caused by *Phytophthora infestans*) and oomycete infestation of Arctotis (caused by *Bremia lactucae*), Chenopodium murale (caused by *Peronospora farinosa*), cucurbits and cucumbers (caused by *Pseudoperonospora cubensis*), grasses and grains (caused by *Sclerospora graminicola*), lettuce (caused by *Bremia lactucae*), onion (caused by *Peronospora destructor*), alfalfa (caused by *Peronospora trifoliorum*), lima bean (caused by *Phytophthora phaseoli*), sunflower (caused by *Plasmopara halstedii*), carrot (caused by *Plasmopara nivea*, also called *Plasmopara crustosa*), hops (caused by *Pseudoperonospora humuli*), crucifers (caused by *Peronospora parasitica*), spinach (caused by *Peronospora effitsa*), beet (caused by *Peronospora schachtii*, also called *Peronospora farinosa*), peas (caused by *Peronospora viciae*), rose (caused by *Peronospora sparsa*), poppy (caused by *Peronospora arborescens*), tobacco (caused by *Peronospora hyoscami*), and violet (caused by *Peronospora violae*).

Phytophthora

*Phytophthora* (from Greek phytón, "plant" and phthorá, "destruction"; "the plant-destroyer") is a genus of plant-damaging oomycetes (water molds), whose member species are capable of causing enormous economic losses on crops worldwide, as well as environmental damage in natural ecosystems. The genus was first described by Heinrich Anton de Bary in 1875.

*Phytophthora* spp. are mostly pathogens of dicotyledon plants, and are relatively host-specific parasites. Many species of *Phytophthora* are plant pathogens of considerable economic importance. For example, *Phytophthora infestans* is the infective agent of the potato blight that caused the Great Irish Famine (1845-1849), and still remains to be the most destructive pathogen of potato crops, and the soya bean root and stem rot agent. *Phytophthora sojae*, has also caused longstanding problems for the agricultural industry. In general, plant diseases caused by this genus are difficult to control chemically, and thus the growth of resistant cultivars is the main management strategy. Other important *Phytophthora* diseases including, but are not limited to, alder root rot (*Phytophthora alni*), rhododendron root rot affecting rhododendrons, azaleas and bleeding canker in hardwood trees (*Phytophthora cactorum*), Cucurbitaceae fruits diseases (*Phytophthora capsici*), cinnamon root rot affecting woody ornamentals including arborvitae, azalea, Chamaecyparis, dogwood, forsythia, Fraser fir, hemlock, Japanese holly, juniper, Pieris, rhododendron, Taxus, white pine, American chestnut and Australian Jarrah (*Phytophthora cinnamomi*), red root rot affecting strawberries (*Phytophthora fragariae*), fruit rot in coconuts and betel nuts (*Phytophthora palmivora*), infects over 60 plant genera and over 100 host species (*Phytophthora ramorum*), oak death (*Phytophthora quercina*), and soybean root rot (*Phytophthora sojae*).

*Phytophthora*s may reproduce sexually or asexually. In many species, sexual structures have never been observed, or have only been observed in laboratory matings. In homothallic species, sexual structures occur in single culture. Heterothallic species have mating strains, designated as A1 and A2. When mated, antheridia introduce gametes into oogonia, either by the oogonium passing through the antheridium (ainphigyny) or by the antheridium attaching to the proximal (lower) half of the oogonium (paragyny), and the union producing oospores. Like animals, but not like most true Fungi, meiosis is gametic, and somatic nuclei are diploid. Asexual (mitotic) spore types are chlamydospores, and sporangia which produce zoospores. Chlamydospores are usually spherical and pigmented, and may have a thickened cell wall to aid in its role as a survival structure. Sporangia may be retained by the subtending hyphae (non-caducous) or be shed readily by wind or water tension (caducous) acting as dispersal structures. Also, sporangia may release zoospores, which have two unlike flagella which they use to swim towards a host plant.

Non-limiting exemplary *Phytophthora* species include, *Phytophthora botryosa*, *Phytophthora brassicae*, *Phytophthora cactorum*, *Phytophthora cajani*, *Phytophthora cambivora*, *Phytophthora capsici*, *Phytophthora cinnamomi*, *Phytophthora citricola*, *Phytophthora citrophthora*, *Phytophthora clandestina*, *Phytophthora colocasiae*, *Phytophthora cryptogea*, *Phytophthora drechsleri*, *Phytophthora erythroseptica*, *Phytophthora fragariae*, *Phytophthora gonapodyides*, *Phytophthora heveae*, *Phytophthora, humicola*, *Phytophthora hydropathica*, *Phytophthora irrigata*, *Phytophthora idaei*, *Phytophthora ilicis*, *Phytophthora infestans*, *Phytophthora inflata*, *Phytophthora iranica*, *Phytophthora katsurae*, *Phytophthora lateralis*, *Phytophthora medicaginis*, *Phytophthora megakarya*, *Phytophthora megasperma*, *Phytophthora melonis*, *Phytophthora mirabilis*, *Phytophthora multivesiculata*, *Phytophthora nemorosa*, *Phytophthora nicotianae*, *Phytophthora palmivora*, *Phytophthora phaseoli*, *Phytophthora porri*, *Phytophthora primulae*, *Phytophthora pseudotsugae*, *Phytophthora quercina*, *Phytophthora ramorum*, *Phytophthora sinensis*, *Phytophthora sojae*, *Phytophthora syringae*, *Phytophthora tentaculata*, *Phytophthora trifolii*, *Phytophthora richardiae* and *Phytophthora vignae*. More *Phytophthora* species are described in Forster et al. (September 2000, Mycol. Res. 104 (9): 1055-1061), Erwin et al. (*Phytophthora*: its biology, taxonomy, ecology, and pathology, American Phytopathological Society, 1983), Ribeiro (A source book of the genus *Phytophthora*, J. Cramer, 1978), Lucas, (*Phytophthora*: Symposium of the British Mycological Society, the British Society for Plant Pathology, and the Society of Irish Plant Pathologists held at Trinity College, Dublin, September 1989, ISBN 0521400805, 9780521400800) and Tucker (The taxonomy of the genus *Phytophthora* de Bary, University of Missouri, 1931), each of which is hereby incorporated by reference in its entirety.

Phytophthora capsici

*Phytophthora capsici* can cause some of the most devastating field or greenhouse diseases of Solanaceae family worldwide, such as fruit rot, leaf spot and blight, collar rots and stem rots, and green wilt (see, Allagui et al., 1995, Agronomie, 15:171-179; Andres et al., 2003, J. plant Pathol. 85:91-98; and Verma et al., 2001, Indian. J. Agric. Sci. 71:219-221). It causes severe losses of pepper in the Southwestern U.S. and fruit rots (pepper, tomato, eggplant) in Florida. The fungus is reported from the Western hemisphere, Asia, and Europe. *Phytophthora capsici* is known to infect many species of pepper, tomato, and other members of the Solanaceae family.

The pathogen has reportedly caused severe epidemics in Central and South America, Europe, Asia, and many other states in the United States where susceptible vegetables are grown. The host range of *P. capsici* is wide and includes bell pepper, cacao, cantaloupe, chayote, cucumber, eggplant, honeydew melon, marigold, macadamia nut, papaya, pumpkin, some bean types, squash, tomato, and watermelon. Diseases caused by *P. capsici* are referred to as *Phytophthora* blight, *Phytophthora* crown and root rot, and *Phytophthora* fruit rot.

*Phytophthora capsici* causes seed rot and seedling blight in many Solanaceous crops (pepper, eggplant, tomato) and Cucurbits (cantaloupe, cucumber, summer squash, pumpkin, watermelon), similar to those seen with fungi, *Pythium* spp., and other *Phytophthora* spp. Rotting of seedlings prior to emergence (pre-emergence damping-off) and blighting of recently emerged seedlings (post-emergence damping-off) can occur. The roots and plant base may be discolored and infected seedlings often topple over. White fungal-like (mycelia) growth may cover infected areas of blighted seedlings under moist conditions. On mature plants, *P. capsici*, as well as other *Phytophthora* spp., can also produce a wide variety of symptoms that vary by host. Some bean types (broad, butter, lima, snap) can be susceptible to *P. capsici*. Symptoms on bean include water-soaked foliage, stem and pod necrosis, and white mycelia or sporulation on the plant surfaces.

In susceptible pepper, roots, stems, foliage, and fruit of mature plants can be infected. Although infection can occur at any height on stems, it is most common at the soil line, and starts as a dark, water-soaked area. Stem lesions become dark brown to black and result in girdling and plant death. Infected roots are dark brown and mushy. Leaf spots are small at first, irregular to round, and water-soaked. With age the spots enlarge, turn a light tan, and may crack. Infected areas may be bordered by white fungal-like growth during wet periods. Rapid blighting of new leaves and the entire emerging shoot may take place. Pepper fruits are infected through the stem. Fruit rot appears as dark green, water-soaked areas that become covered with white-gray, cottony, fungal-like growth. Infected fruit dries, becomes shrunken, wrinkled, and brown, and remains attached to the stem.

In eggplants, although the entire plant may be susceptible, fruit rot is the primary symptom caused by *P. capsici*. It begins as a round, dark brown area on any part of the fruit at any stage of maturity. The initial lesion is surrounded by a rapidly expanding light tan region. White to gray fungal-like growth may appear during wet, humid periods, starting on the oldest part of the fruit lesion. *Phytophthora* fruit rot in eggplant lacks the concentric patterns and dark fruiting structures present with *Phomopsis* rot, a fungus that also causes fruit rot on eggplant. Fruit rot in eggplant may also be caused by other *Phytophthora* spp. and *Phomopsis* spp.

In tomato, *Phytophthora capsici* can cause crown infections, leaf spot, and foliar blight. Diseased crowns are brown and soft and the plant may wilt and topple over. Another common symptom is fruit rot. Uninjured fruit of any age may be infected. Rot is most prevalent where fruit contacts the soil and begins as dark, water-soaked spots. The spot rapidly expands during warm weather and covers 50% or more of the fruit surface with a brown, water discoloration which may assume the appearance of concentric rings. At first, infected fruit remains smooth and firm even though the discoloration extends to its center. Over time and under humid conditions infected fruit may be covered with white fungal growth and rot entirely following invasion by secondary microorganisms. The symptoms of fruit rot in tomato caused by three other *Phytophthora* spp., *P. dreschlera* and *P. nicotianae*, and *P. parasitica* are essentially the same. Tomato fruit rot caused by *P. infestans* (late blight) is characterized by wrinkling and a definite, sunken margin.

Summer (yellow crookneck, zucchini) and winter (acorn, butternut) squash types are highly susceptible to *Phytophthora* foliar blight and fruit rot. Early foliar symptoms include rapidly expanding, irregular, water-soaked lesions in leaves. Dieback of shoot tips, wilting, shoot rot, and plant death quickly follow initial infection. Sunken, dark, water-soaked areas appear in infected fruit, and are rapidly covered by white fungal growth in yellow summer squash and zucchini.

Watermelon foliage is less susceptible to *P. capsici* than that of summer squash. Foliar symptoms of *Phytophthora* blight in watermelon are generally limited to water-soaked leaf blotches, which dry and turn brown, and dieback. However, all stages of watermelon fruit are highly susceptible. Early symptoms of fruit rot include rapidly expanding, irregular, brown lesions which become round to oval. Concentric rings may occur within a lesion. The centers of rotted areas are covered with grayish fungal-like growth, while the outer margins of lesions appear brown and water-soaked. The entire fruit eventually decays. Initial symptoms of bacterial fruit blotch of watermelon are similar to those caused by *P. capsici*. However, after lesions expand, the two diseases can be easily separated because of the presence of extensive rind cracking, absence of fungal-like growth, and other symptoms associated with bacterial fruit blotch. *Phytophthora* rot is characterized by abundant fungal-like growth accompanied by little or no cracking.

*Phytophthora capsici* may survive in and on seed and host plant debris in the soil by means of thick-walled spores (oospores). Certain weed species (Carolina geranium, American black nightshade, and common purslane) have also been found to serve as alternative hosts for *P. capsici* in Florida. Both mating types of the pathogen necessary for oospore production have been identified in Florida production fields, often from the same field. The pathogen produces spores of another type called zoospores that are contained within sac-like structures known as sporangia. Zoospores are motile and swim to reach and invade host tissue. Plentiful surface moisture is required for this activity. The sporangia are spread by wind-blown rain through the air and are carried with water movement in soil. The pathogen is also moved as mycelia (microscopic, fungal-like strands) in infected transplants and through contaminated soil and equipment. Since water is integral to the dispersal and infection of *P. capsici*, maximum disease occurs during wet weather and in low, water-logged parts of fields. Excessive rainfall, such as that which occurs during "El Niño" years, coupled with standing water creates ideal conditions for epidemics caused by *P. capsici*. Growth of this pathogen can occur between 46-99° F. (7-37° C.), but temperatures between 80-90° F. (27-32° C.) are optimal for producing zoospores and the infection process. Under ideal conditions, the disease can progress very rapidly and symptoms can occur 3-4 days after infection. Therefore, *P. capsici* can rapidly affect entire fields.

Traditional methods to control *P. capsici* are known. For example, management practices in transplant production areas include the use of pathogen-free and fungicide-treated seed, and sterile potting media. Flats, plug trays, benches, seeding equipment and plant house structures should be disinfested using a sodium hypochlorite solution or other disinfestant. Steam sterilization of flats and plug trays may be useful. Transplant trays with infected plants should not be transported to field production sites. Workers should disinfest their hands after contact with infected plants before resuming their duties. Planting sites should be well drained and free of low-lying areas. The drainage area of the field should be kept free of weeds and volunteer crop plants, particularly those in solanaceous and cucurbitaceous groups. A preplant, broad-spectrum fumigant should be used for planting sites in the field. However, unfumigated soil areas in and near the field can serve as sources of recontamination. Rotating to non-susceptible crops may limit the amount of disease inoculum residing in the soil, debris, and weeds. Equipment should be decontaminated before moving between infested and noninfested fields. Once a field is infested, it will remain infested for many years and should be avoided if possible. Infected fruit should be culled to prevent spread in the packing house and during shipment. Culled fruit should be destroyed so as not to become another source of contamination for the farm area. It is best to bury culls in an area that will not be used for agriculture. Effective, labelled fungicides should be used preventively according to label instructions. It is essential that fungicides with different modes of action be rotated to prevent the build-up of fungicide resistance in *P. capsici*. Rotating or tank-mixing a systemic with a contact fungicide is a good fungicide resistance management tool. Resistance to this disease has not been identified in cultivars currently grown in Florida. Foliar fungicides will minimize infection that occurs above the soil surface, but they will not be effective against infection sites in the soil.

Capsicum

The term pepper as used in agriculture may refer to quite different plant species. For example, some plants in the genera *Piper, Capsicum, Pimenta, Zanthoxylum, Schinus*, and several other species are called pepper. As used herein, the term pepper mainly refers to a plant species in the *Capsicum* genus, unless specified otherwise.

*Capsicum* is a genus of flowering plants in the Solanaceae family. Its species are native to the Americas, where they have been cultivated for thousands of years by the people of the tropical Americas, and are now cultivated worldwide. Some of the members of *Capsicum* are used as spices, vegetables, and medicines. The fruit of *Capsicum* plants have a variety of names depending on geographic location and fruit shape or type. They are commonly called chili pepper, red or green pepper, or sweet pepper in Britain, and typically called just *capsicum* in Australia, New Zealand, and Indian English. The large mild form is called bell pepper in the U.S. and Canada. They are called paprika in some other countries (although, somewhat confusingly, paprika can also refer to the powdered spice made from various *capsicum* fruit).

The fruit of most species of *Capsicum* contain capsaicin (methyl vanillyl nonenamide), a lipophilic chemical that can produce a strong burning sensation in the mouth of the unaccustomed eater. The secretion of capsaicin protects the fruit from consumption by mammals while the bright colors attract birds that will disperse the seeds.

Capsaicin is present in largest quantities in the placental tissue (which holds the seeds), the internal membranes and, to a lesser extent, the other fleshy parts of the fruits of plants in the genus *Capsicum*. The seeds themselves do not produce any capsaicin, although the highest concentration of capsaicin can be found in the white pith around the seeds.

The amount of capsaicin in *Capsicums* is highly variable and dependent on genetics, giving almost all types of *Capsicums* varied amounts of perceived heat. The only *Capsicum* without capsaicin is the bell pepper, a cultivar of *Capsicum annuum*, which has a zero rating on the Scoville scale. The lack of capsaicin in bell peppers is due to a recessive gene that eliminates capsaicin and, consequently, the "hot" taste usually associated with the rest of the *Capsicum* family.

Chili peppers are of great importance in Native American medicine, and capsaicin is used in modern medicine—mainly in topical medications—as a circulatory stimulant and analgesic. In more recent times, an aerosol extract of capsaicin, usually known as *capsicum* or pepper spray, has become widely used by police forces as a non-lethal means of incapacitating a person, and in a more widely dispersed form for riot control, or by individuals for personal defence. Although black pepper and Sichuan pepper cause similar burning sensations, they are caused by different substances—piperine and hydroxy-alpha sanshool, respectively.

Non-limiting exemplary *Capsicum* species include, *C. annuum, C. frutescens, C. chinense, C. pendulum, C. pubescens, C. minimum, C. baccatum, C. abbreviatum, C. anomalum, C. breviflorum, C. buforum, C. brasilianum, C. campylopodium, C. cardenasii, C. chacoense, C. ciliare, C. ciliatum, C. chlorocladium, C. coccineum, C. cordifbrme, C. cornutum, C. dimorphum, C. dusenii, C. exile, C. eximium, C. fasciculatum, C. fastigiatum, C. flexuosum, C. galapagoense, C. geminifolum, C. hookerianum, C. lanceolatum, C. leptopodum, C. luteum, C. microcarpum, C. minutiflorum, C. mirabile, C. parvifolium, C. praetermissum, C. schottianum, C. scolnikianum, C. stramonifolium, C. tetragonum, C. tovarii, C. villosum*, and *C. violaceum*. More *Capsicum* species are described in Heiser and Smith (The cultivated *Capsicum* peppers. Econ Bot 7:214-227), Pickersgill (1988, The genus *Capsicum*: a multidisciplinary approach to the taxonomy of cultivated and wild plants. Biologisches Zentralblatt 107: 381-389), De (*Capsicum*: the genus *Capsicum*, Volume 33 of Medicinal and aromatic plants, Publisher CRC Press, 2003, ISBN 0415299918, 9780415299916), Bosland and Votava (Peppers: vegetable and spice *capsicum*s, Issue 12 of Crop production science in horticulture, Publisher CABI, 2000, ISBN 0851993354, 9780851993355), and Andrews (Peppers: the domesticated *Capsicums*, Publisher University of Texas Press, 1995, ISBN 0292704674, 9780292704671).

*Capsicum* species have been characterized based on morphology, isozyme analysis, cytology, hybridization, restriction fragment length polymorphism (RFLP), amplified fragment length polymorphism (AFLP), random amplified polymorphic DNA (RAPD), sequence specific amplification polymorphism (S-SAP), simple sequence repeat length polymorphism (SSRLP), inter-simple sequence repeats (ISSR), cleaved amplified polymorphic sequence (CAPS), and direct or directed amplification of minisatellite region DNA amplified using the polymerase chain reaction (DAMD-PCR), for the identification of genotypes or accessions at the taxonomic level, assessment of the relative diversity or similarity within and between species, and selection of diverse accessions with desirable traits for breeding purposes (Eshbaugh 1993; Prince et al. 1992; Rodriguez et al. 1999; Lefebvre et al. 2001; Adetula 2006; Guzman et al. 2005; Ince et al. 2009).

Most *Capsicum* species are diploid (2n=2x=24), but there are a few species for which the genome is 2n=2x=32. *Capsicum* has a large genome, with the DNA content ranging from 7.65 pg/nucleus in *C. annuum* to 9.72 pg/nucleus in *C. pubescens*, and with a general mean of 8.42 pg/nucleus. *Capsicum* genes have been studied for almost a century since 1912, and a list of genes and related traits are described by Wang (2006, The Genes of *Capsicum*, HortScience 41(5) 1169-1187), which is incorporated by reference in its entirety. These gene include, but are not limited to, genes determining morphological traits (such as plant height, flaccid phenotypes, branching habits, fasciculation, leaf shape, color of plant parts, variegated seedlings, flowers, fruit shapes, immature fruit colors, mature fruit colors, transition of fruit colors), genes determining physiological traits (such as pungency, beta-carotene contents, soft flesh and deciduous fruits), genes determining sterility traits (such as genic male sterility, cytoplasmic male sterility, functional male sterility, female sterility), and genes determining resistance to diseases, nematodes, and herbicides (such as resistance to tobacco mosaic virus, resistance to cucumber mosaic virus, resistance to potyvirus, resistance to tomato spotted wilt tospovirus, resistance to bacterial leaf spot, resistance to phytophthora, resistance to anthracnose, resistance to *Ralstonia solanacearum*, resistance to powdery mildew, resistance to root knot nematodes, and bentazon herbicide tolerance).

Six genes have been identified to affect the characteristics of fruit shapes. Deshpande (1933, Studies in Indian chilies. 3. The inheritance of some characters in *Capsicum annuum* L. Indian Jour. Agr. Sci. 3:219-300) described the dominant gene P for pointed fruit apex, the recessive gene fb for fruit base nonbulging, and the gene ce for calyx enclosed around fruit base (Daskalov and Poulos, 1994, Updated *Capsicum* gene list, *Capsicum* Eggplant Nswl. 13:16-26). The round fruit shape is controlled by the major dominant gene 0 and other modifiers (Peterson, 1959, Linkage of fruit shape and color genes in *Capsicum*, Genetics, 44:407-419), and recent molecular mapping studies confirm the existence of the major genes that control this trait (Ben Chaim et al., 2001, QTL mapping of fruit-related traits in pepper (*Capsicum annuum*). Theor. Appl. Genet. 102:1016-1028; Ben Chaim et al., 2003, Linkage of the A locus for the presence of anthocyanin and fs10.1, a major fruit-shape QTL in pepper. Theor. Appl. Genet., 106:889-894; and Rao and Paran, 2003, Polygalacturonase: A candidate gene for the soft flesh and deciduous fruit mutation in *Capsicum*, Plant Mol. Biol. 51:135-141). Upright fruit orientation is controlled by two recessive genes (up-1 and up-2) that show specific dominant and recessive epistasis respectively (Gopalakrishnan et al., 1990, Inheritance of clusterness and fruit orientation in chili (*Capsicum annuum* L.) Indian J. Genetics 49:219-222; Lippert et al., 1965, Gene list for the pepper. J. Hered. 56:30-34). Csillery (1983, New *Capsicum* mutants found on seedling, growth type, leaf, flower and fruit. Proc. 5$^{th}$ Eucarpia Meeting of *Capsicum* and Eggplant Working Group, 4-7 Jul. 1983, Plovdiv. 127-130) identified the recessive gene cy, responsible for the exocarp covered with transversally oriented, small suberized cracks at full fruit maturity. Ishikawa and coworkers (1998, Inheritance of the fruit shape at the apex and the peduncle attachment of pepper, *Capsicum* Eggplant Nswl. 17:30-33) reported the dominant Ap and Ped genes to condition the pointed shape of the fruit apex, and the acute shape of the fruit pedicle attachment respectively. The allelism between Ap and P is unknown. Each of the publications mentioned above is incorporated by reference in its entirety.

Figure 2:
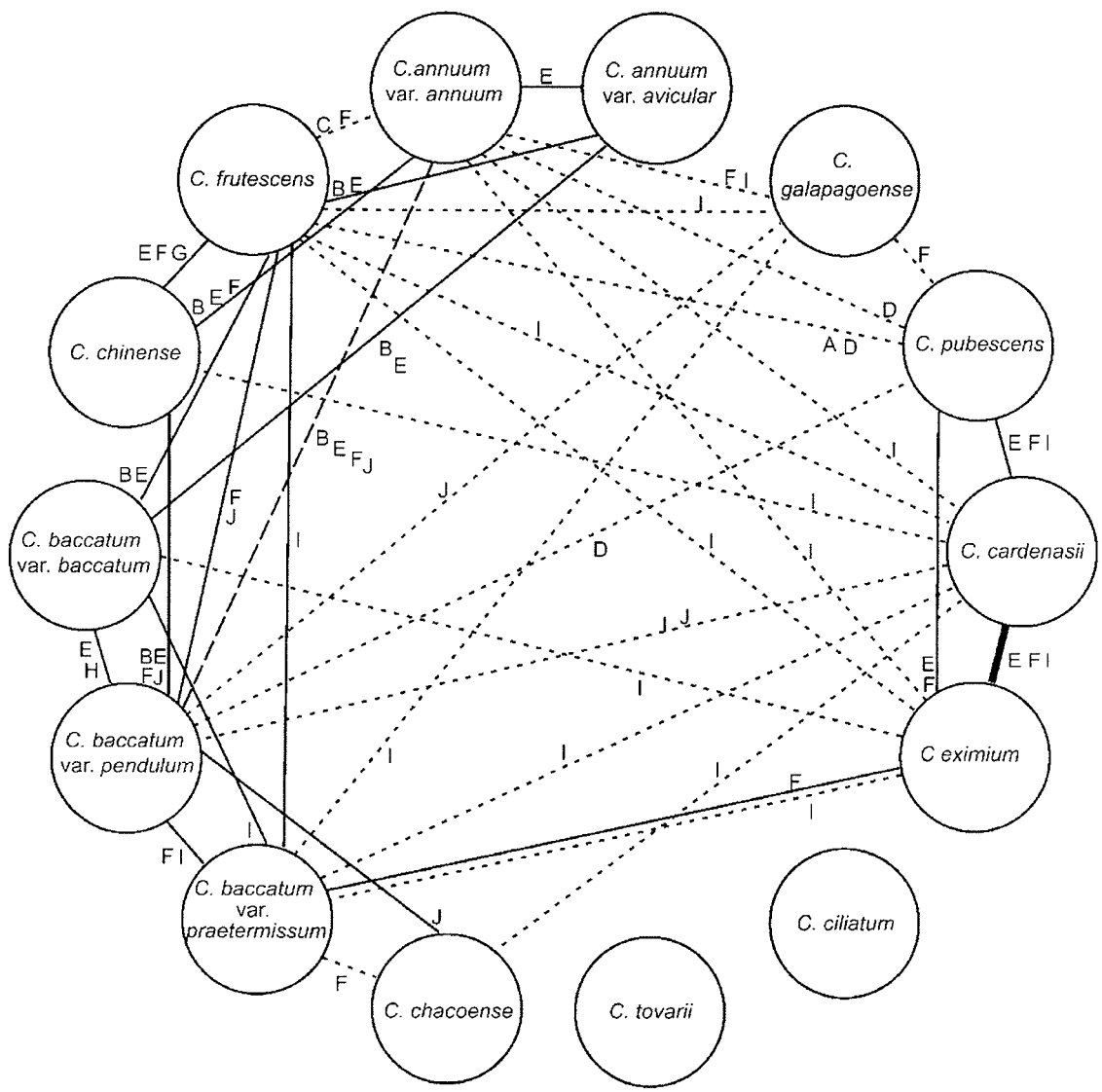

Enzymatic studies of *Capsicum* (Jensen et al., 1979; McLeod et al, 1979a, 1979b, 1982, 1983) have demonstrated that *Capsicum* species can be grouped into three taxonomic categories (*Capsicum annuum* complex, *Capsicum baccatum* complex, and *Capsicum eximium* complex) that somewhat agreed with groupings based on flower color (FIG. 1). Hybrid analyses have been used extensively to resolve species relationships in *Capsicum* (Heiser and Smith 1948, 1953, 1958; Smith and Heiser 1951, 1957; Emboden 1961; Lippert et al. 1966; Eshbaugh 1970, 1976; Peckersgill 1971; Eshbaugh et al. 1983, each of which is incorporated by reference in its entirety). To determine the viability of hybrids between various species of *Capsicum*, pollen staining and F1 seed germination studies were used. The results of these hybrid analyses are shown in FIG. 2. Interspecific hybridization among *Capsicum* species are also discussed by Bosland and Votava (Peppers: vegetable and spice capsicums, Issue 12 of Crop production science in horticulture, Publisher: CABI, 2000, ISBN 0851993354, 9780851993355), which is incorporated by reference in its entirety.

*Capsicum annuum*

*Capsicum annum* is a domesticated species of the plant genus *Capsicum* native to South America and it is now cultivated worldwide. Despite being a single species, the *Capsicum annuum* has many forms, with a variety of names, even in the same language. In American English it is commonly known as the chili pepper, although not all varieties would be recognized by most speakers under this name. In British English, the sweet varieties are called peppers and the hot varieties are called chilies, whereas in Australian English the name *capsicum* is commonly used for bell peppers exclusively and chili is often used to encompass the hotter varieties. Its forms are varied, from large to small, sweet to sour, very hot to bland.

The plant is a herbaceous annual, with a densely branched stem. The plant reaches 0.5-1.5 m (20-60 in). Single white flowers bear the fruit which is green when unripe, changing principally to red, although some varieties may ripen to brown or purple. While the species can tolerate most climates, they are especially productive in warm and dry climates.

Non-limiting exemplary *Capsicum annuum* varieties include, Aleppo, Anaheim, Bell, Cascabel, Cayenne, Cherry, Chilaca, Chiltepin, Cubanelle, De árbol, Fresno, Guajillo, Guntur, Sannam, Hungarian wax, Italian sweet pepper, Jalapeño, Japanese, Mirasol, Macho, New Mexico, Pepperoncini, Pequin pepper, Poblano, Puya, Serrano, Super Chili, and Tien Tsin.

Bell Pepper

Bell pepper or sweet pepper or sweet bell pepper is a cultivar group of the species *Capsicum annuum*. Cultivars of the plant produce fruits in different colors, for example, green, red, yellow, orange, white, purple, and rainbow, depending on when they are harvested and the specific cultivar. The term "bell pepper" is often used for any of the large bell shaped *capsicum* fruits, regardless of their color. As used herein, the phrase "bell pepper" is equivalent to "blocky type pepper" or "blocky shape pepper", as this term is understood by those skilled in the art of pepper breeding and pepper production. The fruit is also frequently consumed in its unripe form, when the fruit is still green.

In the United States and Canada, in addition to the terms "bell pepper" and "sweet pepper," the fruit is often referred to simply as a "pepper" or referred to by color (e.g. "red pepper", "green pepper", "yellow pepper"), although the more specific term "bell pepper" is understood in most regions. In parts of Indiana, Ohio, and Pennsylvania, the fruit is called a "mango". The origin of this use is in the use of the term "mango" or "mangoed" to refer to pickled fruits. At a certain time, mangoes were available in the United States only in pickled form. Later, it became common in these regions to use bell peppers in pickled form, thus the term "mangoed peppers" or "mango peppers" later shortened to "mangoes."

Green peppers are less sweet and slightly bitter than red, yellow or orange peppers. The taste of ripe peppers can also vary with growing conditions and post-harvest storage treatment; the sweetest are fruit allowed to ripen fully on the plant in full sunshine, while fruit harvested green and after-ripened in storage are less sweet. Compared to green peppers, red peppers have more vitamins and nutrients and contain the antioxidant lycopene. The level of carotene, another antioxidant, is nine times higher in red peppers. Red peppers also have twice the vitamin C content of green peppers. Orange bell peppers (or paprikas) contain even more vitamin C and significantly more vitamin A. Orange bell peppers are both juicy and sweet, and because they contain less than half the calories of an orange, orange bell peppers are pre-eminently appropriate as a refreshing, low-calorie food, both raw and prepared in any dish. They can be eaten raw without having indigestion later.

QTLs Contributing to Resistance to *Phytophthora capsici* and Agronomic Traits in *Capsicum annuum*, and Molecular Markers Detecting the QTLs It has been reported that some accessions of pepper have resistance to *Phytophthora capsici* (Barksdale et al., 1984, Reifschneider et al. 1992, and Ortega et al., 1992). The pepper land race 'Criollo de Morelos 334' ('CM334'), from the Mexican state of Morelos, and USDA 'PI201234', an accession from Central America, are highly resistant to *Phytophthora capsici* (Ortega et al., 1991, Walker and Bosland 1999, and Oelke et al. 2003). Several classic studies on the inheritance of *P. capsici* resistance in pepper have been conducted (Smith et al. 1967; Bartual et al. 1991, 1994; Ortega et al. 1991, 1992; Kim et al. 1989; Palloix et al. 1988, 1990; Walker and Bosland 1999). These studies do not agree on the number of genes conditioning resistance; the number of resistance genes being reported varied from 1 to many, and the possibility of epistatic effects was raised. There is a strong indication, however, that resistance to *P. capsici* is polygenic (Lefebvre and Palloix 1996; Thabuis et al. 2003).

Non-limiting exemplary quantitative trait loci (QTLs) contributing to *Phytophthora* resistances in pepper have been described. Several linkage maps of pepper have been reported (Prince et al. 1993; Livingstone et al. 1999; Kim et al. 1998; Lefebvre et al. 1995, 2002; Lee et al. 2004; Paran et al. 2004, Ogundiwin et al. 2005; Lefebvre and Palloix 1996; Thabuis et al., 2003, 2004a, and 2004b, Sy et al., 2005). Resistance to *Phytophthora* is also discussed in Sugita et al., 2006, Bonnet et al., 2007, Minamiyama et al., 2007, Oelke and Bosland, 2003, and Glosier et al., 2007. Each of references mentioned above is herein incorporated by reference in its entirety.

Lefebvre and Palloix (1996) used the linkage map of Lefebvre et al. (1995) to detect, with a single isolate, up to 13 quantitative trait loci (QTLs) that control inheritance of *P. capsici* resistance. Thabuis et al. (2003), using the improved map of Lefebvre et al. (2002) and 2 strains of the pathogen, studied the genetics of *P. capsici* resistance in 3 different intraspecific populations of pepper; they detected several QTLs, some common to all, and some specific to each population. Ogundiwin et al. (2005) reported resistance QTLs detected from two linkage maps that affect resistance to foliar blight and root rot, involving 7 different *P. capsici* isolates, based on 2 linkage intraspecific mapping populations generated from the hybridization of 'CM334' and 'PI201234' with two *P. capsici*-susceptible pepper lines.

Thabuis et al. (2003) described chromosomal regions that are involved resistance to *P. capsici*. based on analysis of three intraspecific populations of pepper. Six resistance regions from 'CM334' located on Chromosome 5 (2 regions), Chromosome 6 (2 regions), Chromosome 11, and Chromosome 12 are also found in other two intraspecific populations (Thabuis et al., 2003, the entire article is hereby specifically incorporated by reference in its entirety). As used herein, the term "chromosome" is interchangeably with the phrase "linkage group".

Non-limiting exemplary QTLs in pepper contributing to agronomic traits are described in Ben Chaim 2001, Ben Chaim et al., 2003a, 2003b, Bachi et al. 2009, Rao et al., 2003, and Zygier et al., 2005, each of which is herein incorporated by reference in its entirety.

For the first time in the art, the present invention successfully integrated at least four QTLs, at least five QTLs, and at least six QTLs which can be found in 'CM334' into a pepper plant with blocky type fruits or rectangular ¾ long type fruits or half long type fruits. Half long type fruits are in-between the ¾ long and the blocky pepper (see FIG. 6).

The QTLs related to *Phytophthora* resistance or agronomic values may be discovered through QTL mapping. QTL mapping can be applied to determine the parts of the donor plant's genome conferring the *Phytophthora* resistance, and facilitate the breeding methods. Inheritance of quantitative traits or polygenic inheritance refers to the inheritance of a phenotypic characteristic that varies in degree and can be attributed to the interactions between two or more genes and their environment. Though not necessarily genes themselves, quantitative trait loci (QTLs) are stretches of DNA that are closely linked to the genes that underlie the trait in question. QTLs can be molecularly identified to help map regions of the genome that contain genes involved in specifying a quantitative trait. This can be an early step in identifying and sequencing these genes.

Typically, QTLs underlie continuous traits (those traits that vary continuously, e.g. level of resistance to pathogen) as opposed to discrete traits (traits that have two or several character values, e.g. smooth vs. wrinkled peas used by Mendel in his experiments). Moreover, a single phenotypic trait is usually determined by many genes. Consequently, many QTLs are associated with a single trait.

A QTL is a region of DNA that is associated with a particular phenotypic trait—these QTLs are often found on different chromosomes. Knowing the number of QTLs that explains variation in a particular phenotypic trait informs about the genetic architecture of the trait. It may tell that plant resistance to a specific pathogen is controlled by many genes of small effect, or by a few genes of large effect.

Another use of QTLs is to identify candidate genes underlying a trait. Once a region of DNA is identified as contributing to a phenotype, it can be sequenced. The DNA sequence of any genes in this region can then be compared to a database of DNA for genes whose function is already known.

In a recent development, classical QTL analyses are combined with gene expression profiling i.e. by DNA microarrays. Such expression QTLs (e-QTLs) describes cis- and trans-controlling elements for the expression of often disease-associated genes. Observed epistatic effects have been found beneficial to identify the gene responsible by a cross-validation of genes within the interacting loci with metabolic pathway- and scientific literature databases.

QTL mapping is the statistical study of the alleles that occur in a locus and the phenotypes (physical forms or traits) that they produce (see, Meksem and Kahl, *The handbook of plant genome mapping: genetic and physical mapping*, 2005, Wiley-VCH, ISBN 3527311165, 9783527311163). Because most traits of interest are governed by more than one gene, defining and studying the entire locus of genes related to a trait gives hope of understanding what effect the genotype of an individual might have in the real world.

Statistical analysis is required to demonstrate that different genes interact with one another and to determine whether they produce a significant effect on the phenotype. QTLs identify a particular region of the genome as containing a gene that is associated with the trait being assayed or measured. They are shown as intervals across a chromosome, where the probability of association is plotted for each marker used in the mapping experiment.

To begin, a set of genetic markers must be developed for the species in question. A marker is an identifiable region of variable DNA. Biologists are interested in understanding the genetic basis of phenotypes (physical traits). The aim is to find a marker that is significantly more likely to co-occur with the trait than expected by chance, that is, a marker that has a statistical association with the trait. Ideally, they would be able to find the specific gene or genes in question, but this is a long and difficult undertaking. Instead, they can more readily find regions of DNA that are very close to the genes in question. When a QTL is found, it is often not the actual gene underlying the phenotypic trait, but rather a region of DNA that is closely linked with the gene.

For organisms whose genomes are known, one might now try to exclude genes in the identified region whose function is known with some certainty not to be connected with the trait in question. If the genome is not available, it may be an option to sequence the identified region and determine the putative functions of genes by their similarity to genes with known function, usually in other genomes. This can be done using BLAST, an online tool that allows users to enter a primary sequence and search for similar sequences within the BLAST database of genes from various organisms.

Another interest of statistical geneticists using QTL mapping is to determine the complexity of the genetic architecture underlying a phenotypic trait. For example, they may be interested in knowing whether a phenotype is shaped by many independent loci, or by a few loci, and do those loci interact. This can provide information on how the phenotype may be evolving.

Molecular markers are used for the visualization of differences in nucleic acid sequences. This visualization is possible due to DNA-DNA hybridization techniques (RFLP) and/or due to techniques using the polymerase chain reaction (e.g. STS, microsatellites, AFLP). All differences between two parental genotypes will segregate in a mapping population based on the cross of these parental genotypes. The segregation of the different markers may be compared and recombination frequencies can be calculated. The recombination frequencies of molecular markers on different chromosomes are generally 50%. Between molecular markers located on the same chromosome the recombination frequency depends on the distance between the markers. A low recombination frequency corresponds to a low distance between markers on a chromosome. Comparing all recombination frequencies will result in the most logical order of the molecular markers on the chromosomes. This most logical order can be depicted in a linkage map (Paterson, 1996). A group of adjacent or contiguous markers on the linkage map that is associated to a reduced disease incidence and/or a reduced lesion growth rate pinpoints the position of a QTL.

The nucleic acid sequence of a QTL may be determined by methods known to the skilled person. For instance, a nucleic acid sequence comprising said QTL or a resistance-conferring part thereof may be isolated from a *Phytophthora*-resistant donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

One or more such QTLs associated with the resistance to *Phytophthora* in a donor plant can be transferred to a recipient plant that is susceptible to *Phytophthora* to make it become resistant through any transferring and/or breeding methods.

In one embodiment, an advanced backcross QTL analysis (AB-QTL) is used to discover the nucleotide sequence or the QTLs responsible for the resistance of a plant. Such method was proposed by Tanksley and Nelson in 1996 (Tanksley and Nelson, 1996, Advanced backcross QTL analysis: a method for simultaneous discovery and transfer of valuable QTL from un-adapted germplasm into elite breeding lines. *Theor Appl Genet* 92:191-203) as a new breeding method that integrates the process of QTL discovery with variety development, by simultaneously identifying and transferring useful QTL alleles from un-adapted (e.g., land races, wild species) to elite germplasm, thus broadening the genetic diversity available for breeding. AB-QTL strategy was initially developed and tested in tomato, and has been adapted for use in other crops including rice, maize, wheat, pepper, barley, and bean. Once favorable QTL alleles are detected, only a few additional marker-assisted generations are required to generate near isogenic lines (NILs) or introgression lines (ILs) that can be field tested in order to confirm the QTL effect and subsequently used for variety development.

Isogenic lines in which favorable QTL alleles have been fixed can be generated by systematic backcrossing and introgressing of marker-defined donor segments in the recurrent parent background. These isogenic lines are referred as near isogenic lines (NILs), introgression lines (ILs), backcross inbred lines (BILs), backcross recombinant inbred lines (BCRIL), recombinant chromosome substitution lines (RCSLs), chromosome segment substitution lines (CSSLs), and stepped aligned inbred recombinant strains (STAIRSs). An introgression line in plant molecular biology is a line of a crop species that contains genetic material derived from a similar species. ILs represent NILs with relatively large average introgression length, while BILs and BCRILs are backcross populations generally containing multiple donor introgressions per line. As used herein, the term "introgression lines or ILs" refers to plant lines containing a single marker defined homozygous donor segment, and the term "pre-ILs" refers to lines which still contain multiple homozygous and/or heterozygous donor segments.

To enhance the rate of progress of introgression breeding, a genetic infrastructure of exotic libraries can be developed. Such an exotic library comprises of a set of introgression lines, each of which has a single, possibly homozygous, marker-defined chromosomal segment that originates from a donor exotic parent, in an otherwise homogenous elite genetic background, so that the entire donor genome would be represented in a set of introgression lines. A collection of such introgression lines is referred as libraries of introgression lines or IL libraries (ILLs). The lines of an ILL cover usually the complete genome of the donor, or the part of interest. Introgression lines allow the study of quantitative trait loci, but also the creation of new varieties by introducing exotic traits. High resolution mapping of QTL using ILLs enable breeders to assess whether the effect on the phenotype is due to a single QTL or to several tightly linked QTL affecting the same trait. In addition, sub-ILs can be developed to discover molecular markers which are more tightly linked to the QTL of interest, which can be used for marker-assisted breeding (MAB). Multiple introgression lines can be developed when the introgression of a single QTL is not sufficient to result in a substantial improvement in agriculturally important traits (Gur and Zamir, Unused natural variation can lift yield barriers in plant breeding, 2004, *PLoS Biol.;* 2(10): e245).

The inventors of the present invention also provide molecular markers that are linked to the *Phytophthora* resistance gens/QTLs and/or agronomic genes/QTLs of the present invention. These molecular markers and their defining primers are described in Table 1. As used herein, the term "linked" refers to the situation wherein the molecular marker and at least one of the *Phytophthora* resistant QTLs and/or agronomic QTLs of the present invention are segregating together over one or more generations. In one embodiment, the molecular markers of the present invention are linked to at least one of the *Phytophthora* resistant loci and/or agronomic trait loci of the present invention. In some embodiments, the molecular marker and the *Phytophthora* resistant locus and/or agronomic trait locus are segregating together in at least about 25% of a particular population in a particular generation. In one embodiment, the molecular marker can be any kind of marker described herein. For example, the molecular marker can be any SSR markers, such as the SSR markers which defining primers are listed in Table 1. The nucleotide sequences defining primers of the SSR markers are shown in Table 1, or a complementary strand thereof can be used. In some embodiments, the genetic distance between the molecular marker and at least one of the *Phytophthora* resistant QTLs and/or agronomic QTLs is less than 20 centimorgan (cM), less than 15 cM, less than 10 cM, less that 9 cM, less than 8 cM, 7 cM, 6 cM, 5 cM, 4 cM, 3 cM, less than 2 cM, less than 1 cM, or even less.

In one embodiment, the molecular markers of the present invention are closely linked to at least one of the *Phytophthora* resistant loci and/or agronomic trait loci of the present invention. As used herein, the phrase "closely linked" or "tightly linked" refers to the situation wherein the genetic distance between the molecular marker and at least one of the *Phytophthora* resistant QTLs and/or agronomic QTLs is less than 2 centimorgan (cM). For example, the genetic distance between the marker and the QTL is about 2.0 cM, about 1.9 cM, about 1.8 cM, about 1.7 cM, about 1.6 cM, about 1.5 cM, about 1.4 cM, about 1.3 cM, about 1.2 cM, about 1.1 cM, about 1.0 cM, about 0.9 cM, about 0.8 cM, about 0.7 cM, about 0.6 cM, about 0.5 cM, about 0.4 cM, about 0.3 cM, about 0.2 cM, about 0.1 cM, or less than 0.1 cM Molecular markers have proven to be of great value for increasing the speed and efficiency of plant breeding. Most traits of agronomic value, e.g. pest resistance, yield and the like, are difficult to measure, often requiring a full growth season and statistical analysis of field trial results. Interpretation of the data can be obscured or confused by environmental variables. Occasionally it has been possible for breeders to make use of conventional markers such as flower color which could be readily followed through the breeding process. If the desired gene or QTL is linked closely enough to a conventional marker, the likelihood of recombination occurring between them is sufficiently low that the gene or the QTL and the marker co-segregate throughout a series of crosses. The marker becomes, in effect, a surrogate for the gene or the QTL itself. Prior to the advent of molecular markers, the opportunities for carrying out marker-linked breeding were severely limited by the lack of suitable markers mapping sufficiently close to the desired trait. Map distance is simply a function of recombination frequency between two markers, genes, QTLs, genes and QTLS, or markers and genes or QTLs. Consequently, if a marker and a gene or a QTL map too far apart, too much recombination will occur during a series of crosses or self-pollinations such that the marker becomes no longer associated with the gene or the QTL. Having a wide selection of molecular markers available throughout the genetic map provides breeders the means to follow almost any desired trait through a series of crosses, by measuring the presence or absence of a marker linked to the gene or the QTL which affects that trait. The primary obstacle is the initial step of identifying a linkage between a marker and a gene or a QTL affecting the desired trait.

More molecular markers can be developed by using the *Phytophthora* resistance plants with agronomic traits of the present invention. In general, as the map distance (expressed by the unit cM) between a molecular marker and a gene of interest becomes shorter, the marker and the gene are more closely localized to each other, and more likely to be inherited simultaneously; thus such markers are more useful. Methods of developing molecular markers are well known to one of ordinary skill in the art. The marks can be bi-allelic dominant, bi-allelic co-dominant, and/or multi-allelic co-dominant. The types of molecular markers that can be developed include, but are not limited to, restriction fragment length polymorphisms (RFLPs), isozyme markers, allele specific hybridization (ASH), amplified variable sequences of plant genome, self-sustained sequence replication, simple sequence repeat (SSR), single base-pair change (single nucleotide polymorphism, SNP), random amplification of polymorphic DNA (RAPDs), SSCPs (single stranded conformation polymorphisms); amplified fragment length polymorphisms (AFLPs) and microsatellites DNA. RAPD methods generally refer to methods of detecting DNA polymorphisms using differences in the length of DNAs amplified using appropriate primers. AFLP methods are essentially a combination of the above RFLP and RAPD methods, and refer to methods of selectively amplifying DNA restriction fragments using PCR to detect differences in their length, or their presence or absence.

Methods of developing molecular markers and their applications are described by Avise (Molecular markers, natural history, and evolution, Publisher: Sinauer Associates, 2004, ISBN 0878930418, 9780878930418), Srivastava et al. (Plant biotechnology and molecular markers, Publisher: Springer, 2004, ISBN 1402019114, 9781402019111), and Vienne (Molecular markers in plant genetics and biotechnology, Publisher: Science Publishers, 2003), each of which is incorporated by reference in its entirety.

The AFLP technology (Zabeau & Vos, 1993; Vos et al., 1995) has found widespread use in plant breeding and other field since its invention in the early nineties. This is due to several characteristics of AFLP, of which the most important is that no prior sequence information is needed to generate large numbers of genetic markers in a reproducible fashion, in addition, the principle of selective amplification, a cornerstone of AFLP, ensures that the number of amplified fragments can be brought in line with the resolution of the detection system, irrespective of genome size or origin.

Detection of AFLP fragments is commonly carried out by electrophoresis on slab-gels (Vos et al., AFLP: a new technique for DNA fingerprinting, Nucleic Acids Res. 1995 Nov. 11; 23(21): 4407-4414, 1995) or capillary electrophoresis (van der Meulen et al., 2002). The majority of AFLP markers scored in this way represent polymorphisms occurring either in the restriction enzyme recognition sites used for AFLP template preparation or their flanking nucleotides covered by selective AFLP primers. The remainder of the AFLP markers are insertion/deletion polymorphisms occurring in the internal sequences of the restriction fragments and a very small fraction on single nucleotide substitutions occurring in small restriction fragments (<approximately 100 bp), which for these fragments cause reproducible mobility variations between both alleles which can be observed upon electrophoresis; these AFLP markers can be scored co-dominantly without having to rely on band intensities. Methods of developing AFLP markers are described in EP 534858, U.S. Pat.

No. 6,045,994, WO2007114693 and Vos et al., each of which is hereby incorporated by reference in its entirety.

The molecular markers of the present invention are genetically linked to the QTLs associated with *Phytophthora* resistance or QTLs associated with fruit shape and/or fruit weight. It should be understood that these molecular markers merely indicate nucleic acid sequence polymorphisms between the genome of a *Capsicum annuum* plant having said QTLs and the genome of a *Capsicum annuum* plant not having said QTLs. The polymorphisms can be detected by PCR amplification, or any other suitable methods well known to one skilled in the art. The exact size of an amplification product using the primer pairs provided herein may vary between two plants, for example, due to natural variation, even when said two plants have essentially the same QTL that is associated with *Phytophthora* resistance or fruit shape and/or fruit weight. For example, the essentially same QTL in LG2 (Chromosome 2) contributing to *Phytophthora* resistance are present in both 'CM334' plant and '07SRTC1802' plant. In both plant backgrounds, the QTL is linked to marker EPMS709, and the amplification product using EPMS709-F/R primers from 'CM334' is about 283 bp, while the amplification product using the same primer pair from '07SRTC1802' is about 297 bp. Therefore, the molecular markers merely reflect existence of a polymorphic region that can be used as an indicator of presence of certain QTLs genetically linked to that region. For example, a *Capsicum annuum* plant X other than 'CM334' may contain one or more essentially the same QTLs contributing to *Phytophthora* resistance (i.e., QTLs essentially the same as those in LG1/8, LG2, LG3, LG5, LG6, and/or LG10 of 'CM334' plant), so such plant can be used as a source ("donor plant") to produce the *Capsicum annuum* plants of the present invention, even though the amplification product from plant X using the same marker primer pair is different from that of 'CM334' plant. Nevertheless, the amplification product from the plant X using a primer pair of the present invention should be distinctive from the amplification product from a check *Capsicum annuum* plant, wherein the check plant is susceptible to *Phytophthora*, for example, the check plant has a *Phytophthora* resistance score of 3 to 5 based on a stem decapitation test using a virulent *Phytophthora* isolate, such as '1Z2', 'N101', 'Italie 07', 'Californie 1-07', 'New Jersey', 'Californie 2-07', 'Floride 07', 'France 07', 'Mexique '07', 'S197', 'Mexique 2-07', 'France 2-09', or 'Shandong 09'. In some embodiments, the difference in size of amplification products from a donor plant and a check plant is about 1 bp, 2 bp, 3 bp, 4 bp, 5 bp, 6 bp, 7 bp, 8 bp, 9 bp, 10 bp, 11 bp, 12 bp, 13 bp, 14 bp, 15 bp, 16 bp, 17 bp, 18 bp, 19 bp, 20 bp, 25 bp, 30 bp, 35 bp, 40 bp, 45 bp, 50 bp, 55 bp, 60 bp, 65 bp, 70 bp, 75 bp, 80 bp, 85 bp, 90 bp, 95 bp, 100 bp or more.

*Capsicum* Plants Resistant to *Phytophthora capsici* with Agronomic Traits

The present invention provides *Capsicum* plants with resistant to at least one *Phytophthora* species. In one embodiment, said *Capsicum* plants comprise one or more agronomic traits related to fruit.

In one embodiment, said *Capsicum* plants are *Capsicum annuum* plants. In some other embodiments, said *Capsicum* plant is derived a progeny produced by a cross between a first *Capsicum* parent and a second *Capsicum* parent, wherein at least one of the parent is a *Capsicum annuum* plant. In some embodiments, the other *Capsicum* parent is a *Capsicum* plant selected from the group consisting of *C. frutescens, C. chinense, C. pendulum, C. pubescens, C. minimum, C. baccatum, C. abbreviatum, C. anomalum, C. breviflorum, C. buforum, C. brasilianum, C. campylopodium, C. cardenasii, C. chacoense, C. ciliare, C. ciliatum, C. chlorocladium, C. coccineum, C. cordiforme, C. cornutum, C. dimorphum, C. dusenii, C. exile, C. eximium, C. fasciculatum, C. fastigiatum, C. flexuosum, C. galapagoense, C. geminifolum, C. hookerianum, C. lanceolatum, C. leptopodum, C. luteum, C. microcarpum, C. minutiflorum, C. mirabile, C. parvifolium, C. praetermissum, C. schottianum, C. scolnikianum, C. stramonifolium, C. tetragonum, C. tovarii, C. villosum, C. violaceum,* and *Capsicum* species derived from thereof. Cross compatibility between *Capsicum* species are described herein in the specification.

In one embodiment, the *Phytophthora* species is *Phytophthora capsici*. In further embodiments, said *Phytophthora* is a *Phytophthora capsici* isolate selected from the group consisting of 1Z2, N 101, Italie 07, Californie 1-07, New Jersey, S197, Californie 2-07, Floride 07, France 07, Mexique 07, and progenies equivalent to, or derived from thereof. In other embodiments, said *Phytophthora* species is one of the *Phytophthora* species described elsewhere herein.

In one embodiment, said *Phytophthora* resistant *Capsicum* plants comprise one or more *Phytophthora* resistance genes and/or QTLs described herein, e.g., those described by Prince et al. 1993; Livingstone et al. 1999; Kim et al. 1998; Lefebvre et al. 1995, 2002; Lee et al. 2004; Paran et al. 2004, Ogundiwin et al. 2005; Lefebvre and Palloix 1996; Thabuis et al., 2003, 2004a, and 2004b, Sy et al., 2005, Sugita et al., 2006, Bonnet et al., 2007, Minamiyama et al., 2007, Oelke and Bosland, 2003, and Glosier et al., 2007. In some embodiments, said *Phytophthora* resistance genes and/or QTLs can be found in pepper lines 'CM334', Perennial, 'PI201234', and/or progenies derived from thereof. In some embodiments, said *Phytophthora* resistant *Capsicum* plants comprise the six *Phytophthora* resistance QTLs that can be found in 'CM334' and/or some other *Capsicum* plants, which are designated as P1/8, P2, P3, P5, P6, and P10. In one embodiment, at least four, at least five, or all of said six *Phytophthora* resistance QTLs are all derived from 'CM334'. In some embodiments, said *Phytophthora* resistant *Capsicum* plants comprise at least four, at least five, or all of six *Phytophthora* resistance QTLs derived from one or more *Capsicum* plants, wherein the six *Phytophthora* resistance QTLs are the same or equivalent to the six *Phytophthora* resistance QTLs derived from 'CM334'. For example, in some embodiments, the P1/8, P2, P5, and P10 QTLs are derived from 'CM334', and the P3 and/or P6 QTLs are from other *Capsicum* plants. In some embodiments, the P3 and/or P6 QTLs are from a *Capsicum annum* plant with blocky type fruit. The defining primers of each of the six QTLs are shown in Table 1 and FIG. 4.

Figure 6:
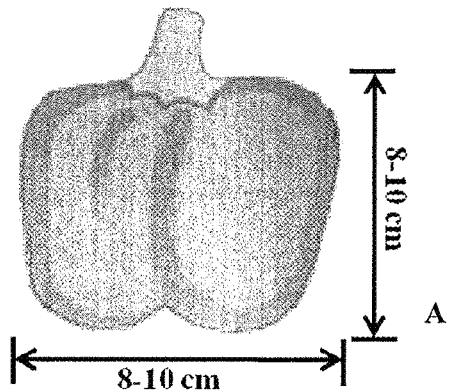
Figure 6:
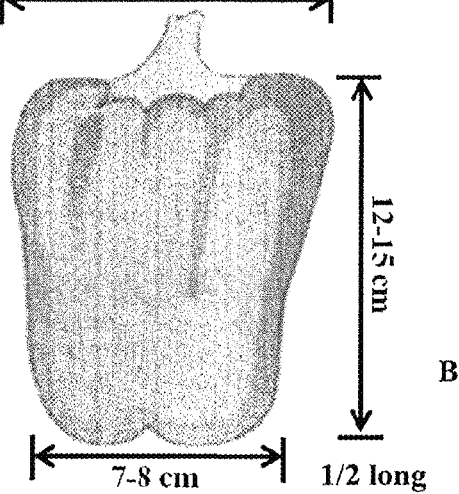
Figure 6:
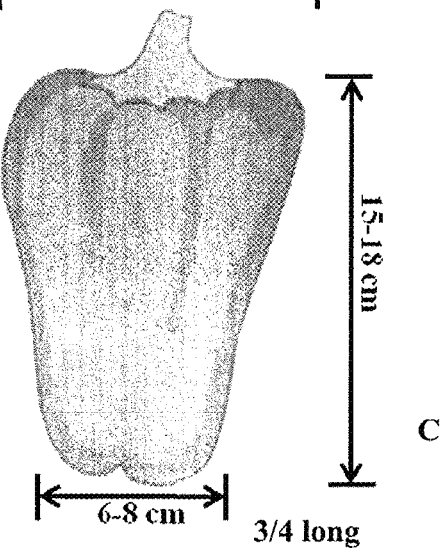

In one embodiment, the agronomic traits related to fruit are selected from the group consisting of fruit shape, fruit weight, ripening date, fruit diameter, fruit length, pericarp thickness, soluble solids concentration, pedicel diameter, pedicel length, seed weight, firmness, and fruit color. In one embodiment, said fruit shape traits are related to blocky type fruit (bell pepper) or rectangular ¾ long type or half long fruit type. Such fruit shapes are well-known to those skilled in the art of pepper breeding. Non-limiting examples of blocky type pepper, half long type pepper, and ¾ long type pepper are shown in FIG. 6. As used herein, blocky type pepper refers to a pepper wherein the length of the fruit is about the same as the width of the fruit. For example, the length of the fruit is about 0.8, about 0.9, about 1.0, about 1.1, or less than 1.2 of the width of the fruit. As used herein, half long type pepper refers to a pepper wherein the length of the fruit is about 1.2 to about 1.5 of the width of the fruit. As used herein, ¾ long type pepper, often known as lamuyo refers to a pepper wherein the length of the fruit is more than about 1.5 of the width of the fruit. In further embodiments, said fruit traits are determined by the genes and/or QTLs described herein, e.g., those described in Wang et al., 2006, Ben Chaim 2001, Ben Chaim et al., 2003a, 2003b, Rao et al., 2003, Bachi et al. 2009, and Zygier et al., 2005. In some embodiments, said fruit traits are fruit shape ("fs") and/or fruit weight ("fw"). In some embodiments, said fruit traits are determined by the QTLs designated as fs 2.1, fs 3.1, fs 10.1, fw 2.2, fw 8.1, or a combination of any two or more said QTLs. The defining primers of fs 2.1, fs 3.1, fs 10.1, fw 2.2, and fw 8.1 are shown in Table 1 and FIG. 4.

Figure 4:
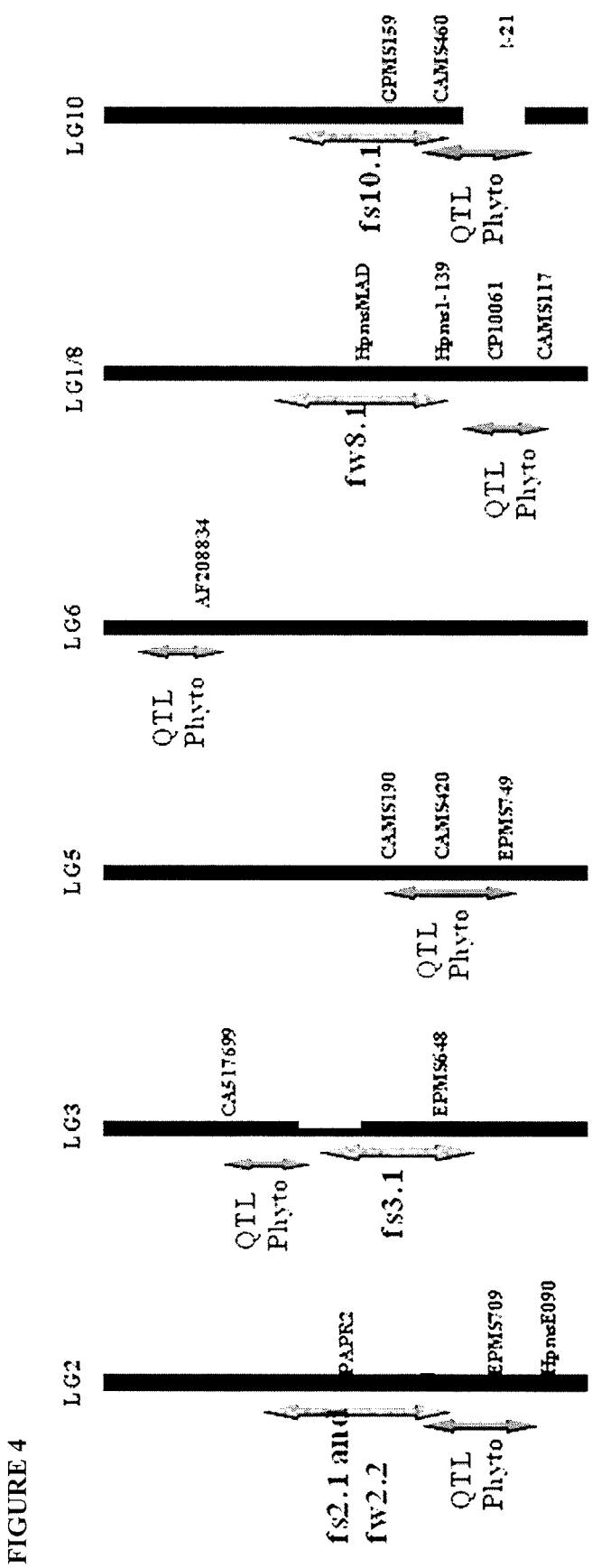

One skilled in the art would be able to design other primers for PCR detection of the molecular markers defined by the primers listed in Table 1 and FIG. 4, or methods other than PCR to detect said molecular makers (e.g., polymorphism detection methods such as nucleic acid sequencing and TIL-ING arrays).

In one embodiment, the *Capsicum* plant is a *Capsicum annuum* plant, wherein the plant has rectangular ¾ long type fruit, and wherein the plant is line '09SRTF713-5' deposited with NCIMB under No 41791 or line '09SRTF712-4'.

In one embodiment, the *Capsicum* plant is a *Capsicum annuum* plant, wherein the plant has blocky type fruit, and wherein the plant is line '09SRTF776-4' deposited with NCIMB under No 41792, or line '09SRTF737-4'.

In one embodiment, the *Capsicum* plant is a *Capsicum annuum* plant, wherein the plant has half long type fruit, and wherein the plant is line '09SRTF788-1' deposited with NCIMB under No 41793.

In further embodiments, the *Capsicum* plants of the present invention comprise one or more other agronomic traits. For example, such traits can be morphological traits (such as plant height, flaccid phenotypes, branching habits, fasciculation, leaf shape, color of plant parts, variegated seedlings, flowers, immature fruit colors, mature fruit colors, transition of fruit colors), physiological traits (such as pungency, beta-carotene contents, soft flesh and deciduous fruits), sterility traits (such as genic male sterility, cytoplasmic male sterility, functional male sterility, female sterility), and resistance to diseases, nematodes, and herbicides (such as resistance to bacterial, viral and fungal diseases, e.g., resistance to tobacco mosaic virus, resistance to cucumber mosaic virus, resistance to potyvirus, resistance to tomato spotted wilt tospovirus, resistance to bacterial leaf spot, resistance to phytophthora, resistance to anthracnose, resistance to *Ralstonia solanacearum*, resistance to powdery mildew, resistance to root knot nematodes, and bentazon herbicide tolerance).

The present invention also provides a genetically related *Capsicum* plant population (progeny) derived from the *Capsicum* plants described herein. Such genetically related *Capsicum* plant population can be produced through either natural or artificial process, sexually or asexually, e.g., by cutting, grafting, apomixis, layering, division, budding, grafting or tissue culture, wherein said progeny retains the *Phytophthora* resistance genes/QTLs and the agronomic genes/QTLs. In one embodiment, at least 5% of said progeny is resistant to *Phytophthora*. For example, about 5% to about 15%, about 16% to about 25%, about 26% to about 50%, or 51% to about 99%, or more of said progeny is resistant to *Phytophthora*.

The present invention also provides a seed, a fruit, a plant population, a plant, a plant part, a plant cell and/or a plant tissue culture derived from the plants comprising at least one, at least two, at least three, at least four, at least five or at least six of the *Phytophthora* resistance genes/QTLs, and/or at least one or more of the agronomic genes/QTLs as described above. In one embodiment, the invention provides an embryo, a pollen and/or an ovule of the plants comprising one or more of the *Phytophthora* resistance genes/QTLs and/or one or more of the agronomic genes/QTLs as described above. In one embodiment, the invention provides a rootstock, and/or a scion of the plants comprising one or more of the *Phytophthora* resistance genes/QTLs and/or one or more of the agronomic genes/QTLs as described above. The present invention also provides a tissue culture of the regenerable cells of the plants comprising one or more of the *Phytophthora* resistance genes/QTLs and/or one or more of the agronomic genes/QTLs as described above, plant parts, plant tissue or plant cells thereof, wherein said tissue culture retains one or more of the *Phytophthora* resistance genes/QTLs and/or one or more of the agronomic genes/QTLs as described above. In one embodiment, the regenerable cells are derived from embryos, protoplasts, meristematic cells, callus, pollen, leaves, anthers, stems, petioles, roots, root tips, fruits, seeds, flowers, cotyledons, or hypocotyls.

Modern plant tissue culture is performed under aseptic conditions under filtered air. Living plant materials from the environment are naturally contaminated on their surfaces (and sometimes interiors) with microorganisms, so surface sterilization of starting materials (explants) in chemical solutions (usually alcohol or bleach) is required. Explants are then usually placed on the surface of a solid culture medium, but are sometimes placed directly into a liquid medium, particularly when cell suspension cultures are desired. Solid and liquid media are generally composed of inorganic salts plus a few organic nutrients, vitamins and plant hormones. Solid media are prepared from liquid media with the addition of a gelling agent, usually purified agar.

The composition of the medium, particularly the plant hoiniones and the nitrogen source (nitrate versus ammonium salts or amino acids) have profound effects on the morphology of the tissues that grow from the initial explant. For example, an excess of auxin will often result in a proliferation of roots, while an excess of cytokinin may yield shoots. A balance of both auxin and cytokinin will often produce an unorganized growth of cells, or callus, but the morphology of the outgrowth will depend on the plant species as well as the medium composition. As cultures grow, pieces are typically sliced off and transferred to new media (subcultured) to allow for growth or to alter the morphology of the culture. The skill and experience of the tissue culturist are important in judging which pieces to culture and which to discard. As shoots emerge from a culture, they may be sliced off and rooted with auxin to produce plantlets which, when mature, can be transferred to potting soil for further growth in the greenhouse as normal plants.

The tissue obtained from the plant to culture is called an explant. Based on work with certain model systems, particularly tobacco, it has often been claimed that a totipotent explant can be grown from any part of the plant. However, this concept has been vitiated in practice. In many species explants of various organs vary in their rates of growth and regeneration, while some do not grow at all. The choice of explant material also determines if the plantlets developed via tissue culture are haploid or diploid. Also the risk of microbial contamination is increased with inappropriate explants. Thus it is very important that an appropriate choice of explant be made prior to tissue culture.

The specific differences in the regeneration potential of different organs and explants have various explanations. The significant factors include differences in the stage of the cells in the cell cycle, the availability of or ability to transport endogenous growth regulators, and the metabolic capabilities of the cells. The most commonly used tissue explants are the meristematic ends of the plants like the stem tip, auxiliary bud tip and root tip. These tissues have high rates of cell division and either concentrate or produce required growth regulating substances including auxins and cytokinins. Some explants, like the root tip, are hard to isolate and are contaminated with soil microflora that become problematic during the tissue culture process. Certain soil microflora can form tight associations with the root systems, or even grow within the root. Soil particles bound to roots are difficult to remove without injury to the roots that then allows microbial attack. These associated microflora will generally overgrow the tissue culture medium before there is significant growth of plant tissue. Aerial (above soil) explants are also rich in undesirable microflora. However, they are more easily removed from the explant by gentle rinsing, and the remainder usually can be killed by surface sterilization. Most of the surface microflora do not form tight associations with the plant tissue. Such associations can usually be found by visual inspection as a mosaic, de-colorization or localized necrosis on the surface of the explant.

An alternative for obtaining uncontaminated explants is to take explants from seedlings which are aseptically grown from surface-sterilized seeds. The hard surface of the seed is less permeable to penetration of harsh surface sterilizing agents, such as hypochlorite, so the acceptable conditions of sterilization used for seeds can be much more stringent than for vegetative tissues.

Tissue cultured plants are clones, if the original mother plant used to produce the first explants is susceptible to a pathogen or environmental condition, the entire crop would be susceptible to the same problem, conversely any positive traits would remain within the line also. Plant tissue culture is used widely in plant science; it also has a number of commercial applications. Applications include:
1. Micropropagation is widely used in forestry and in floriculture. Micropropagation can also be used to conserve rare or endangered plant species.
2. A plant breeder may use tissue culture to screen cells rather than plants for advantageous characters, e.g. pathogen resistance/tolerance.
3. Large-scale growth of plant cells in liquid culture inside bioreactors as a source of secondary products, like recombinant proteins used as biopharmaceuticals.
4. To cross distantly related species by protoplast fusion and regeneration of the novel hybrid.
5. To cross-pollinate distantly related species and then tissue culture the resulting embryo which would otherwise normally die (Embryo Rescue).
6. For production of doubled monoploid (dihaploid) plants from haploid cultures to achieve homozygous lines more rapidly in breeding programs, usually by treatment with colchicine which causes doubling of the chromosome number.
7. As a tissue for transformation, followed by either short-term testing of genetic constructs or regeneration of transgenic plants.
8. Certain techniques such as meristem tip culture can be used to produce clean plant material from infected stock, such as potatoes and many species of soft fruit.
9. Micropropagation using meristem and shoot culture to produce large numbers of identical individuals.

Non-limiting exemplary tissue culture methods for *Capsicum* plants have been described by Arous et al., 2001, Sharma, 2007, Agrawal et al., 1989, Harini and Sita, 1993, and Kothari et al., 2010, each of which is incorporated by reference in its entirety.

The present invention also provides a cutting, a rootstock, a scion, or an explant from the *Capsicum* plants as described above for grafting.

Grafting is a method of asexual plant propagation widely used in agriculture and horticulture where the tissues of one plant are encouraged to fuse with those of another. It is most commonly used for the propagation of trees and shrubs grown commercially. In most cases, one plant is selected for its roots, and this is called the stock or rootstock. The other plant is selected for its stems, leaves, flowers, or fruits and is called the scion. The scion contains the desired genes to be duplicated in future production by the stock/scion plant. In stem grafting, a common grafting method, a shoot of a selected, desired plant cultivar is grafted onto the stock of another type. In another common form called budding, a claimant side bud is grafted on the stem of another stock plant, and when it has fused successfully, it is encouraged to grow by cutting out the stem above the new bud.

For successful grafting to take place, the vascular cambium tissues of the stock and scion plants must be placed in contact with each other. Both tissues must be kept alive until the graft has taken, usually a period of a few weeks. Successful grafting only requires that a vascular connection takes place between the two tissues. A physical weak point often still occurs at the graft, because the structural tissue of the two distinct plants, such as wood, may not fuse.

Exemplary grafting techniques include, approach grafting, budding grafting (patch budding, chip budding, T-budding), cleft grafting, side grafting, whip grafting, stub grafting, awl grafting, veneer grafting, bark grafting, tongue grafting, et al. A detailed grafting method for *Capsicum* species is described by Toth et al., Kokalis-Burelle et al., 2009, and DeWitt and Bosland, 2009, each of which is incorporated by reference in its entirety.

The *Phytophthora* resistance plants with agronomic genes and/or QTLs of the present invention can be used for many purposes. In one embodiment, a plant of the present invention is used as a donor plant of genetic material which can be transferred to a recipient plant to produce a plant with desired agronomic traits which has the transferred genetic material and is also resistant to *Phytophthora*. Any suitable method known in the art can be applied to transfer genetic material from a donor plant to a recipient plant. In most cases, such genetic material is genomic material.

In one embodiment, the whole genome of the *Phytophthora* resistance plants with agronomic genes and/or QTLs of the present invention is transferred into a recipient plant. This can be done by crossing the *Phytophthora* resistant plants to a recipient plant to create a F1 plant. The F1 plant can be further selfed and selected for one, two, three, four, or more generations to give *Phytophthora* resistant plants. Selection pressure can be *Phytophthora* resistance test, molecular marker selection, agronomic traits phenotype selection, or a combination thereof.

In another embodiment, at least the resistance-conferring parts of the donor plant's genome are transferred. This can be done by crossing the *Phytophthora* resistance plants with agronomic genes and/or QTLs to a recipient plant to create a F1 plant, followed with one or more backcrosses to one of the parent plants to give the *Phytophthora* resistance plants with agronomic genes and/or QTLs with the desired genetic background. The progeny resulting from the backcrosses can be further selfed to give new *Phytophthora* resistance plants with agronomic genes and/or QTLs.

In some embodiments, the recipient plant is a *Capsicum annum* plant, or any other *Capsicum* plants that can hybridize with the *Phytophthora* resistance plants with agronomic genes and/or QTLs of the present invention.

In one embodiment, the recipient plant is an elite line having one or more certain agronomically important traits. As used herein, "agronomically important traits" include any phenotype in a plant or plant part that is useful or advantageous for human use. Examples of agronomically important traits include but are not limited to those that result in increased biomass production, increased food production, improved food quality, decrease in cracking, quicker color change when the fruit matures etc. Additional examples of agronomically important traits includes pest resistance, vigor, development time (time to harvest), enhanced nutrient content, novel growth patterns, flavors or colors, salt, heat, drought and cold tolerance, and the like.

Other agronomically important traits include resistance to biotic and/or abiotic stresses. As used herein, the phrase "biotic stress" or "biotic pressure" refers to a situation where damage is done to plants by other living organisms, such as bacteria, viruses, fungi, parasites, insects, weeds, animals and human. As used herein, the phrase "abiotic stress" or "abiotic pressure" refers to the negative impact of non-living factors on plants in a specific environment. The non-living variable must influence the environment beyond its normal range of variation to adversely affect the population performance or individual physiology of plants in a significant way. Non-limiting examples of stressors are high winds, extreme temperatures, drought, flood, and other natural disasters, such as tornados and wildfires. For example, the plant lines developed using the genetic materials and methods of the present invention can also include resistance to *Phytophthora* due to one or more different QTLs other than the QTLs described herein; resistance to other types of oomycetes other than *Phytophthora*; and/or resistance to other pathogens (e.g., fungal plant pathogens, viruses bacterial plant pathogens, insects et al.).

A list of popular North America *Capsicum* cultivars with various agronomically important traits are well known to those skilled in the art and can also be found in the Vegetable Cultivar Breeding database of North Carolina State University (Bosland, Department of Agronomy and Horticulture, New Mexico State University, Vegetable Cultivar Descriptions for North America, Pepper, Retrieved on Jun. 18, 2010, incorporated by reference in its entirety). More *capsicum* cultivars can be found in the Pepper Database of European Cooperative Program for Plant Genetic Resources (ECPGR).

In one embodiment, the recipient plants and/or lines are resistant to *Phytophthora* due to one or more different genes or QTLs other than the ones described in the present invention. In some embodiments, said different genes/QTLs are any genes/QTLs that are different from the six *Phytophthora* resistance QTLs found in 'CM334', which are designated as P1/8, P2, P3, P5, P6, and P10. For example, such genes/QTLs can be derived from *Capsicum* species that are resistant to *Phytophthora* other than *Capsicum annum*, or from *Capsicum annum* plants other than 'CM334'.

In one embodiment, the recipient plants and/or lines have one or more preferred traits related to resistance/tolerance to pathogens, such as resistance to pests (e.g., thrips, aphids, caterpillars, and whiteflies), fungus (e.g., Pythium, Rhizoctonia, Leveillula, *Verticillium* wilt (*Verticillium dahliae*), Southern blight (*Sclerotium rolfsii*), Ripe rot (*Vermicularia capsici*), Cercospora leaf spot (*Cercospora capsici*), Anthracnose (*Gleosporium piperatum*)), bacteria (e.g., *Xanthomonas vesicatoria, Xanthomonas campestris*), viruses (e.g., Cucumber mosaic virus (CMV), Tobacco mosaic virus (TMV), Potato virus Y (PVY), Tobacco etch virus (TEV), Pepper mottle virus (PeMV), Tomato spotted wilt virus (TSWV), Tobacco mild virus (TOMV), Pepper mild mottle virus (PMMoV) and nematodes (e.g., root-knot nematode).

Methods of Producing *Capsicum* Plants Resistant to *Phytophthora capsici* with Agronomic Traits Any *Capsicum* plant with *Phytophthora* resistant QTLs and agronomic QTLs of the present invention can be used to produce more *Capsicum* plants that are resistant to *Phytophthora* with agronomic trains through plant breeding methods well known to those skilled in the art. The goal in general is to develop new, unique and superior varieties and hybrids. In some embodiments, selection methods, e.g., molecular marker assisted selection, can be combined with breeding methods to accelerate the process.

Choice of breeding or selection methods depends on the mode of plant reproduction, the heritability of the trait(s) being improved, and the type of cultivar used commercially (e.g., F1 hybrid cultivar, pure line cultivar, etc.). For highly heritable traits, a choice of superior individual plants evaluated at a single location will be effective, whereas for traits with low heritability, selection should be based on mean values obtained from replicated evaluations of families of related plants. Non-limiting breeding methods commonly include pedigree selection, modified pedigree selection, mass selection, recurrent selection, and backcross breeding.

The complexity of inheritance influences choice of the breeding method. Backcross breeding is used to transfer one or a few favorable genes for a heritable trait into a desirable cultivar. This approach has been used extensively for breeding disease-resistant cultivars, nevertheless, it is also suitable for the adjustment and selection of morphological characters, color characteristics and simply inherited quantitative characters. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s) for three years at least. The best lines are candidates for use as parents in new commercial cultivars; those still deficient in a few traits may be used as parents to produce new populations for further selection.

In one embodiment, said method comprises (i) crossing any one of the *Capsicum* plants with *Phytophthora* resistant QTLs and agronomic QTLs of the present invention as a donor to a recipient plant line to create a F1 population; (ii) evaluating *Phytophthora* resistance and/or agronomic phenotypes in the offsprings derived from said F1 population; and (iii) selecting offsprings that are resistant to *Phytophthora* with desired agronomic traits.

To select *Phytophthora* resistant plants in the offsprings, a *Phytophthora* resistant control plant and/or a *Phytophthora* susceptible control plant are involved. The population of the control plant is also challenged with a *Phytophthora* strain, under similar environmental conditions and pest or pathogen pressure. Resistance level of the offsprings, plant tissue or plant cell thereof is compared to the resistance level of the control plant, plant tissue or plant cell.

To select plants with desired agronomic traits, an elite control plant can be involved for comparison. Desired agronomic traits, such as fruit weight and fruit shape can be compared among the population under selection and the elite control plant.

In one embodiment, the selection can be combined with molecular marker selection for desired *Phytophthora* resistance genes/QTLs and/or agronomic genes/QTLs.

In one embodiment, the evaluating step comprises visual observation to determine the severity of the pathogen infection, using a resistance scoring system. The resistance scoring system is well known in the art and is described elsewhere herein.

A plant population is resistant if it has at least 60%, at least 65%, at least 70%, at least 75%, at least 80%, at least 85%, at least 90%, at least 95%, at least 98%, at least 99%, at least 99.5%, or 100% of the plants in the least symptomatic levels of 0, 1, and 2 using the rating system as described in more detail elsewhere herein. In one embodiment, a plant population is resistant if it has at least about 60% of the plants in the least symptomatic levels of 0, 1, and 2. In another embodiment, a plant population is resistant if it has at least about 70% of the plants in the least symptomatic levels of 0, 1, and 2. In another embodiment, a plant population is highly resistant if it has at least about 80% of the plants in the least symptomatic levels of 0, 1, and 2. In another embodiment, a plant population is extremely resistant if it has at least about 90% of the plants in the least symptomatic levels of 0, 1, and 2.

A plant population is susceptible if it has at least 40%, at least 45%, at least 50%, at least 55%, at least 60%, at least 65%, at least 70%, at least 75%, at least 80%, at least 85%, at least 90%, at least 95%, at least 98%, at least 99%, at least 99.5%, or 100% of the plants in the most symptomatic levels of 3 and 4 using the rating system as described in more detail elsewhere herein. In one embodiment, a plant population is susceptible if it has at least about 40% of the plants in the most symptomatic levels of 3 and 4. In another embodiment, a plant population is susceptible if it has at least about 50% of the plants in the most symptomatic levels of 3 and 4. In another embodiment, a plant population is susceptible if it has at least about 60% of the plants in the most symptomatic levels of 3 and 4. In another embodiment, a plant population is susceptible if it has at least about 70% of the plants in the most symptomatic levels of 3 and 4.

In another embodiment, said evaluating step comprises one or more molecular biological tests of *Phytophthora* density in the plants. In one embodiment, said molecular biological tests comprise testing the density of *Phytophthora*-specific nucleic acid sequence and/or *Phytophthora*-specific protein. For example, the molecular biological test can involve probe hybridization and/or amplification of nucleic acid (e.g., measuring viral nucleic acid density by Northern or Southern hybridization, RT-PCR) and/or immunological detection (e.g., measuring viral protein density, such as precipitation and agglutination tests, ELISA (e.g., Lateral Flow test or DAS-ELISA), Western blot, RIA, immunogod labeling, immunosorbent electron microscopy (ISEM), and/or dot blot). For example, a plant may be resistant to a *Phytophthora* strain if it has a *Phytophthora* nucleic acid and/or protein density that is about 50%, about 40%, about 30%, about 20%, about 10%, about 5%, about 2%, about 1%, about 0.1%, about 0.01%, about 0.001%, or about 0.0001% of the *Phytophthora* nucleic acid and/or protein density in a susceptible plant.

The procedure to perform a nucleic acid hybridization, an amplification of nucleic acid (e.g., RT-PCR) or an immunological detection (e.g., precipitation and agglutination tests, ELISA (e.g., Lateral Flow test or DAS-ELISA), Western blot, RIA, immunogod labeling, immunosorbent electron microscopy (ISEM), and/or dot blot tests) are performed as described elsewhere herein and well-known by one skilled in the art. For example, Bilodeau et al. (Sudden Oak Death Second Science Symposium: The State of Our Knowledge, Jan. 18 to 21, 2005, Monterey, Calif.) and Chandelier et al. (2006, OEPP/EPPO, Bulletin OEPP/EPPO Bulletin 36:409-414) describe molecular detection of *Phytophthora ramorum* by Real-Time PCR. Silver et al. (2005, The American Phytopathological Society, DOI: 10.1094/PHYTO-95-1423, 95(12): 1423-1429) describes using Real-Time PCR to quantify *Phytophthora capsici* in different pepper genotypes. One skilled in the art would be able to design tests for the molecular detection of other *Phytophthora* species.

In one embodiment, the evaluating step comprise RT-PCR (semi-quantitative or quantitative), wherein *Phytophthora*-specific primers are used to amplify one or more *Phytophthora*-specific nucleic acid sequences. In one embodiment, said *Phytophthora*-specific nucleic acid sequences are from the same gene of *Phytophthora*. In another embodiment, said *Phytophthora*-specific nucleic acid sequences are from different genes of *Phytophthora*. In one embodiment, said RT-PCT is a real-time RT-PCT.

In another embodiment, the evaluating step comprises immunological detection (e.g., precipitation and agglutination tests, ELISA (e.g., Lateral Flow test or DAS-ELISA), Western blot, RIA, immunogod labeling, immunosorbent electron microscopy (ISEM), and/or dot blot), wherein one or more *Phytophthora*-specific antibodies are used to detect one or more *Phytophthora*-specific proteins. In one embodiment, said *Phytophthora*-specific antibody is selected from the group consisting of polyclonal antibodies, monoclonal antibodies, and combination thereof. For example, Miller et al. (1994, Detection of *Phytophthora capsici* in pepper and cucurbit crops in Ohio with two commercial immunoassay kits, Plant disease, 78(11):1042-1046) and O'Brien et al. (2009, Detecting *Phytophthora*, Critical Reviews in Microbiology, Vol. 35, No. 3, Pages 169-181) describe detection of *Phytophthora* using ELISA.

Reverse Transcription Polymerase Chain Reaction (RT-PCR) can be utilized in the present invention to determine the pathogen RNA density in a plant. It is a variant of polymerase chain reaction (PCR), a laboratory technique commonly used in molecular biology to generate many copies of a DNA sequence, a process termed "amplification". In RT-PCR, however, RNA strand is first reverse transcribed into its DNA complement (complementary DNA, or cDNA) using the enzyme reverse transcriptase, and the resulting cDNA is amplified using traditional or real-time PCR.

RT-PCR utilizes a pair of primers, which are complementary to a defined sequence on each of the two strands of the cDNA. These primers are then extended by a DNA polymerase and a copy of the strand is made after each cycle, leading to logarithmic amplification.

RT-PCR includes three major steps. The first step is the reverse transcription (RT) where RNA is reverse transcribed to cDNA using a reverse transcriptase and primers. This step is very important in order to allow the performance of PCR since DNA polymerase can act only on DNA templates. The RT step can be performed either in the same tube with PCR (one-step PCR) or in a separate one (two-step PCR) using a temperature between 40° C. and 50° C., depending on the properties of the reverse transcriptase used.

The next step involves the denaturation of the dsDNA at 95° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cations concentration. The main consideration, of course, when choosing the optimal annealing temperature is the melting temperature (Tm) of the primers and probes (if used). The annealing temperature chosen for a PCR depends directly on length and composition of the primers. This is the result of the difference of hydrogen bonds between A-T (2 bonds) and G-C (3 bonds). An annealing temperature about 5 degrees below the lowest Tm of the pair of primers is usually used.

The final step of PCR amplification is the DNA extension from the primers which is done by the thermostable Taq DNA polymerase usually at 72° C., which is the optimal temperature for the polymerase to work. The length of the incubation at each temperature, the temperature alterations and the number of cycles are controlled by a programmable thermal cycler. The analysis of the PCR products depends on the type of PCR applied. If a conventional PCR is used, the PCR product is detected using agarose gel electrophoresis and ethidium bromide (or other nucleic acid staining).

Conventional RT-PCR is a time-consuming technique with important limitations when compared to real time PCR techniques. This, combined with the fact that ethidium bromide has low sensitivity, yields results that are not always reliable. Moreover, there is an increased cross-contamination risk of the samples since detection of the PCR product requires the post-amplification processing of the samples. Furthermore, the specificity of the assay is mainly determined by the primers, which can give false-positive results. However, the most important issue concerning conventional RT-PCR is the fact that it is a semi or even a low quantitative technique, where the amplicon can be visualized only after the amplification ends.

Real time RT-PCR provides a method where the amplicons can be visualized as the amplification progresses using a fluorescent reporter molecule. There are three major kinds of fluorescent reporters used in real time RT-PCR, general non specific DNA Binding Dyes such as SYBR Green I, TaqMan Probes and Molecular Beacons (including Scorpions).

The real time PCR thermal cycler has a fluorescence detection threshold, below which it cannot discriminate the difference between amplification generated signal and background noise. On the other hand, the fluorescence increases as the amplification progresses and the instrument performs data acquisition during the annealing step of each cycle. The number of amplicons will reach the detection baseline after a specific cycle, which depends on the initial concentration of the target DNA sequence. The cycle at which the instrument can discriminate the amplification generated fluorescence from the background noise is called the threshold cycle (Ct). The higher is the initial DNA concentration, the lower its Ct will be.

In one embodiment, protoplast fusion can be used for the transfer of resistance-conferring genomic material and agronomic traits conferring genomic material from a donor plant to a recipient plant. Protoplast fusion is an induced or spontaneous union, such as a somatic hybridization, between two or more protoplasts (cells of which the cell walls are removed by enzymatic treatment) to produce a single bi- or multinucleate cell. The fused cell, that may even be obtained with plant species that cannot be interbred in nature, is tissue cultured into a hybrid plant exhibiting the desirable combination of traits. More specifically, a first protoplast can be obtained from a plant line that is resistant to *Phytophthora* with desired agronomic traits. A second protoplast can be obtained from a susceptible second plant line, optionally from another plant species or variety, preferably from the same plant species or variety, which comprises commercially desirable characteristics, such as, but not limited to disease resistance, insect resistance, valuable fruit characteristics, etc. The protoplasts are then fused using traditional protoplast fusion procedures, which are known in the art to produce the cross.

Alternatively, embryo rescue may be employed in the transfer of resistance-conferring genomic material and agronomic traits conferring genomic material from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (see Pierik, 1999, *In vitro culture of higher plants*, Springer, ISBN 079235267x, 9780792352679, which is incorporated herein by reference in its entirety).

In addition, in one embodiment, a method for producing a *Phytophthora* resistant plant with desired agronomic traits comprises grafting a susceptible recipient plant onto resistant rootstocks of the donor plants, which is proved to be an effective methodology developed for intensive cultivation in the Far East (Lee and Oda, 2003, Grafting of herbaceous vegetable and ornamental crops, *Hort. Rev.* 28:61-124). As described before, the recipient plant can be an elite line having certain favorite traits.

In addition, in one embodiment, a method for producing a *Phytophthora* resistant plant with desired agronomic traits comprises grafting a resistant scion plant onto susceptible rootstocks plants. As described before, the susceptible plant can be an elite line having certain favorite traits.

Breeding Methods

Open-Pollinated Populations.

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection.

In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics.

A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

Hybrids.

A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

Bulk Segregation Analysis (BSA).

BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences, USA*, 99:9828-9832) and Quarrie et al. (Quarrie et al., Bulk segregant analysis with molecular markers and its use for improving drought resistance in maize, 1999, *Journal of Experimental Botany*, 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to pathogen), and the other from the individuals having reversed phenotype (e.g., susceptible to pathogen), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

Gene Pyramiding.

Figure 3:
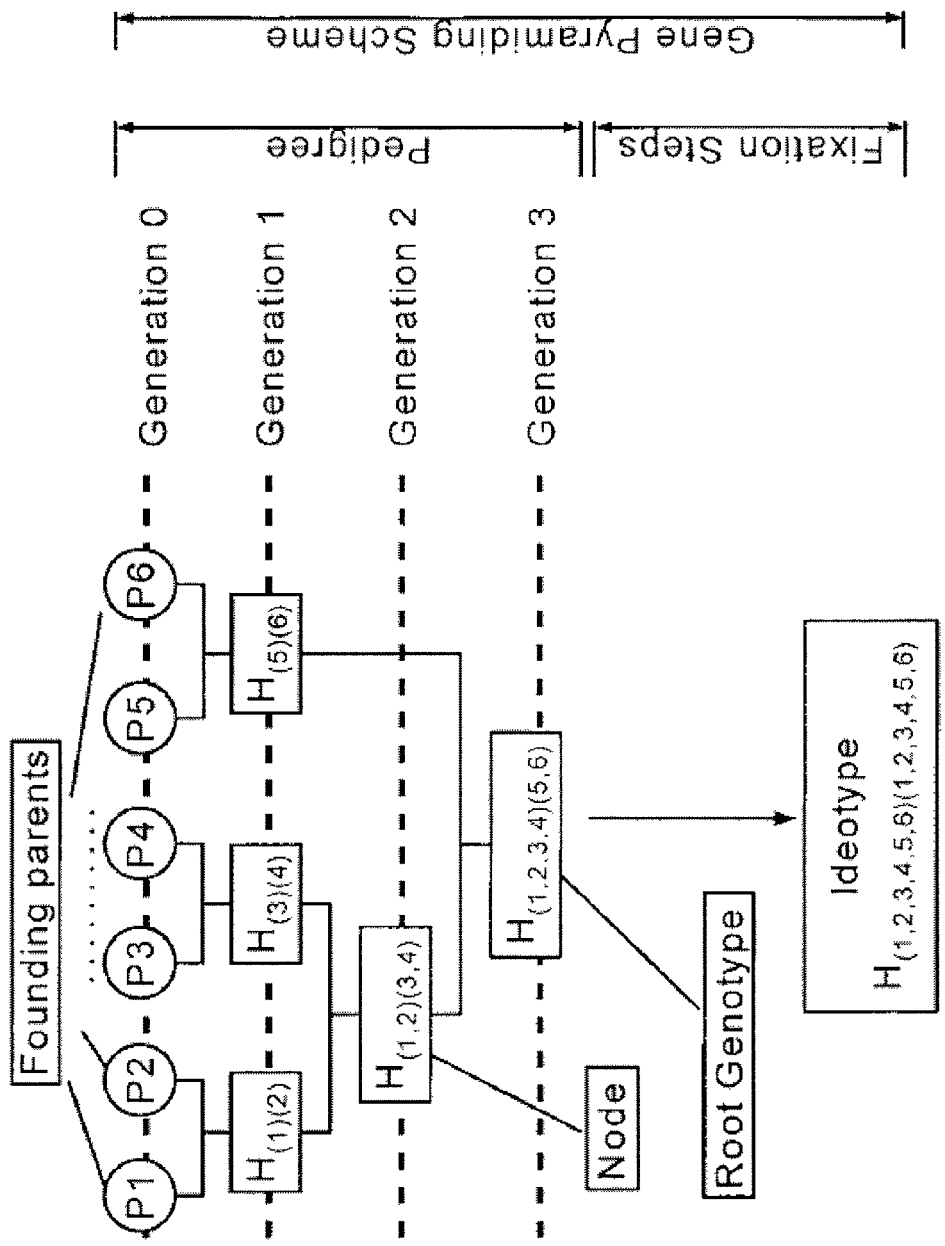

The method to combine into a single genotype a series of target genes identified in different parents is usually referred as gene pyramiding. A non-limiting example of gene pyramiding scheme is shown in FIG. 3. The first part of a gene pyramiding breeding is called a pedigree and is aimed at cumulating one copy of all target genes in a single genotype (called root genotype). The second part is called the fixation steps and is aimed at fixing the target genes into a homozygous state, that is, to derive the ideal genotype (ideotype) from the root genotype. Gene pyramiding can be combined with marker assisted selection (MAS, see Hospital et al., 1992, 1997a, and 1997b, and Moreau et al, 1998) or marker based recurrent selection (MBRS, see Hospital et al., 2000).

DEPOSIT INFORMATION

A deposit of the pepper seed of this invention is maintained by Clause, Rue Louis Saillant, ZI La Motte, 26800 Porte Les Valence, France. In addition, a sample of the pepper seed of this invention has been deposited with the National Collections of Industrial, Food and Marine Bacteria (NCIMB), 23 St Machar Drive, Aberdeen, Scotland, AB24 3RY, United Kingdom To satisfy the enablement requirements of 35 U.S.C. §112, and to certify that the deposit of the seeds of the present invention meets the criteria set forth in 37 C.F.R. §§1.801-1.809, Applicants hereby make the following statements regarding the deposited pepper seed 09SRTF713-5, 09SRTF776-4 and 09SRTF788-1 (deposited as NCIMB Accession No. 41791, 41792 and 41793, respectively):

1. During the pendency of this application, access to the invention will be afforded to the Commissioner upon request;
2. Upon granting of the patent the seeds will be available to the public under conditions specified in 37 CFR 1.808;
3. The deposit will be maintained in a public repository for a period of 30 years or 5 years after the last request or for the enforceable life of the patent, whichever is longer; and
4. The viability of the biological material at the time of deposit will be tested; and
5. The deposit will be replaced if it should ever become unavailable.

Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same seed source with the NCIMB.

It should be understood that the examples and embodiments described herein are for illustrative purposes only and that various modifications or changes in light thereof will be suggested to persons skilled in the art and are to be included within the spirit and purview of this application.

EXAMPLES

Material and Methods

Pathogen Collection and Phenotypic Evaluation

The initial isolate collection was obtained over several years from different *Capsicum annum* cultivation areas, including California, Florida, New Jersey, Mexico, Italy, Thailand, Spain, China and France. Each was isolated from samples with specific symptoms collected in the field and was identified according to the Koch postulates and confirmed by specific PCR identification (from Cooke et al, 2000).

Two other isolates were used "routinely" for resistance characterization: 'N101' (for screening for relatively low to moderate levels of resistance) and 'S197' (more aggressive/virulent isolate used to identify stronger levels of resistance). Both isolates were obtained from INRA Montfavet (E. Pochard team) and are described and used as reference strains in several of the publications cited elsewhere herein.

Some of the hybrids/lines of the present invention and some commercially available hybrids were infected with this collection of different isolates (see Table 3). The resistant controls are 'CM 334' (the best available level of resistance) and '08SR912 (a line originating from 'PI201234' and having a medium level of resistance); the susceptible control is 'Yolo Wonder'.

The Stem Decapitation Test

Fungi are cultivated on V8 agar medium in Petri box (V8 juice 200 ml/l, CaCO3 2 g/l, Agar 17 g/l, 5 ml/l of antibiotics solution=Penicilline 0.25%, Polymixine 0.025%, Benomyl 0.015%, parachloronitrobenzene 0.1%) and a plug is put down on the section of a stem cut below the 5th leaf. A cylinder of foil recovers this construction and keeps the humidity necessary for mycelium penetration and propagation in the plant tissue. Resistance evaluation is based on the number of falling leaves when the susceptible check is dead (usually 2 weeks after inoculation).

The Root Inoculation Test (Bosland et Lindsey, 1991)

Plantlets are inoculated when the roots are well developed (6 to 8 weeks after sowing): 5 ml of a solution containing 2000 zoospores/mL are poured at the foot of each plantlet. When the susceptible checks are dead (usually 7 to 15 days post-inoculation), the resistance evaluation is done on per plant basis according to a notation scale from 0 (no necrosis) to 5 (plant death).

DNA Extraction and Genotyping Protocol

The plant DNA extraction was realized with the PL2-PL3 extraction kit (Macherey-Nagel). These solutions permit both the lysis and the purification steps. The precipitation and cleaning steps was done with isopropanol and ethanol 70% solutions, respectively.

The DNA (5 µL, 1/5 dilution) was pooled with a rectional volume of 54 containing MgCl2 (2.5 mM), dNTP (0.25 mM), buffer (1×), primers (0.025 µM for the forward primer and 0.1 µM for the reverse primer) and the Taq Polymerase (0.5 U) (Invitrogen™)

Sequences of primers used for screening are presented in the Table 1. The PCR cycler protocol is as follows: Pre-denaturation—2 min at 95° C.; Denaturation—30 sec at 95° C.; Hybridization—30 sec at 50° C. 35 times; Elongation—30 sec at 72° C.; and End of Elongation—10 min at 72° C.

Then, PCR products were injected in an ABI 3730 sequencer and the SSR profiles were analyzed with the Genemaper software.

TABLE 1

SSR primers linked to *P. capsici* resistance QTLs and to agronomic QTLs used for genotyping

| Forward Primer | | Reverse primer | | Product size F7/'07SRTC1802' |
|---|---|---|---|---|
| PAPR2-F (SEQ ID NO. 1) | CCGCTTTACAAGCGGATAGTTACGTG | PAPR2-R (SEQ ID NO. 2) | CACCTTTCTTAGTTTATTCGAATAC | 281/279 |
| EPMS-709-F (SEQ ID NO. 3) | ACGCCGAGGACTATGATGAC | EPMS-709-R (SEQ ID NO. 4) | TTCTTCATCCTCAGCGTGTG | 283/297 |
| HpmsE090-F (SEQ ID NO. 5) | CACCGGCCGTTTAAACTTTCAC | HpmsE090-R (SEQ ID NO. 6) | GCTGGAGTTTCCAAAGGACAAA | 207/205 |
| CA517699-F (SEQ ID NO. 7) | ACGCCAAGAAAATCATCTCC | CA517699-R (SEQ ID NO. 8) | CCATTGCTGAAGAAAATGGG | 168/182 |
| EPMS-648-F (SEQ ID NO. 9) | TGTAAAATAAAATAAGGCTAAAGGCA | EPMS-648-R (SEQ ID NO. 10) | CAAGAAAGTGTGCCCCAAAT | 188/186 |
| CAMS_190-F (SEQ ID NO. 11) | TTTCTGCAGTGTTACCAATATTTCA | CAMS_190-R (SEQ ID NO. 12) | CCCATGGGTCCTACCTCAG | 237/239 |
| CAMS_420-F (SEQ ID NO. 13) | CAGCGTTCTATCGTCTCAAATG | CAMS_420-R (SEQ ID NO. 14) | TTGACAAACCAGAAATTGATCG | 224/222 |

TABLE 1-continued

SSR primers linked to P. capsici resistance QTLs and to agronomic QTLs used for genotyping

| Forward Primer | | Reverse primer | | Product size F7/'07SRTC1802' |
|---|---|---|---|---|
| EPMS-749-F (SEQ ID NO. 15) | TCCCACGAGTCTTTTTGAGG | EPMS-749-R (SEQ ID NO. 16) | AAAGGGAATTATGGGGTTGG | 290/284 |
| AF208834-F (SEQ ID NO. 17) | TGCACCAAGGTCCAGTAAGGTTG | AF208834-R (SEQ ID NO. 18) | CCAACCACCATGGTTCATACAAG | 228/224 |
| HpmsMADS-F (SEQ ID NO. 19) | TGCTTTCAAAACAATTTGCATGG | HpmsMADS-R (SEQ ID NO. 20) | GCGTCTAATGCAAAACACACATTAC | 216/222 |
| CP10061-F (SEQ ID NO. 21) | ATCCCAAAAGGCAAAATC | CP10061-R (SEQ ID NO. 22) | ATCCCAAAAGGCAAAATC | 177/181 |
| CAMS117-F (SEQ ID NO. 23) | TTGTGGAGGAAACAAGCAAA | CAMS117-R (SEQ ID NO. 24) | CCTCAGCCCAGGAGACATAA | 240/238 |
| GPMS 159-F (SEQ ID NO. 25) | AAGAACATGAGGAACTTTAACCATG | GPMS 159-R (SEQ ID NO. 26) | TTCACCCTTCTCCGACTCC | 312/309 |
| CAMS460-F (SEQ ID NO. 27) | CCTTTCACTTCAGCCCACAT | CAMS460-R (SEQ ID NO. 28) | ACCATCCGCTAAGACGAGAA | 235/237 |

Example 1

Recurrent Selection Breeding From 'PI201234'

A recurrent selection strategy using 'PI201234' as the donor parent for resistance to *P. capsici* was undertaken in sweet bell pepper with limited success. Using moderately virulent *P. capsici* isolate/strain 'N101' and a stem decapitation test, several elite-type pepper lines with medium levels of resistance to *P. capsici* were obtained.

Feedback from field observations led to the conclusion that the medium levels of resistance attained in these lines was not sufficient enough for commercial use and therefore that the artificial test used was not predictive enough of the field behaviour of the plants to be used in such a recurrent breeding program.

Example 2

Recurrent Selection Breeding from 'Cm334'

Next, a recurrent pyramiding selection program using 'CM334' and an elite line obtained from the recurrent selection strategy using 'PI201234' (see Example 1) was undertaken in an effort to accumulate all the resistance QTLs into the same plant. A F7 line 05SRTF569-5 with a very good level of resistance was obtained using aggressively virulent *P. capsici* isolate/strain 'S197' and a stem decapitation test. Unfortunately, however, this F7 line has a commercially undesirable long horn type fruit with a thin flesh.

Without wishing to be bound by a particular theory, the difficulty in recovering an agronomically-acceptable blocky fruit type plant with higher levels of resistance was most likely the result of linkage drags of undesirable traits from the small pungent elongated sources (i.e., 'CM334' and 'PI201234') as well as to the relatively large number of loci/QTLs involved in resistance to *P. capsici*. Even after few cycles of intercrossing, the phenotyping pressure had not allowed the improvement of the agronomic value of the resistant plants which were obtained, unless it was acceptable to only maintain plants with a medium level of resistance.

Example 3

Marker Assisted Introgression of *Phytophthora* Resistances QTLs

Based upon what was learned from Examples 1 and 2, a breeding scheme was instituted using QTLs with the goal to develop commercial elite sweet bell pepper lines with a high level of resistance to *Phytophthora*. In an effort to avoid the genetic drift of the elite line by introducing QTLs from a small fruited and pungent line, molecular markers were used to introgress resistance QTLs and to break linkage with undesirable agronomic traits (especially undesirable fruit shape and lower fruit weight QTLs) and accelerate the recovery of recipient lines with desirable agronomic traits for the commercial market. In general, the selection scheme comprised a first step based on disease resistance and a second step based on agronomic value.

An elite line ('07SRTC1802') with small plant stature, elite blocky type fruit shape/weight and having *P. capsici* resistance QTLs P5 and P10 was crossed with a F7 line 05SRTF569-5 obtained according to Example 2. '07SRTC18020 has the line 08SR912 in its genetic background. The F7 line has tall plant stature, horn type fruit with thin flesh, i.e. +/−3 mm (wile plant with thick flesh have 4-5 mm and more) and *P. capsici* resistance QTLs P5 and P6.

The resultant F1 seeds from the '07SRTC1802'× 05SRTF569-5 crossing were germinated, plants grown from the germinated seeds, and the resultant plants were selfed to produce F2 seeds/plants for further selection and breeding. Two hundred eighty eight (288) segregating F2 plants were screened for plants having the following QTLs as indicated by the presence of certain SSR: (1) QTL P6 from 'CM334' at homozygous state; (2) QTL P5 from 'CM334' or '08SR912' at homozygous state; (3) QTL P10 from '08 SR912' at homozygous or heterozygous state; and (4) fw 2.2, fs 3.1 and fw 8.1 QTLs for fruit weight/shape ("fw" or "fs", respectively). These QTLs are described in various publications as well as being known to those skilled in the art of pepper breeding (see, e.g., Thabuis et al., 2003, 2004a, 2004b and Ben Chaim et al., 2001, 2003a, 2003b, Rao et al., 2003, Zygier et al., 2005, and Barchi et al., 2009). See, also, FIG. 4.

Thirty (30) F2 plants out of the 288 F2 plants were selected based on the above criteria and then subjected to the stem decapitation test using the highly virulent *P. capsici* strain 'S197'. Based on the disease screening, 12 resistant F2 plants were selected and evaluated for agronomic traits (fruit and plant architecture) and the following 4 F2 plants were selected for further research and breeding: 'F2.120', 'F2.137', 'F2.202' and 'F2.259'. The agronomic gain was significantly visible with the four selected families having large shoulder fruits on the selected F2 plants. Table 2 provides the determined homozygosity for each of the screened QTLs.

TABLE 2

Homozygosity of QTLs in Selected F2 Plants

| Plant | P5 | P6 | P10 | f.w 2.2 | f.w 3.1 | f.w 8.1 |
|---|---|---|---|---|---|---|
| F2.120 | homo (CM334) | homo (CM334) | heteo (CM334) | heteo | homo | homo |
| F2.137 | homo (08SR912) | homo (CM334) | hete (CM334) | heteo | homo | heteo |
| F2.202 | homo (CM334) | homo (CM334) | N/A | homo | heteo | homo |
| F2.259 | homo (CM334) | homo (CM334) | heteo (CM334) | heteo | heteo | heteo |

Note:
"homo" stands for homozygous, and "heteo" stands for heterozygous.

F3 progenies derived from F2.120 (progeny 590), F2.137 (progeny 591), F2.202 (progeny 589), and F2.259 (progeny 592) were further tested for fixation with markers of QTL P10 and combined fruit weight/shape QTLs. One hundred ninety two (192) F3 plants were pre-selected with molecular markers and 40 F3 plants thereof were tested for *Phytophthora* resistance using the stem decapitation test. Thirteen (13) F3 plants were selected based on their agronomic value and *Phytophthora* resistance phenotype (evaluated by the numbers of fallen leaves, see method described elsewhere herein).

The same selection cycle was conducted again with two other F3 progenies (progeny 672 from F2.202 and progeny 673 from F2.120). In total 192 F3 plants for each progeny were tested for fixation with makers of QTL P10 and fruit weight/shape QTLs. Forty (40) F3 plants of each progeny presenting interesting QTL combinations were tested for *Phytophthora* resistance using the stem decapitation test. Seventeen (17) F3 plants showing good *Phytophthora* resistance data were selected based on evaluation of agronomic traits and the F4 seeds produced from these plants were collected. At this stage, it was clear based on the experiments conducted to date that more than 3 '334' QTLs are involved in the high level of resistance to the 'S197' isolate and it was also evident that these QTLs were slowing down the recovery of blocky shape fruits with large shoulder.

Since it appeared that more than 3 'CM334' QTLs are involved in the high level of resistance to the 'S197' isolate, a mapping approach using selected resistant F4 plants was carried out. Forty (40) plants of each of 8 F4 families were submitted to a stem decapitation test with the 'S197' isolate. The 8 F4 families included the following: F2.202=F3-672s4 and F672s5; F.120=F3.673s2, F3.673s3, F3.673s5, F3.673s7, F3.673s8 and F3.673s10. At this step, *P. capsici* resistance QTLs on P2, P3 and P1/8 were identified. The co-localization of these QTLs with fruit shape and fruit weight QTLs led us to look for the favourable recombinant event around the 'CM334' QTL. Molecular markers were used to select 20 F4 plants among the 65 F4 resistant plants (presenting a 0-1 disease symptom index as measured by leaf fallen phenotype). F5 seed was harvested from 6 F4 plants selected for the next cycle.

Two (2) replicates of 10 plants of each of the 6 selected F5 families were observed for phenotypic characteristics. The agronomic observations were conducted in a tunnel in the Roumagne location of Southwest France and confirmed the positive genetic progress of the selected plants which now had fruits with a good blocky shape, having an average weight near the original agronomic line ('07SRTC1802'). Some loss of fruit smoothness was observed and, while not wishing to be bound to any particular theory, appeared to be linked to Linkage Group 6 (LG6).

In parallel to this breeding work, it was decided to start a collection of different isolates from different world markets, and to identify these isolates via a set of reference lines, including the classical resistance sources ('CM334', 'PI1201234'), private lines, internal F1, and/or competitor F1 (see Table 3). This worldwide collection of different isolates allowed characterization of the level of resistance of the pyramiding schema. As discussed above, all steps of the breeding process to date employed a pathology test (whether a stem decapitation test or a root infection test) using the highly virulent 'S197' strain of *Phytophthora capsici*.

TABLE 3

Initial screening of hybrids/lines and commercial checks (right-hand vertical column) against the *Phytophthora* isolate collection (top horizontal row).

| | 1Z2 | N 101 | Italie 07 | Californie 1-07 | New Jersey | S 197 | Californie 2-07 | Floride 07 | France 07 | Mexique 07 |
|---|---|---|---|---|---|---|---|---|---|---|
| Yolo jaune | 0 | 4 | 2 | 3 | 4 | 4 | 4 | 4 | 4 | 3 |
| Aristotle | 0 | 3 | 1 | 2 | 3 | 3 | 3 | 4 | 4 | 1 |
| Alliance | 1 | 1 | 1 | 2 | 4 | 3 | 3 | 4 | 4 | 2 |
| 07SRTC18020 | 1 | 0 | 0 | 3 | 3 | 2 | 3 | 4 | 3 | 2 |
| Paladin | 0 | 0 | 0 | 1 | 2 | 3 | 3 | 3 | 3 | 1 |
| Révolution | 0 | 0 | 0 | 2 | 2 | 3 | 3 | 2 | 3 | 1 |
| Zenel | 0 | 0 | 0 | 2 | 2 | 3 | 3 | 3 | 3 | 2 |
| Alzon | 0 | 0 | 1 | 1 | 2 | 3 | 3 | 1 | 3 | 1 |
| 08SR912 | 1 | 0 | 0 | 0 | 0 | 2 | 2 | 1 | 1 | 1 |
| CM 334 | 0 | 0 | 0 | 0 | 0 | 0 | 0 | 0 | 0 | 0 |

The numbers indicate the levels of susceptibility (i.e., the number of fallen leaves through stem decapitation test as described in the Materials and Methods). Both 'CM 334' and 08SR912' show good levels of resistance to all isolates, including the most virulent one 'S197'.
4 From 3 to 4 leaves necrosed
3 From 2 to 3 leaves necrosed
2 From 1 to 2 leaves necrosed
1 From 0 to 1 leaf necrosed
0 no leaf necrosed/fallen Six (6) F6 progenies of F5 plants retained after agronomic evaluation were tested with 3 aggressive isolates ('S197', 'Floride 07' and 'New Jersey'). Both the stem test and the root inoculation test (Borland et al., 1991) were used and showed similar results: the F6 plants have a stronger level of resistance than all the other existing F1 (competitors), most likely due to the recessive heritability of relevant QTLs, and a level of resistance equivalent to the 'CM334' origin and better than 08SR912 (data not provided).

The F7 progenies obtained from the F6 plants were infected with 5 more aggressive isolates ('Mexique 2-07', 'France 2-09', 'Floride 07', 'Shandong 09' and 'S197'). Results on lines '09SRTF776-4', '09SRTF712-4', '09SRTF713-5', '09SRTF737-4' and '09SRTF788-1' are presented in Table 4. All five F7 lines are sister lines.

TABLE 4

Screening of the F7 selections with the collection of the five most aggressive isolates progenies as compared to competitor hybrids

| | Floride 07 | | Mexique 2-07 | | France 2-09 | | Shandong 09 | | S197 | |
|---|---|---|---|---|---|---|---|---|---|---|
| Genotype | Root test | Stem test | Root test | Stem test | Root test | Stem test | Root test | Stem test | Root test | Stem test |
| 09SRTF776-4 | 1 | 2 | 0 | 3 | 1 | 2 | 0 | 2 | 0 | 2 |
| 09SRTF712-4 | 1 | 1 | 1 | 2 | 1 | 2 | 0 | 2 | 0 | 2 |
| 09SRTF713-5 | 1 | 1 | 1 | 2 | 1 | 1 | 0 | 2 | 0 | 2 |
| 09SRTF737-4 | 1 | 2 | 1 | 3 | 1 | 2 | 0 | 2 | 0 | 3 |
| 09SRTF788-1 | 1 | 2 | 1 | 2 | 1 | 2 | 1 | 2 | 0 | 3 |
| Alliance | 4 | n/a | 4 | n/a | 4 | n/a | 4 | n/a | 2 | n/a |
| Alzon | 1 | n/a | 4 | n/a | 2 | n/a | 1 | n/a | 0 | n/a |
| Aristotle | 4 | n/a | 4 | n/a | 4 | n/a | 4 | n/a | 2 | n/a |
| 207SRTC1802 | 4 | n/a | 4 | n/a | 4 | n/a | 4 | n/a | 0 | n/a |
| CM334 | 0 | 1 | 0 | 1 | 0 | 1 | 0 | 1 | 0 | 1 |
| JD | 4 | 4 | 4 | 4 | 4 | 4 | 4 | 4 | 4 | 4 |
| Paladin | 4 | n/a | 4 | n/a | 4 | n/a | 1 | n/a | 0 | n/a |
| 08SR912 | 3 | 2 | 3 | 2 | 0 | 2 | 0 | 3 | 0 | 4 |
| Revolution | 4 | n/a | 4 | n/a | 4 | n/a | 2 | n/a | 2 | n/a |
| Zenel | 4 | n/a | 4 | n/a | 4 | n/a | 4 | n/a | 0 | n/a |

Figure 5:

Numbers indicate the level of susceptibility (i.e., the number of fallen leaves through the stem test or on a 0-5 score based on the Bosland root test). Both CM 334 and 08SR912 show good level of resistance to all isolates, including the most virulent one, S197.
Stem test
4—From 3 to 4 leaves necrosed/fallen
3—From 2 to 3 leaves necrosed/fallen
2—From 1 to 2 leaves necrosed/fallen
1—From 0 to 1 leaf necrosed/fallen
0—no leaf necrosed
Root Test
4—3 < x < 5
3—2 < x < 3
2—1 < x < 2
1—0 < x < 1
0—no symptom '09SRTF712-4' and '09SRTF713-5' show the best level of resistance but the fruit is still a bit long, rectangular and of the ¾ long type. '09SRTF776-4', and '09SRTF737-4' have a good level of resistance as well as good fruit quality with the desired blocky shape. '09SRTF788-1' has a good level of resistance as well as good fruit quality with the desired half long fruit shape (FIG. 5).

In summary, the five lines (i.e., '09SRTF776-4', '09SRTF712-4', '09SRTF713-5', '09SRTF737-4' and '09SRTF788-1') contain at least the following QTL combinations for resistance:

One *Phytophthora* Resistance QTL on Linkage Group 1/8 (LG1/8) originating from the F7 line 05SRTF569-5 for all five lines '09SRTF776-4', '09SRTF712-4', '09SRTF713-5', '09SRTF737-4' and '09 SRTF788-1'.

One *Phytophthora* Resistance QTL on LG3 originating from the F7 line 05SRTF569-5 for all five lines '09SRTF776-4', '09SRTF712-4', '09SRTF713-5', '09SRTF737-4' and '09SRTF788-1'.

One *Phytophthora* Resistance QTL on LG5, originating from the F7 line 05SRTF569-5 for all five lines '09SRTF776-4', '09SRTF712-4', '09SRTF713-5', '09SRTF737-4' and '09SRTF788-1'.

One *Phytophthora* Resistance QTL on LG10, originating from the F7 line 05SRTF569-5 for all five lines '09SRTF776-4', '09SRTF712-4', '09SRTF713-5', '09SRTF737-4' and '09SRTF788-1'.

*Phytophthora* Resistance QTL on LG6, originating from the F7 line 05SRTF569-5 for the '09SRTF712-4' and '09SRTF713-5' lines and from the '07SRTC1802' line for the '09SRTF776-4', '09SRTF788-1' and '09SRTF737-4' lines.

Linkage Group 1/8 refers to Chromosome 1 and Chromosome 8. The term is used to reflect that the two chromosomes could not be separated from each other because of pseudolinkage as a result of reciprocal translocation involving these two chromosomes, see Paran et al., 2004 and Livingstone et al., 1999.

It can also be determined from the molecular marker analysis that:

(1) LG 1/8 contains a fruit weight QTL (f.w. 8.1) originating from the F7 line for all five lines.

(2) LG2 contains the fruit weight QTL (fw2.2) originating from the F7 line for '09SRTF712-4', '09SRTF713-5' and '09SRTF776-4' and the one originating from '07SRTC1802 for lines '09SRTF737-4' and '09SRTF788-1'.

(3) LG3 contains a fruit shape QTL (fs3.1) originating from the F7 line for '09SRTF712-4' and '09SRTF713-5' and the one originating from '07SRTC1802' line for '09SRTF776-4', '09SRTF788-1' and '09SRTF737-4'.

(4) LG10 contains a fruit shape QTL (fs10.1) originating from the F7 line for '09SRTF713-5' and '09SRTF776-4' and the one originating from '07SRTC1802' line for '09SRTF788-1', '09SRTF737-4' and '09SRTF712-4'.

Without wishing to be bound by any particular theory, it can be concluded that the recombination that took place on both Linkage 3 and 6 are of high importance for the present invention, because:

(1) Regarding the fruit shape, the plants '09SRTF712-4' and '09SRTF713-5' are of the ¾ long type shape. This shape, somewhat in between the blocky type of the '07SRTC1802' parent and the horn type of the F7 parent, is due to the F7 fruit shape QTL on Linkage 3 (fs 3.1) that has been introgressed during the breeding process. The plants '09SRTF776-4', and '09SRTF737-4' are of the blocky type shape because they have kept the original '07SRTC1802' fruit shape QTL on Linkage Group III (LG3) for '09SRTF788-1' and '09SRTF737-4' during the breeding process. The plant '09SRTF788-1' has a half long fruit shape.

(2) Regarding the *Phytophthora* resistance, the plants '09SRTF712-4' and '09SRTF713-5' are more resistant than the plants '09SRTF776-4', '09SRTF788-1' and '09SRTF737-4' due to the introgression of the F7 *Phytophthora* resistance QTL on Linkage Group 6 (LG6) that has been introgressed during the breeding process. The plants '09SRTF776-4', '09SRTF788-1' and '09SRTF737-4' are less resistant than the plants '09SRTF712-4' and '09SRTF713-5' presumably because they have kept the original '07SRTC1802' background on the additional resistance QTL on Linkage Group 6 (LG6) during the breeding process. Plants '09SRTF712-4' and '09SRTF713-5' are more resistant than any other plants available as of today and both are resistant to all 5 aggressive isolates.

By combining phyto-pathology tests with aggressive isolates (especially 'S197') and molecular marker pressure, the present invention demonstrates the successful introgression important *Phytophthora* resistance QTLs into a sweet pepper of good agronomic value, whether from the blocky or from the rectangular ¾ long type.

The genotyping results are shown in Table 5 (A=from F7 line; B=from '07SRTC1802').

The genotyping results indicate:

(1) For chromosome 1/8 (LG1/8), the resistance QTL has been successfully transferred from F7 to the '07SRTC1802' background progenies. The fw 8.1 has also been transferred, even if this was not the primary goal.

(2) For chromosome 2 (LG2), the fw 2.2 from the F7 line has been transferred for three of the lines, but it is rather difficult to interpret as we do not have clear cut distinctions between the two types, blocky vs. ¾ long s.

(3) For chromosome 3 (LG3), the resistance QTL has been successfully transferred from F7 to the '07SRTC1802' background progenies. The fw 3.1 has also been transferred for '09SRTF712-4' and '09SRTF713-5', even if this was not the primary goal. This result explains the ¾ long rectangular shape of the fruit on these plants.

(4) For chromosome 5 (LG5), the resistance QTL has been successfully transferred from F7 to the '07SRTC1802' background progenies.

(5) For chromosome 6 (LG6), the resistance QTL has been successfully transferred from F7 to the '07SRTC1802' background progenies for 09SRTF712-4 and 09SRTF713-54 but not for 09SRTF776-4, 09SRTF788-1 and 09SRTF37-4, which may explain the resistance being slightly weaker for these three lines versus the 712 and 713 progenies.

(6) For chromosome 10 (LG 10), the resistance QTL has been successfully transferred from F7 to the '07SRTC 1802' background progenies and the fruits shape QTL is more doubtful varying among the lines.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present applica-

TABLE 5

| | SSR primers profiles for the starting lines and 5 progeny lines | | | | | | | |
|---|---|---|---|---|---|---|---|---|
| | LG1 | | LG8 | LG2 | | | LG3 | |
| | CAMS117 | CP10061 | Hpms MADS | HpmsE090 | EPMS709 | PAPR2 | CA517699 | EPMS648 |
| F7 line (starting) | B | B | B | B | B | B | B | B |
| 07SRTC1802 (starting) | A | A | A | A | A | A | A | A |
| 09SRTF712-4 (progeny) | B | B | B | A | A | B | B | B |
| 09SRTF713-5 (progeny) | B | B | B | B | A | B | B | B |
| 09SRTF776-4 (progeny) | B | B | B | A | B | B | B | A |
| 09SRTF788-1 (progeny) | B | B | B | A | B | A | B | A |
| 09SRTF737-4 (progeny) | B | B | B | A | H | A | B | A |
| | QTL phyto* | | fw8.1 | QTL phyto | | fw2.2 | QTL phyto | fs3.1 |

| | LG5 | | | LG6 | LG10 | |
|---|---|---|---|---|---|---|
| | CAMS190 | CAMS420 | Epms749 | AF208834 | CAMS460 | GPMS159 |
| F7 line (starting) | B | B | B | B | B | B |
| 07SRTC1802 (starting) | A | A | A | A | A | A |
| 09SRTF712-4 (progeny) | B | B | B | B | B | A |
| 09SRTF713-5 (progeny) | B | B | B | B | B | B |
| 09SRTF776-4 (progeny) | B | B | B | A | B | B |
| 09SRTF788-1 (progeny) | B | B | B | A | B | A |
| 09SRTF737-4 (progeny) | B | B | B | A | B | A |
| | | | QTL phyto | QTL phyto | QTL phyto | fs10.1 |

*"phyto" refers to phytophotora resistance tion. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

Thabuis et al., 2003. Comparative mapping of *Phytophthora* resistance loci in pepper germplasm: evidence for conserved resistance loci across Solanaceae and for a large genetic diversity. TAG 106:1473-1485

Thabuis et al., 2004a. Marker-assisted introgression of 4 *Phytophthora capsici* resistance QTL alleles into a bell pepper line: validation of additive and epistatic effects. Molecular breeding 14: 9-20

Thabuis et al., 2004b. Phenotypic and molecular evaluation of a recurrent selection program for a polygenic resistance to *Phytophthora capsici* in pepper. TAG 109:342-351

Lefebvre V, Palloix A. 1996. Both epistatic and additive effects of QTLs are involved in polygenic induced resistance to disease: a case study, the interaction pepper—*Phytophthora capsici* Leonian. Theor. Appl. Genet. 93: 503-511.

Ben Chaim et al., 2001. QTL mapping of fruit related traits in pepper. TAG 102:1016-1028.

Ben Chaim A., Borovsky Y., Rao G. U., Tanyolac B., Paran I., 2003a. fs3.1: a major fruit shape QTL conserved in *Capsicum*. Genome, 46: 1-9

Ben Chaim A., Borovsky Y., De Jong W., Paran I., 2003b. Linkage of the A locus for the presence of anthocyanin and fs10.1 a major fruit-shape QTL in pepper, Theor Appl Genet, 106: 889-894

Bosland P. W., Lindsey D. L., 1991. A seedling screen for *Phytophthora* root rot in pepper *capsicum annuum*. Plant Disease 75, no. 10, 1048-1050

Barchi et al., 2009. QTL analysis of plant development and fruit traits in pepper and performance of selective phenotyping. Theor Appl Genet.

Cooke D. E. L., Duncan J. M., Williams N. A., Hagenaar-de Weerdt M. and Bonants P. J. M. (2000) Identification of *Phytophthora* species on the basis of restriction enzyme fragment analysis of the internal transcribed spacer regions of ribosomal RNA, Bulletin OEPP/EPPO Bulletin 30, 519-523.

Ogundiwin et al., 2005. Construction of 2 intraspecific linkage maps and identification of resistance QTLs for *Phytophthora capsici* root-rot and foliar-blight diseases of pepper (*Capsicum annuum* L.). Genome 48:698-711.

Rao et al., 2003. Mapping of yield-related QTL in pepper in an interspecific cross of *Capsicum annuum* and *C. frutescens*. Theor Appl Genet, 106: 1457-1466.

Sy et al, 2005. Inheritance of *Phytophthora* stem blight resistance as compared to *Phytophthora* root rot and *Phytophthora* foliar blight resistance in *Capsicum annuum* L. J. Amer. Soc. Hort. Sci. 130(1), pp 75-78.

Zygier S., Ben Chaim A., Efrati A., Kaluzky G., Borovsky Y., Paran I., 2005. QTLs mapping for fruit size and shape in chromosomes 2 and 4 in pepper and a comparison of the pepper QTL map with that of tomato. Theor Appl Genet, 111: 437-445

Sugita et al., 2006. QTL analysis for resistance to *Phytophthora* Blight using an intraspecific DH population of *Capsicum annuum*. Breeding Science 56: 137-145

Bonnet et al., 2007. Are the polygenic architectures of resistance to *Phytophthora capsici* and *P. parasitica* independent in pepper. Theor. Appl. Genet.

Minamiyama et al., 2007. QTL analysis for resistance to *Phytophthora capsici* in pepper using a high density SSR-based map. Breeding Science 57: 129-134

Oelke and Bosland, 2003. Differentiation of race specific resistance to *Phytophthora* root rot and foliar blight in *Capsicum annuum*. J. Amer. Soc. Hort. Sci. 128(2), pp 213-218.

Glosier et al, 2007. A differential series of pepper (*Capsicum annuum*) lines delineates fourteen physiological of *Phytophthora capsici*. Euphytica, 10.2007.

Mcleod et al., 2001, Phylogenetic relationships of *Capsicum* (Solanaceae) using DNA sequences from two noncoding regions: the chloropast atpB-rbcL spacer region and nuclear waxy introns Eshbaugh W H (1993) Peppers: history and exploitation of a serendipitous new crop discovery. In: Janick J, Simon J E (eds) New crops. Wiley, New York, pp 132-139

Adetula O A (2006) Genetic diversity of *Capsicum* using random amplified polymorphic DNAs. Afr J Biotechnol 5:120-122

Ince A G, Karaca M, Onus A N (2009) Development and utilization of diagnostic DAMD-PCR markers for *Capsicum* accessions. Genet Resour Crop Evol 56:211-221

Guzman F A, Ayala H, Azurdia C, Duque M C, de Vicen M C (2005) AFLP assessment of genetic diversity of *Capsicum* genetic resources in Guatemala: Home gardens as an option for conservation. Crop Sci 45:363-370

Prince J P, Loaiza-Figueroa F, Tanksley S D (1992) Restriction fragment length polymorphism and genetic distance among Mexican accessions of *Capsicum*. Genome 35:726-732

Rodriguez J M, Berke T, Engle L, Nienhuis J (1999) Variation among and within *Capsicum* species revealed by RAPD markers. Theor Appl Genet 99:147-156

Lefebvre V, Goffinet B, Chauvet J C, Caromel B, Signoret P, Brand R, Palloix A (2001) Evaluation of genetic distances between pepper inbred lines for cultivar protection purposes: comparison of AFLP, RAPD and phenotypic data. Theor Appl Genet 102:741-750

Heiser C B Jr, P G Smith 1948 Observations on another species of cultivated pepper, *Capsicum pubescens* R&P. Proc Am Soc Hortic Sci 52:331-335.

Heiser C B Jr, P G Smith 1953 The cultivated *Capsicum* peppers. Econ Bot 7:214-227.

Heiser C B Jr, P G Smith 1958 New species of *Capsicum* from South America. Brittonia 10:194-201.

Pickersgill 1971 Relationships between weedy and cultivated forms in some species of chili peppers (genus *Capsicum*). Evolution 25: 683-691.

Smith P G, C B Heiser Jr 1951 Taxonomic and genetic studies on the cultivated peppers, *Capsicum annuum* L. and *C. frutescens* L. Am J Bot 38:362-368.

Eshbaugh W H 1976 Genetic and biochemical systematic studies of chili peppers (*Capsicum*—Solanaceae). Bull Torrey Bot Club 102:396-403.

Eshbaugh W H 1970 A biosystematic and evolutionary study of *Capsicum* baccatum (Solanaceae). Brittonia 22:31-43.

Lippert L F, P G Smith, B O Bergh 1966 Cytogenetics of the vegetable crops: garden pepper; *Capsicum* sp. Bot Rev 32:25-55.

Emboden W A Jr 1961 A preliminary study of the crossing relationships of *Capsicum* baccatum. Butler Univ Bot Stud 14:1-5.

Hospital, F., C. Chevalet and P. Mulsant, 1992, Using markers in gene introgression breeding programs. Genetics 132: 1199-1210.

Hospital, F., and A. Charcosset, 1997a, Marker-assisted introgression of quantitative trait loci. Genetics 147: 1469-1485.

Hospital, F., L. Moreau, F. Lacoudre, A. Charcosset and A. Gallais, 1997b More on the efficiency of marker assisted selection Theor. Appl. Genet. 95: 1181-1189.

Hospital et al., 2000, Efficient marker-based recurrent selection for multiple quantitative trait loci, Genet. Res. 75: 357-368.

Moreau, L., A. Charcosset, F. Hospital and A. Gallais, 1998 Marker-assisted selection efficiency in populations of finite may be size. Genetics 148: 1353-1365.

Pochard E., Clerjeau M., Pitrat M. 1976. La resistance du piment, *Capsicum annuum* L., à *Phytophthora capsici* Leon. I. Mise en évidence d'une induction progressive de la résistance. Ann. Amélior. Plant. 26: 35-50.

Pochard E., Daubèze A. M. 1980. Recherche et évaluation des composantes d'une résistance polygénique: la résistance du piment à *Phytophthora capsici*. Ann. Amélior. Plant. 26: 377-398.

Lefebvre V, Palloix A. 1996. Both epistatic and additive effects of QTLs are involved in polygenic induced resistance to disease: a case study, the interaction pepper—*Phytophthora capsici* Leonian. Theor. Appl. Genet. 93: 503-511.

Barksdale, T. H., Papavizas, a. c., and Johnston, S. A. 1984. Resistance to foliar blight and crown rot of pepper caused by *Phytophthora capsici*. Plant Dis. 68: 506-509.

Reifschneider, F. J. B., Boeteux, L. S., Vecc la, and Kuroda, N. 1992. Inheritance of adult-plant resistance to *Phytophthora capsici* in pepper. Euphytica, 62:45-49

Ortega, R, Espanol, C. P., and Zueco, J. C. 1991. Genetics of resistance to *Phytophthora capsici* in the pepper line 'SM-334'. Plant Breed. 107: 50-55.

Ortega, R., Palazôn Espanol, c., and Cuartero Zueco, J. 1992. Genetic relationships among four pepper genotypes resistant to *Phytophthora capsici*. Plant Breed. 108: 118-125.

Oelke, L. M., Bosland, P. W., and Steiner, R. 2003. Differentiation of race specific resistance to *Phytophthora* root rot and foliar blight in. *Capsicum annuum*. J. Am. Soc. Hort. Sci. 128: 213-218.

Walker, S. 1., and Bosland, P. W. 1999 . . . Inheritance of *Phytophthora* root rot and foliar blight resistance in pepper. J. am. Soc. Hort. Sci. 124: 14-18.

Bartual, R., Carbonell, E. A., Marsal, J. I., TeHo, le., and Campo T. 1991. Gene action in the resistance of peppers (*Capsicum annuum*) to *Phytophthora* stem blight (*Phytophthora capsici* L.) Euphytica, 54: 195-200.

Bartual, R., Lacasa, A., Marsal, J. I., and Tello, le. 1994. Epistasis in the resistance of pepper to *Phytophthora* stem blight (*Phytophthora capsici* L.) and its significance in the prediction of double cross performances. Euphytica, 72: 149-152.

Smith et al., 1967, Inheritance of resistance in peppers to *Phytophthora* root rot. Phytopathology 57:377-379

Kim, Y J., Hwang, B. K., and Park, K. W. 1989. Expression of age related resistance in pepper plants infected with *Phytophthora capsici*. Plant Dis. 73: 745-747.

Palloix, A, Daubeze, A. M., and Pochard, E. 1988. *Phytophthora* root rot of pepper influence of host genotype and pathogen strain on the inoculum density-disease severity relationships. J. Phytopathology, 123: 25-33.

Palloix, A., Daubeze, A. M, Phaly, T., and Pochard, E. 1990. Breeding transgressive lines of pepper for resistance to *Phytophthora capsici* in a recurrent selection system. Euphytica, 51: 141-150.

Lorez and Wenzel, 2007, Molecular Marker Systems in Plant Breeding and Crop Improvement, Volume 55 of Biotechnology in Agriculture and Forestry, ISBN 3540740066, 9783540740063

Srivastava and Narula, 2004, Plant biotechnology and molecular markers, ISBN 1402019114, 9781402019111

Meksem and Kahl, 2005, The handbook of plant genome mapping: genetic and physical mapping, Wiley-VCH, ISBN3527311165, 9783527311163

Phillips and Vasil, 2001, DNA-based markers in plants, Volume 2, Part 1 *Volume 6 of Advances in cellular and molecular biology of plants* Springer, ISBN 0792368657, 9780792368656

Arous et al., 2001, Plant regeneration from zygotic embryo hypocotyls of Tunisian chili (*Capsicum annuum* L.), J. Appl. Hort., 3(1):17-22, January-June, 2001

Sharma, 2007, Micropropagation of *Capsicum annuum* L., Not. Bot. Hort. Agrobot. Cluj, 2007 Volume 35, Issue 1 Print ISSN 0255-965x; Electronic ISSN 1842-4309

Agrawal et al., 1989, Plant regeneration in tissue cultures of pepper (*Capsicum annuum* L. cv. mathania), Plant Cell, Tissue and Organ Culture, 16(1):47-55

Harini and Sita, 1993, Direct somatic embryogenesis and plant regeneration from immature embryos of chili (*Capsicum annuum* L.), Plant Science, 89(1):107-112

Kothari et al., 2010, Chili peppers—a review on tissue culture and transgenesis. Biotechnol Adv. 2010 January-February; 28(1):35-48.

Toth et al., Application of silicon rubber grafting clips for in vitro phytopathological studies, ISHS Acta Horticulturae 725: V International Symposium on In Vitro Culture and Horticultural Breeding Kokalis-Burelle et al., 2009, Greenhouse evaluation of *Capsicum* rootstocks for management of *Meloidogyne incognita* on grafted bell pepper, Nematorpica, 39(1): 121-132

DeWitt and Bosland, 2009, The Complete Chile Pepper Book: A Gardener's Guide to Choosing, Growing, Preserving, and Cooking, Publisher Timber Press, 2009 ISBN0881929204, 9780881929201

Paran et al., 2004, An integrated genetic linkage map of pepper (*Capsicum* spp.), Molecular Breeding 13: 251-261

Livingstone et al., 1999, Genome Mapping in *Capsicum* and the Evolution of Genome Structure in the Solanaceae, Genetics, 152:1183-1202

The invention claimed is:

1. A *Capsicum annuum* plant resistant to *Phytophthora capsici*, comprising quantitative Trait Loci (QTLs) associated with resistance to *Phytophthora capsici*, wherein the QTLs map to linkage groups LG1/8, L03, LG5, and LG10, and wherein said plant has a blocky type, a ¾ long type, or a half long type fruit shape, wherein the QTL from LG1/8 is genetically linked to molecular marker CAMS117 identified by amplification product of primers CAMS117-F and CAMS117-R, or linked to molecular marker CP10061 identified by amplification product of primers CP10061-F and CP10061-R, wherein the QTL from LG3 is genetically linked to molecular marker CA517699 identified by amplification product of primers CA517699-F and CA517699-R, wherein the QTL from LG5 is genetically linked to molecular marker CAMS420 identified by amplification product of primers CAMS420-F and CAMS420-R, or linked to molecular marker CAMS190 identified by amplification product of primers CAMS190-F and CAMS190-R, or linked to molecular marker Epms749 identified by amplification product of primers Epms749-F and Epms749-R, and wherein the QTL from LG10 is genetically linked to molecular marker CAMS460 identified by amplification product of primers CAMS460-F and CAMS460-R.

2. The *Capsicum annuum* plant of claim 1, further comprising one or more QTLs associated with resistance to *Phytophthora capsici* mapping to linkage group LG2 and/or LG6, wherein the QTL from LG2 is genetically linked to molecular marker HpmsE090 identified by amplification product of primers HpmsE090-F and HpmsE090-R, or linked to molecular marker EPMS709 identified by amplification product of primers EPMS709-F and EPMS709-R, and wherein the QTL from LG6 is genetically linked to molecular marker AF208834 identified by amplification product of primers AF208834-F and AF208834-R.

3. The *Capsicum annuum* plant of claim 2, wherein the molecular marker AF208834 comprises about 228 nucleic acid base pairs.

4. The *Capsicum annuum* plant of claim 3, wherein the plant has a *Phytophthora capsici* resistance score of 0 based on the stem decapitation test using *P. capsici* isolate 'S197' and a rating score of 0 to 5.

5. The *Capsicum annuum* plant of claim 2, wherein the molecular marker AF208834 comprises about 224 nucleic acid base pairs.

6. The *Capsicum annuum* plant of claim 5, wherein the plant has a *Phytophthora capsici* resistance score of 1 or 2 based on the stem decapitation test using *P. capsici* isolate 'S197' and a rating score of 0 to 5.

7. The *Capsicum annuum* plant of claim 1, wherein the plant has a level of resistance to *P. capsici* isolate 'S197' which is at least higher to the level of resistance of a susceptible check line selected from the group consisting of Alliance, Aristotle, Revolution.

8. The *Capsicum annuum* plant of claim 1, wherein the plant comprises one or more QTLs associated with fruit shape and/or fruit weight, wherein the QTLs associated with fruit shape and/or fruit weight map to linkage groups LG2, L63, LG1/8, and/or LG10, and wherein the QTL from LG2 associated with fruit shape and/or fruit weight is genetically linked to molecular marker PAPR2 identified by amplification product of primers PAPR2-F and PAPR2-R, wherein the QTL from LG3 associated with fruit shape and/or fruit weight is genetically linked to molecular marker EPMS648 identified by amplification product of primers EPMS648-F and EPMS648-R, wherein the QTL from LG1/8 associated with fruit shape and/or fruit weight is genetically linked to molecular marker HpmsMADS identified by amplification product of primers HpmsMADS-F and HpmsMADS-R, and wherein the QTL from LG10 associated with fruit shape and/or fruit weight is genetically linked to molecular marker GPMS159 identified by amplification product of primers GPMS159-F and GPMS159-R.

9. The *Capsicum annuum* plant of claim 8, wherein the molecular marker EPMS648 comprises about 188 nucleic acid base pairs and the plant has the ¾ long fruit shape.

10. The *Capsicum annuum* plant of claim 8, wherein the molecular marker EPMS648 comprises about 186 nucleic acid base pairs and the plant has blocky fruit shape.

11. A plant part obtained from the plant of claim 1.

12. The plant part of claim 11, wherein the plant part is a seed, a fruit, a scion, or a rootstock.

13. A plant cell derived from the plant of claim 1.

14. A method for selecting the plant of claim 1, comprising the steps of:

(i) detecting the presence of one or more QTLs associated with resistance to *Phytophthora capsici* as indicated by the presence of one or more molecular markers selected from CAMS117, CP10061, CA517699, CAMS420, CAMS190, Epms749, CAMS460, wherein the QTLs are genetically linked to one of more said molecular markers;

(ii) detecting the presence of one or more QTLs associated with fruit shape and/or fruit weight as indicated by the presence of one or more molecular markers selected from PAPR2, EPMS648, HpmsMADS, GPMS159, wherein the QTLs are genetically linked to one of more said molecular markers;

(iii) selecting the plant comprising QTLs associated with resistance to *Phytophthora capsici* from linkage groups LG1/8, LG3, LG5, and LG10, and QTLs associated with fruit shape and/or fruit weight from linkage groups LG2, LG3, LG1/8, and/or LG10; and (iv) optionally, confirming resistance to *Phytophthora capsici* in the plant of step (iii) based on a stem decapitation test using *P. capsici* isolate 'S197', wherein the plant has a *Phytophthora capsici* resistance score of 0 to 2.

15. The method of claim 14, wherein the molecular marker CAMS117 is defined by amplification product of primers CAMS117-F and CAMS117-R; the molecular marker CP10061 is defined by amplification product of primers CP10061-F and CP 10061-R;

the molecular marker CA517699 is defined by amplification product of primers CA517699-F and CA517699-R; the molecular marker CAMS420 is defined by amplification product of primers CAMS420-F and CAMS420-R; the molecular marker CAMS190 is defined by amplification product of primers CAMS190-F and CAMS190-R; the molecular marker Epms749 is defined by amplification product of primers Epms749-F and Epms749-R; the molecular marker CAMS460 is defined by amplification product of primers CAMS460-F and CAMS460-R; and wherein the amplification product by using primers CAMS117-F and CAMS117-R, CP10061-F and CP 10061-R, CA517699-F and CA517699-R, CAMS420-F and CAMS420-R, CAMS190-F and CAMS190-R, Epms749-F and Epms749-R, or CAMS460-F and CAMS460-R from the *Capsicum annuum* plant resistant to *Phytophthora capsici* is distinctive by size from an amplification product by using the same pair of primers from a check *Capsicum annuum* line, wherein the check *Capsicum annuum* line has a *Phytophthora capsici* resistance score of 3 to 5 based on a stem decapitation test using *P. capsici* isolate 'S197'.

16. The method of claim 14, wherein the method further comprises the steps of:

(i) detecting the presence of one or more QTLs associated with resistance to *Phytophthora capsici* as indicated by the presence of one or more molecular markers selected from HpmsE090, EPMS709, and AF208834, wherein the QTLs are genetically linked to one of more said molecular markers;

(ii) selecting the plant comprising QTLs associated with resistance to *Phytophthora capsici* from linkage groups LG2 and/or LG6.

17. The method of claim 16, wherein the molecular marker HpmsE090 is defined by amplification product of primers HpmsE090-F and HpmsE090-R; the molecular marker EPMS709 is defined by amplification product of primers EPMS709-F and EPMS709-R;

the molecular marker AF208834 is defined by amplification product of primers AF208834-F and AF208834-R; and wherein the amplification product by using primers HpmsE090-F and HpmsE090-R, EPMS709-F and EPMS709-R, or AF208834-F and AF208834-R from the *Capsicum annuum* plant resistant to *Phytophthora capsici* is distinctive by size from an amplification product by using the same pair of primers from a check *Capsicum annuum* line, wherein the check *Capsicum annuum* line has a *Phytophthora capsici* resistance score of 3 to 5 based on a stem decapitation test using *P. capsici* isolate 'S197'.

18. Seed of a *Capsicum annuum* line selected from the group consisting of '09SRTF713-5', '09SRTF776-4', and '09SRTF788-1', wherein a representative sample of seed has been deposited under NCIMB No 41791, 41792 and 41793, respectively.

19. A plant, or part thereof, obtainable by growing the seed of claim 18.

20. A plant having all of the physiological and morphological characteristics of the plant of claim 19.

21. A tissue culture of regenerable cells produced from the plant, or part thereof, of claim 19.

22. An ovule of the plant of claim 19.

23. A pollen of the plant of claim 19.

24. A method for producing *Capsicum annuum* seed comprising crossing the plant of claim 19 with itself or another *Capsicum annuum* plant, and harvesting the resultant seed.

25. The seed of claim 18 or the resultant seed obtained of claim 24, wherein a plant grown from the seed comprises QTLs associated with resistance to *Phytophthora capsici*, wherein the QTLs are genetically linked to molecular markers CAMS117, CAMS420, CA517699 and CAMS460 respectively, and wherein said plant having a blocky type, a ¾ long type, or a half long type fruit shape.

26. A plant produced by germinating the seed of claim 25.

27. A seed produced by the plant of claim 26, wherein a plant produced by germinating said seed comprises QTLs associated with resistance to *Phytophthora capsici*, wherein the QTLs are genetically linked to molecular markers CAMS117, CAMS420, CA517699 and CAMS460 respectively, and wherein said plant having a blocky type, a ¾ long type, or a half long type fruit shape.

28. A progeny of the plant of claim 19 that comprises QTLs associated with resistance to *Phytophthora capsici*, wherein the QTLs are genetically linked to molecular markers CAMS117, CAMS420, CA517699 and CAMS460 respectively, and wherein said plant has a blocky type, a ¾ long type, or a half long type fruit shape.

* * * * *

SEQUENCE LISTING

<160> NUMBER OF SEQ ID NOS: 28

<210> SEQ ID NO 1
<211> LENGTH: 26
<212> TYPE: DNA
<213> ORGANISM: Artificial Sequence
<220> FEATURE:
<223> OTHER INFORMATION: PAPR2-F

<400> SEQUENCE: 1
ccgctttaca agcggatagt tacgtg                                          26

<210> SEQ ID NO 2
<211> LENGTH: 25
<212> TYPE: DNA
<213> ORGANISM: Artificial Sequence
<220> FEATURE:
<223> OTHER INFORMATION: PAPR2-R

<400> SEQUENCE: 2 caccttttctt agtttattcg aatac                                          25

<210> SEQ ID NO 3
<211> LENGTH: 20
<212> TYPE: DNA
<213> ORGANISM: Artificial Sequence
<220> FEATURE:
<223> OTHER INFORMATION: EPMS-709-F

<400> SEQUENCE: 3
acgccgagga ctatgatgac                                                 20

<210> SEQ ID NO 4
<211> LENGTH: 20
<212> TYPE: DNA
<213> ORGANISM: Artificial Sequence
<220> FEATURE:
<223> OTHER INFORMATION: EPMS-709-R

<400> SEQUENCE: 4
ttcttcatcc tcagcgtgtg                                                 20

<210> SEQ ID NO 5
<211> LENGTH: 22
<212> TYPE: DNA
<213> ORGANISM: Artificial Sequence
<220> FEATURE:
<223> OTHER INFORMATION: HpmsE090-F

<400> SEQUENCE: 5
caccggccgt ttaaactttc ac                                              22

<210> SEQ ID NO 6
<211> LENGTH: 22
<212> TYPE: DNA
<213> ORGANISM: Artificial Sequence
<220> FEATURE:
<223> OTHER INFORMATION: HpmsE090-R

<400> SEQUENCE: 6
gctggagttt ccaaaggaca aa                                              22

<210> SEQ ID NO 7
<211> LENGTH: 20
<212> TYPE: DNA
<213> ORGANISM: Artificial Sequence

```
<220> FEATURE:
<223> OTHER INFORMATION: CA517699-F

<400> SEQUENCE: 7
acgccaagaa aatcatctcc                                        20

<210> SEQ ID NO 8
<211> LENGTH: 20
<212> TYPE: DNA
<213> ORGANISM: Artificial Sequence
<220> FEATURE:
<223> OTHER INFORMATION: CA517699-R

<400> SEQUENCE: 8
ccattgctga agaaaatggg                                        20

<210> SEQ ID NO 9
<211> LENGTH: 26
<212> TYPE: DNA
<213> ORGANISM: Artificial Sequence
<220> FEATURE:
<223> OTHER INFORMATION: EPMS-648-F

<400> SEQUENCE: 9
tgtaaaataa aataaggcta aaggca                                 26

<210> SEQ ID NO 10
<211> LENGTH: 20
<212> TYPE: DNA
<213> ORGANISM: Artificial Sequence
<220> FEATURE:
<223> OTHER INFORMATION: EPMS-648-R

<400> SEQUENCE: 10
caagaaagtg tgccccaaat                                        20

<210> SEQ ID NO 11
<211> LENGTH: 25
<212> TYPE: DNA
<213> ORGANISM: Artificial Sequence
<220> FEATURE:
<223> OTHER INFORMATION: CAMS_190-F

<400> SEQUENCE: 11
tttctgcagt gttaccaata tttca                                  25

<210> SEQ ID NO 12
<211> LENGTH: 19
<212> TYPE: DNA
<213> ORGANISM: Artificial Sequence
<220> FEATURE:
<223> OTHER INFORMATION: CAMS_190-R

<400> SEQUENCE: 12
cccatgggtc ctacctcag                                         19

<210> SEQ ID NO 13
<211> LENGTH: 22
<212> TYPE: DNA
<213> ORGANISM: Artificial Sequence
<220> FEATURE:
<223> OTHER INFORMATION: CAMS_420-F

<400> SEQUENCE: 13
cagcgttcta tcgtctcaaa tg                                     22
```

```
<210> SEQ ID NO 14
<211> LENGTH: 22
<212> TYPE: DNA
<213> ORGANISM: Artificial Sequence
<220> FEATURE:
<223> OTHER INFORMATION: CAMS_420-R

<400> SEQUENCE: 14
ttgacaaacc agaaattgat cg                                              22

<210> SEQ ID NO 15
<211> LENGTH: 20
<212> TYPE: DNA
<213> ORGANISM: Artificial Sequence
<220> FEATURE:
<223> OTHER INFORMATION: EPMS-749-F

<400> SEQUENCE: 15
tcccacgagt cttttttgagg                                                20

<210> SEQ ID NO 16
<211> LENGTH: 20
<212> TYPE: DNA
<213> ORGANISM: Artificial Sequence
<220> FEATURE:
<223> OTHER INFORMATION: EPMS-749-R

<400> SEQUENCE: 16
aaagggaatt atggggttgg                                                 20

<210> SEQ ID NO 17
<211> LENGTH: 23
<212> TYPE: DNA
<213> ORGANISM: Artificial Sequence
<220> FEATURE:
<223> OTHER INFORMATION: AF208834-F

<400> SEQUENCE: 17
tgcaccaagg tccagtaagg ttg                                             23

<210> SEQ ID NO 18
<211> LENGTH: 23
<212> TYPE: DNA
<213> ORGANISM: Artificial Sequence
<220> FEATURE:
<223> OTHER INFORMATION: AF208834-R

<400> SEQUENCE: 18
ccaaccacca tggttcatac aag                                             23

<210> SEQ ID NO 19
<211> LENGTH: 23
<212> TYPE: DNA
<213> ORGANISM: Artificial Sequence
<220> FEATURE:
<223> OTHER INFORMATION: HpmsMADS-F

<400> SEQUENCE: 19
tgctttcaaa acaatttgca tgg                                             23

<210> SEQ ID NO 20
<211> LENGTH: 25
<212> TYPE: DNA
<213> ORGANISM: Artificial Sequence
<220> FEATURE:
<223> OTHER INFORMATION: HpmsMADS-R
```

```
<400> SEQUENCE: 20
gcgtctaatg caaaacacac attac                                25

<210> SEQ ID NO 21
<211> LENGTH: 18
<212> TYPE: DNA
<213> ORGANISM: Artificial Sequence
<220> FEATURE:
<223> OTHER INFORMATION: CP10061-F

<400> SEQUENCE: 21
atcccaaaag gcaaaatc                                        18

<210> SEQ ID NO 22
<211> LENGTH: 18
<212> TYPE: DNA
<213> ORGANISM: Artificial Sequence
<220> FEATURE:
<223> OTHER INFORMATION: CP10061-R

<400> SEQUENCE: 22
atcccaaaag gcaaaatc                                        18

<210> SEQ ID NO 23
<211> LENGTH: 20
<212> TYPE: DNA
<213> ORGANISM: Artificial Sequence
<220> FEATURE:
<223> OTHER INFORMATION: CAMS117-F

<400> SEQUENCE: 23
ttgtggagga aacaagcaaa                                      20

<210> SEQ ID NO 24
<211> LENGTH: 20
<212> TYPE: DNA
<213> ORGANISM: Artificial Sequence
<220> FEATURE:
<223> OTHER INFORMATION: CAMS117-R

<400> SEQUENCE: 24
cctcagccca ggagacataa                                      20

<210> SEQ ID NO 25
<211> LENGTH: 25
<212> TYPE: DNA
<213> ORGANISM: Artificial Sequence
<220> FEATURE:
<223> OTHER INFORMATION: GPMS 159-F

<400> SEQUENCE: 25
aagaacatga ggaactttaa ccatg                                25

<210> SEQ ID NO 26
<211> LENGTH: 19
<212> TYPE: DNA
<213> ORGANISM: Artificial Sequence
<220> FEATURE:
<223> OTHER INFORMATION: GPMS 159-R

<400> SEQUENCE: 26
ttcacccttc tccgactcc                                       19
```

```
<210> SEQ ID NO 27
<211> LENGTH: 20
<212> TYPE: DNA
<213> ORGANISM: Artificial Sequence
<220> FEATURE:
<223> OTHER INFORMATION: CAMS460-F

<400> SEQUENCE: 27
cctttcactt cagcccacat                                              20

<210> SEQ ID NO 28
<211> LENGTH: 20
<212> TYPE: DNA
<213> ORGANISM: Artificial Sequence
<220> FEATURE:
<223> OTHER INFORMATION: CAMS460-R

<400> SEQUENCE: 28
accatccgct aagacgagaa                                              20
```